United States Patent
Dong et al.

(10) Patent No.: US 8,236,762 B2
(45) Date of Patent: Aug. 7, 2012

(54) PEPTIDE-CYTOTOXIC CONJUGATES

(75) Inventors: Zheng Xin Dong, Holliston, MA (US); Yeelana Shen, Franklin, MA (US); Michael DeWitt Culler, Hopkinton, MA (US); Christophe Alain Thurieau, Paris (FR); Jundong Zhang, Newton, MA (US); Sun Hyuk Kim, Needham, MA (US)

(73) Assignee: IPSEN Pharma S.A.S., Boulogne (FR)

( * ) Notice: Subject to any disclaimer, the term of this patent is extended or adjusted under 35 U.S.C. 154(b) by 460 days.

(21) Appl. No.: 12/311,961

(22) PCT Filed: Oct. 17, 2007

(86) PCT No.: PCT/US2007/022179
§ 371 (c)(1),
(2), (4) Date: Dec. 7, 2009

(87) PCT Pub. No.: WO2008/051421
PCT Pub. Date: May 2, 2008

(65) Prior Publication Data
US 2010/0113367 A1    May 6, 2010

Related U.S. Application Data

(60) Provisional application No. 60/853,140, filed on Oct. 20, 2006, provisional application No. 60/918,133, filed on Mar. 15, 2007.

(51) Int. Cl.
*A61K 38/31* (2006.01)
*A61K 38/04* (2006.01)
*A61P 5/02* (2006.01)
*C07K 14/655* (2006.01)
*C07K 5/00* (2006.01)
*C07K 7/00* (2006.01)
*C07K 16/00* (2006.01)
*C07K 17/00* (2006.01)

(52) U.S. Cl. ...................... 514/11.1; 530/329
(58) Field of Classification Search ................ None
See application file for complete search history.

(56) References Cited

FOREIGN PATENT DOCUMENTS
WO    WO 03/028527    4/2003
WO    WO 2004/093807    11/2004

OTHER PUBLICATIONS

Dasgupta, P., "Somatostatin analogues: Multiple roles in cellular proliferation, neoplasia and angiogenesis", Pharm. & Therapeutics, 2004, 102:61-85.
Fuselier, J. A. et al., "An adjustable release rate linking strategy for cytotoxin-peptide conjugates", Bioorganic & Medicinal Chem Letters, 2003, 13:799-803.
Kawato, Y. et al., "Intracellular roles of AN-38, a metabolite of the camptothecin derivative CPT-11, in the antitumor effect of CPT-11", Cancer Research, 1991, 51:4187-4191.
Moody, T. W. et al., "Camptothecin-somatostatin conjugates inhibit the growth of small cell lung cancer cells", Peptides, 2005, 26:1560-1566.
Sun L. et al., "Effects of camptothecin conjugated to a somatostatin analog vector on growth of tumor cell lines in cultures and related tumors in rodents", Drug Delivery, 2004:11:231-238.

*Primary Examiner* — Marcela M Cordero Garcia
(74) *Attorney, Agent, or Firm* — Yankwich & Associates; Tony K. Uhm; Pamela C. Ball

(57) ABSTRACT

The invention features targeted cytotoxic compounds and methods relating to their therapeutic use for the treatment of neoplasia and other conditions.

28 Claims, 3 Drawing Sheets

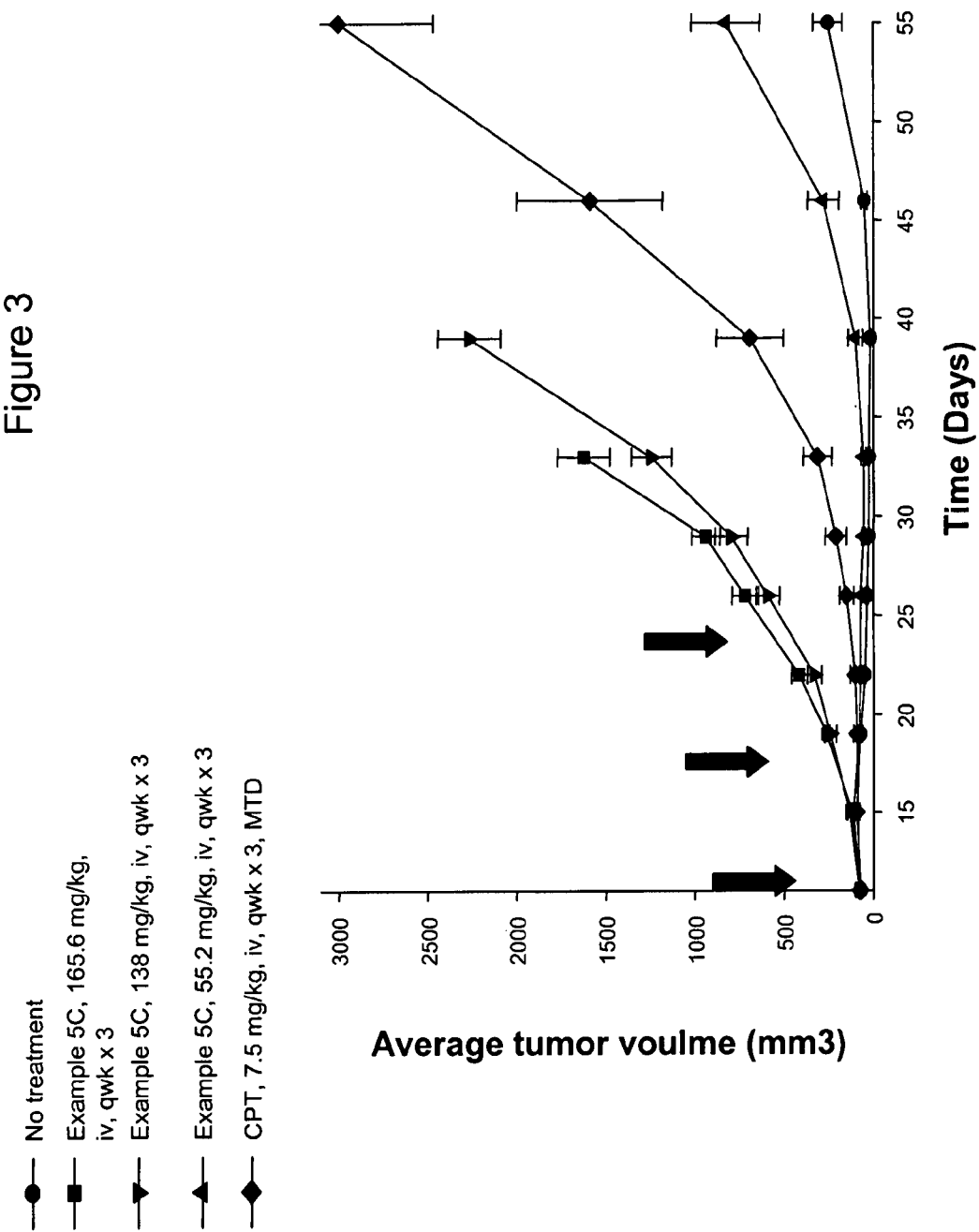

PEPTIDE-CYTOTOXIC CONJUGATES

This application is a United States national stage filing under 35 U.S.C. §371 of international (PCT) application No. PCT/US2007/022179, filed Oct. 17, 2007 and designating the US, which international application claims priority to U.S. provisional application No. 60/918,133, filed Mar. 15, 2007, and U.S. 60/853,140, filed Oct. 20, 2006.

FIELD OF THE INVENTION

The present invention relates to therapeutic compositions and their use in the treatment of disease states. More particularly, the present invention provides compounds, compositions and methods for treating disease or condition states associated with aberrant or undesirable cellular proliferation, migration and/or physiological activity.

BACKGROUND OF THE INVENTION

Most cytotoxic drugs exhibit undesirable toxic side effects due to their lack of selective action toward the tissues or cells requiring therapeutic effect. Various approaches have been pursued to achieve the selective delivery of cytotoxic agents to a target cell type.

Using biological receptor ligands as carriers of drugs to target these drugs to the cells of interest can reduce toxic side-effects and greatly improve the efficiency drug delivery. For example, International Patent Publication No. WO97/19954 discloses conjugates of an anthracycline cytotoxic agent such as doxorubicin with a peptide hormone such as LHRH, bombesin or somatostatin. The cytotoxic agent is covalently attached to the peptide via a linker of formula: —C(O)—(CH$_2$)$_n$—C(O)— wherein n=0-7.

Similarly, European Patent Application No. EP 1 118 336 discloses conjugates of somatostatin analogs, e.g., octreotide, lanreotide and vapreotide, and a cytotoxic drug, such as paclitaxel, doxorubicin or camptothecin, through a spacer wherein the spacer is also indicated to have the structure: —C(O)—(CH$_2$)$_n$—C(O)— wherein n=0-7.

U.S. Patent Application Publication No. 2002/0115596 discloses conjugates of cytotoxic agents and oligopeptides in which the amino acid sequences of the peptides are indicated to be cleaved preferentially by free prostate specific antigen. Such conjugates are said to be useful for the treatment of prostate cancer and benign prostatic hyperplasia.

U.S. Patent Application Publication No. 2003/0064984 discloses conjugates of cytotoxic analogs of CC-1065 and the duocarmycins with cleavable linker arms and a targeting agent such as an antibody or a peptide. The cytotoxic analogs are indicated to be released upon cleavage of the linker.

International Patent Application No. WO02/34237 discloses conjugates of active agents covalently attached directly to a polypeptide. The polypeptide is said to stabilize the active agent, e.g., in the stomach, through conformational protection.

International Patent Application No. WO04/093807 discloses targeted cytotoxic compounds conjugated with a ligand of a biological target.

There remains, however, a significant need for targeted cytotoxic drugs with improved properties with respect to targeting specificity, systemic toxicity and pharmacokinetics.

SUMMARY OF THE INVENTION

The instant invention provides targeted cytotoxic compounds comprising a cytotoxic moiety bound to a targeting moiety. The targeting moiety is, for example, a ligand of a biological receptor. Particular advantages of the compounds of the invention and uses thereof as treatments of tumors and cancers include, but are not limited to, a). lessened toxic side effects;
b). increased efficacy of treatment due to ability to administer higher doses, extend term of treatment, increase frequency of dosing and/or to localize and increase the drug concentration within the target cells; and/or
c). decreased complications from multi-drug resistance; or any combination thereof.

The application of targeted cytotoxic compounds is contemplated to aid in the treatment of a number of cancerous diseases or conditions. For example, treatment of tumors or cancers which over-express somatostatin receptors are contemplated to be targeted and treated by native somatostatin, i.e., H-Ala-Gly-Cys-Lys-Asn-Phe-Phe-Trp-Lys-Thr-Phe-Thr-Ser-Cys-OH (SEQ ID NO:1) and/or fragments or analogs thereof, complexed with particular cytotoxic moieties. Such cancers include, but are not limited to, neuroendocrine tumors (e.g., carcinoid tumors, neuroblastomas, gastrinomas, insulinomas, medullary thyroid cancers or merckel cell tumors), breast cancer carcinomas, lymphomas (Hodgkin's and non-Hodgkin's), leukemias, small cell lung cancers (SCLC), hepatomas, melanomas and renal carcinomas, all of which are known to exhibit increased levels of somatostatin type-2 receptor (SSTR-2). Prostate carcinomas and sarcomas are exemplary types of cancer which over-express somatostatin type-1 receptor, SSTR-1; in addition prostate cancers are also known to exhibit high levels of somatostatin type-4 receptor (SSTR-4). Pituitary adenomas exhibit increased levels of somatostatin type-5 receptor (SSTR-5). (See, Reubi, J. C. et al., Eur. J. Nucl. Med. Mod. Imaging, 2002, 29(7):855-62; Schally, A. V. et al., Life Sci., 2003, 72(21):2305-20; Hansson, J. et al., Prostate, 2002, 53(1):50-9; and Reubi, J. C. et al., Eur. J. Nucl. Med., 2001, 28(7):836-46.) Additional cancers or tumors which may be treated using compounds or compositions of the invention include, but are not limited to, adrenal medullary tumors (pheochromocytoma, neuroblastoma, ganglioneuroma), gastroenteropancreatic (GEP) tumors (glucagonoma, vasoactiveintestinal polypeptide secreting tumor (VIPoma), non-functioning GEP tumors), paraganglioma, pituitary adenoma, astrocytomas, benign and malignant bone tumors, differentiated thyroid carcinoma (papillary, follicular, Hurthle cell), meningioma, and non-small cell lung cancer (see Society of Nuclear Medicine Procedure Guideline for Somatostatin Receptor Scintigraphy with In-[111] Pentetreotide, Version 1.0, February 2001). Additional conditions or diseases benefiting from application of the compounds of the invention include but are not limited to autoimmune diseases (Graves' disease, Graves' opthalmopathy), bacterial pneumonia, cerebrovascular accident, fibrous dysplasia, granulomas (tuberculosis, sarcoid) and radiation pneumonitis (see Society of Nuclear Medicine Procedure Guideline for Somatostatin Receptor Scintigraphy with In-[111] Pentetreotide, Version 1.0, February 2001). Thus, the ability to target particular SSTR types with particular somatostatin analogs conjugated to cytotoxic moieties would aid in the treatment of the foregoing cancerous conditions.

In a similar fashion, tumors over-expressing bombesin receptors would benefit from the application of targeted cytotoxic compounds containing native bombesin, i.e. Tyr-Gln-Arg-Leu-Gly-Asn-Gln-Trp-Ala-Val-Gly-His-Leu-Met-NH$_2$ (SEQ ID NO:2) and/or fragments or analogs thereof. Such cancers include, but are not limited to, breast cancer, prostate cancer, lung cancer, small cell lung cancer, gastrinomas and renal cell carcinomas (See, Reubi, J. C., et al., Clin. Can. Res., 2002, 8(4):1139-46).

The instant invention also provides cytotoxic peptide conjugates useful for treating angiogenic and/or proliferative conditions. For example, the compounds of the invention may remedy conditions associated with newly formed nascent blood vessels expressing high levels of SSTR-2 (See, van Hagen, et al., Eur. J. Endocrinol., 2000, 143(Suppl.1):S43-51). Conditions associated with the formation of new blood vessels contemplated as targets for the compounds of the instant invention include, but are not limited to, angiogenesis, proliferative diabetic retinopathy, cystic macular odema, rheumatoid arthritis, endometriosis, restenosis and psoriasis.

In a first aspect of the invention, the cytotoxic moiety and targeting moiety are described by Formula IA:

A-B-C-E     (IA)

wherein:

A is camptothecin or a derivative thereof;

B is rvAbu, rvAhp, rvAla, rvAnc, rvApn, rvArg, rvAsp, rvCha, rvDap(Z), rvGlu, rvGly, rvPhe, or rvVal or deleted;

C is $D^1$-$D^2$-$D^3$-$D^4$ wherein $D^1$ is glutaryl, succinyl or deleted;

$D^2$ is (Doc)$_m$ wherein m is, independently for each occurrence thereof, 4, 5 or 6 or [Peg]$_x$ wherein x is, independently for each occurrence thereof, 0-100;

$D^3$ is (Aepa)$_n$ wherein n is, independently for each occurrence thereof, 0 or 1; and $D^4$ is D-Phe or Lys-D-Tyr-D-Tyr;

E is a somatostatin analog of the formula c(Cys-$A^2$-$A^3$-D-Trp-Lys-$A^6$-Cys)-$A^8$-R wherein $A^2$ is Phe or deleted;

$A^3$ is Phe, 3-(I)Tyr or Tyr, $A^6$ is Abu, Thr or deleted;

$A^8$ is Thr or deleted; and

R is $NH_2$ or OH;

or a pharmaceutically acceptable salt thereof.

A first embodiment of the first aspect of the invention features compounds of Formula (IA) having a camptothecin moiety selected from the group consisting of:

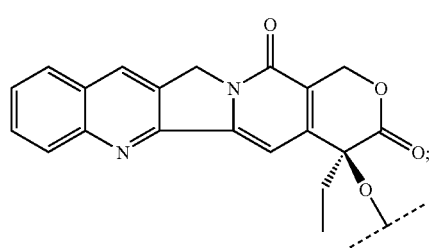

-continued

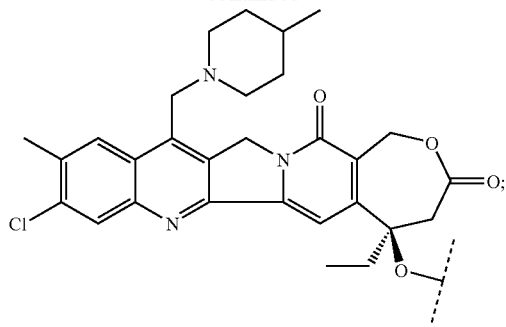

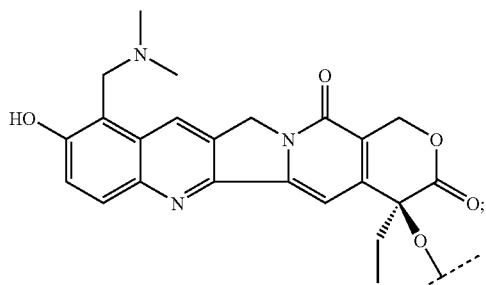

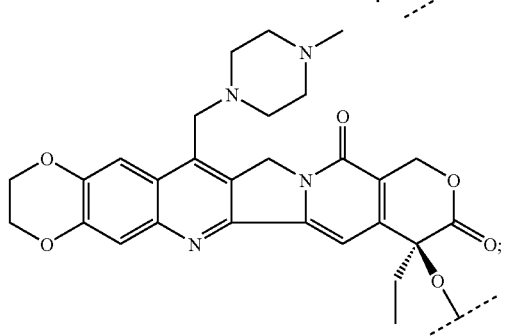

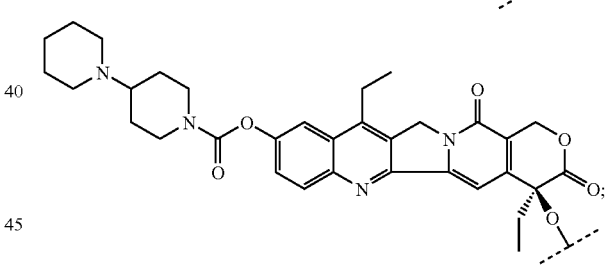

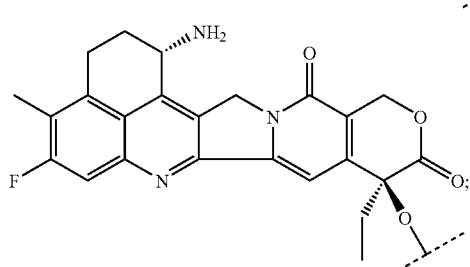

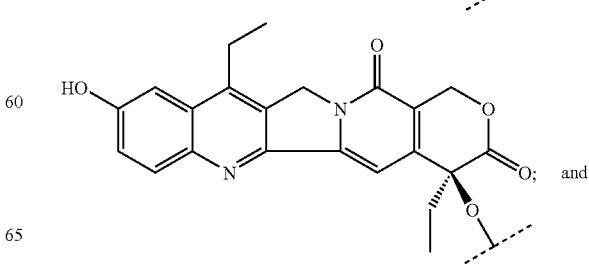

and

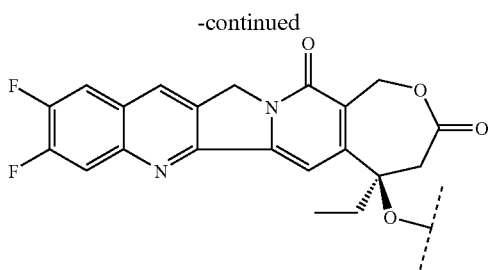

wherein the dashed line "----" in the above indicates the point of attachment of the camptothecin moiety to a second moiety, e.g., a linker or peptide.

A second embodiment of the first aspect of the invention features compounds according to Formula (IA) wherein the targeting moiety is native somatostatin or a fragment and/or analog thereof according to any one of the following formulae:

(SEQ ID NO: 1)
H-Ala-Gly-Cys-Lys-Asn-Phe-Phe-Trp-Lys-Thr-Phe-Thr-Ser-Cys-OH (Native SRIF);

c(Cys-3-(I)Tyr-D-Trp-Lys-Abu-Cys)-Thr-NH$_2$;

c(Cys-Phe-Phe-D-Trp-Lys-Thr-Cys)-NH$_2$; or c(Cys-Tyr-D-Trp-Lys-Abu-Cys)-Thr-NH$_2$ or a pharmaceutically acceptable salt thereof.

A third embodiment of the first aspect of the invention features any one of the following compounds:
Camptothecin-rvGly-Glut-(Doc)$_6$-Lys-D-Tyr-D-Tyr-c(Cys-3-(I)Tyr-D-Trp-Lys-Abu-Cys)-Thr-NH$_2$;
Camptothecin-rvGly-Glut-(Doc)$_4$-Lys-D-Tyr-D-Tyr-c(Cys-3-(I)Tyr-D-Trp-Lys-Abu-Cys)-Thr-NH$_2$;
Camptothecin-rvGly-Glut-(Doc)$_4$-Lys-D-Tyr-D-Tyr-c(Cys-Phe-Phe-D-Trp-Lys-Thr-Cys)-NH$_2$;
Camptothecin-rvAsp-Suc-(Doc)$_4$-Aepa-D-Phe-c(Cys-Tyr-D-Trp-Lys-Abu-Cys)-Thr-NH$_2$;
Camptothecin-rvGlu-Suc-(Doc)$_4$-Aepa-D-Phe-c(Cys-Tyr-D-Trp-Lys-Abu-Cys)-Thr-NH$_2$;
Camptothecin-rvArg-Suc-(Doc)$_4$-Aepa-D-Phe-c(Cys-Tyr-D-Trp-Lys-Abu-Cys)-Thr-NH$_2$;
Camptothecin-rvDap(Z)-Suc-(Doc)$_4$-Aepa-D-Phe-c(Cys-Tyr-D-Trp-Lys-Abu-Cys)-Thr-NH$_2$;
Camptothecin-rvCha-Suc-(Doc)$_4$-Aepa-D-Phe-c(Cys-Tyr-D-Trp-Lys-Abu-Cys)-Thr-NH$_2$;
Camptothecin-rvPhe-Suc-(Doc)$_4$-Aepa-D-Phe-c(Cys-Tyr-D-Trp-Lys-Abu-Cys)-Thr-NH$_2$;
Camptothecin-rvApn-Suc-(Doc)$_4$-Aepa-D-Phe-c(Cys-Tyr-D-Trp-Lys-Abu-Cys)-Thr-NH$_2$;
Camptothecin-rvAbu-Suc-(Doc)$_4$-Aepa-D-Phe-c(Cys-Tyr-D-Trp-Lys-Abu-Cys)-Thr-NH$_2$;
Camptothecin-rvAla-Suc-(Doc)$_4$-Aepa-D-Phe-c(Cys-Tyr-D-Trp-Lys-Abu-Cys)-Thr-NH$_2$;
Camptothecin-rvVal-Suc-(Doc)$_4$-Aepa-D-Phe-c(Cys-Tyr-D-Trp-Lys-Abu-Cys)-Thr-NH$_2$;
Camptothecin-Glut-(Doc)$_4$-Aepa-D-Phe-c(Cys-Tyr-D-Trp-Lys-Abu-Cys)-Thr-NH$_2$;
Camptothecin-rvAnc-Suc-(Doc)$_4$-Aepa-D-Phe-cyclo(Cys-Tyr-D-Trp-Lys-Abu-Cys)-Thr-NH$_2$;
Camptothecin-rvAhp-Suc-(Doc)$_4$-Aepa-D-Phe-cyclo(Cys-Tyr-D-Trp-Lys-Abu-Cys)-Thr-NH$_2$; or
SN38-rvGly-Suc-(Doc)$_4$-Aepa-D-Phe-c(Cys-Tyr-D-Trp-Lys-Abu-Cys)-Thr-NH$_2$;
or a pharmaceutically acceptable salt thereof.

A fourth embodiment of the first aspect of the invention features any one of the following compounds:
Camptothecin-rvAsp-Suc-(Doc)$_4$-Aepa-D-Phe-c(Cys-Tyr-D-Trp-Lys-Abu-Cys)-Thr-NH$_2$;
Camptothecin-rvGlu-Suc-(Doc)$_4$-Aepa-D-Phe-c(Cys-Tyr-D-Trp-Lys-Abu-Cys)-Thr-NH$_2$;
Camptothecin-rvCha-Suc-(Doc)$_4$-Aepa-D-Phe-c(Cys-Tyr-D-Trp-Lys-Abu-Cys)-Thr-NH$_2$;
Camptothecin-rvAbu-Suc-(Doc)$_4$-Aepa-D-Phe-c(Cys-Tyr-D-Trp-Lys-Abu-Cys)-Thr-NH$_2$;
Camptothecin-rvAla-Suc-(Doc)$_4$-Aepa-D-Phe-c(Cys-Tyr-D-Trp-Lys-Abu-Cys)-Thr-NH$_2$;
Camptothecin-rvVal-Suc-(Doc)$_4$-Aepa-D-Phe-c(Cys-Tyr-D-Trp-Lys-Abu-Cys)-Thr-NH$_2$;
Camptothecin-rvAnc-Suc-(Doc)$_4$-Aepa-D-Phe-c(Cys-Tyr-D-Trp-Lys-Abu-Cys)-Thr-NH$_2$;
SN38-rvGly-Suc-(Doc)$_4$-Aepa-D-Phe-c(Cys-Tyr-D-Trp-Lys-Abu-Cys)-Thr-NH$_2$; or
or a pharmaceutically acceptable salt thereof.

A fifth embodiment of the first aspect of the invention features any one of the following compounds:
Camptothecin-rvAsp-Suc-(Doc)$_4$-Aepa-D-Phe-c(Cys-Tyr-D-Trp-Lys-Abu-Cys)-Thr-NH$_2$;
Camptothecin-rvGlu-Suc-(Doc)$_4$-Aepa-D-Phe-c(Cys-Tyr-D-Trp-Lys-Abu-Cys)-Thr-NH$_2$;
Camptothecin-rvCha-Suc-(Doc)$_4$-Aepa-D-Phe-c(Cys-Tyr-D-Trp-Lys-Abu-Cys)-Thr-NH$_2$;
Camptothecin-rvAbu-Suc-(Doc)$_4$-Aepa-D-Phe-c(Cys-Tyr-D-Trp-Lys-Abu-Cys)-Thr-NH;
SN38-rvGly-Suc-(Doc)$_4$-Aepa-D-Phe-c(Cys-Tyr-D-Trp-Lys-Abu-Cys)-Thr-NH$_2$; or
or a pharmaceutically acceptable salt thereof.

A sixth embodiment of the first aspect of the invention features
Camptothecin-rvAsp-Suc-(Doc)$_4$-Aepa-D-Phe-c(Cys-Tyr-D-Trp-Lys-Abu-Cys)-Thr-NH$_2$;
Camptothecin-rvCha-Suc-(Doc)$_4$-Aepa-D-Phe-c(Cys-Tyr-D-Trp-Lys-Abu-Cys)-Thr-NH$_2$;
SN38-rvGly-Suc-(Doc)$_4$-Aepa-D-Phe-c(Cys-Tyr-D-Trp-Lys-Abu-Cys)-Thr-NH$_2$; or
or a pharmaceutically acceptable salt thereof.

A seventh embodiment of the first aspect of the invention features the compound:
Camptothecin-rvAsp-Suc-(Doc)$_4$-Aepa-D-Phe-c(Cys-Tyr-D-Trp-Lys-Abu-Cys)-Thr-NH$_2$;
or a pharmaceutically acceptable salt thereof.

An eighth embodiment of the first aspect of the invention features the compound:
Camptothecin-rvCha-Suc-(Doc)$_4$-Aepa-D-Phe-c(Cys-Tyr-D-Trp-Lys-Abu-Cys)-Thr-NH$_2$;
or a pharmaceutically acceptable salt thereof.

A ninth embodiment of the first aspect of the invention features the compound:
SN38-rvGly-Suc-(Doc)$_4$-Aepa-D-Phe-c(Cys-Tyr-D-Trp-Lys-Abu-Cys)-Thr-NH$_2$; or a pharmaceutically acceptable salt thereof.

In a second aspect of the invention, the cytotoxic moiety and targeting moiety are described by Formula IB:

A-B-C-E (IB)

wherein:
A is camptothecin or a derivative thereof;
B is rvD-Abu, rvD-Ala, rvD-Arg, rvD-Asp, rvD-Cha, rvD-Dap(Z), rvD-Glu, rvD-Phe, or rvD-Val or deleted;

C is $D^1$-$D^2$-$D^3$-$D^4$ wherein $D^1$ is glutaryl, succinyl or deleted;

$D^2$ is $(Doc)_m$ wherein m is, independently for each occurrence thereof, 4, 5 or 6 or $[Peg]_x$ wherein x is, independently for each occurrence thereof, 0-100;

$D^3$ is $(Aepa)_n$ wherein n is, independently for each occurrence thereof, 0 or 1; and $D^4$ is D-Phe or Lys-D-Tyr-D-Tyr;

E is a somatostatin analog of the formula $c(Cys-A^2-A^3-D-Trp-Lys-A^6-Cys)-A^8-R$ wherein $A^2$ is Phe or deleted;

$A^3$ is Phe, 3-(I)Tyr or Tyr, $A^6$ is Abu, Thr or deleted;

$A^8$ is Thr or deleted; and

R is $NH_2$ or OH;

or a pharmaceutically acceptable salt thereof.

A first embodiment of the second aspect of the invention features compounds of Formula (IB) having a camptothecin moiety selected from the group consisting of:

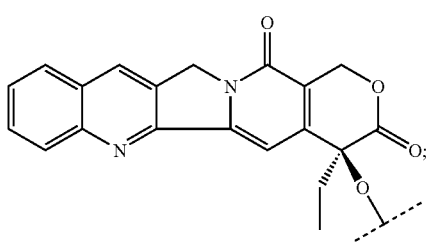

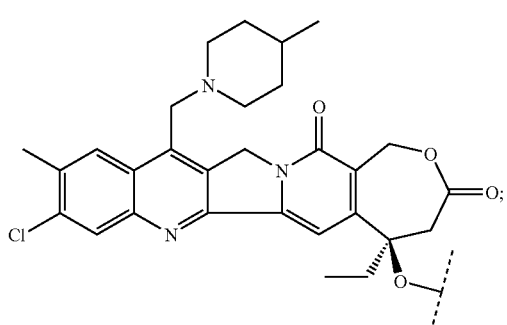

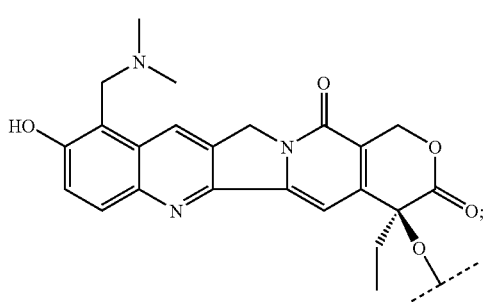

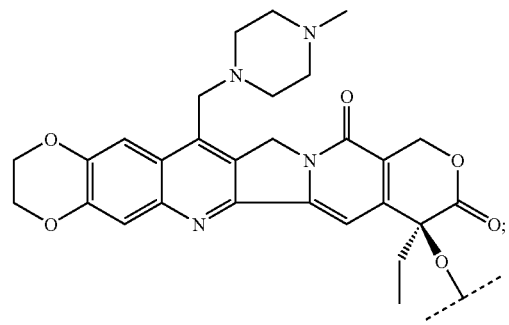

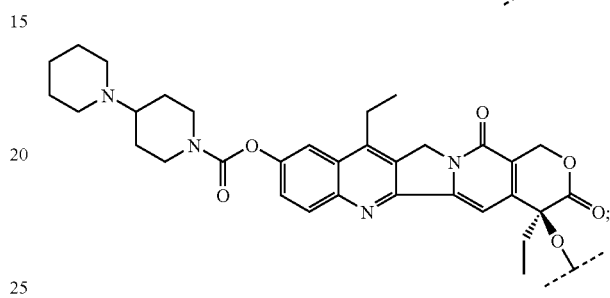

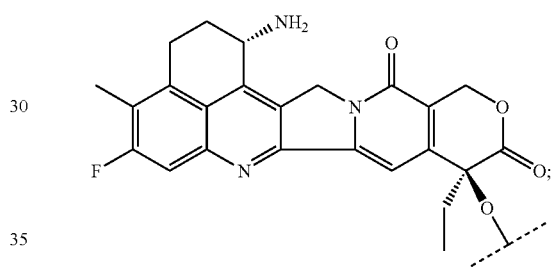

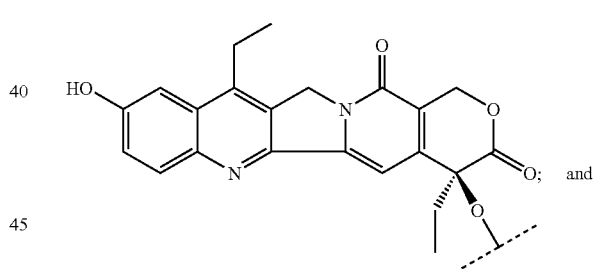

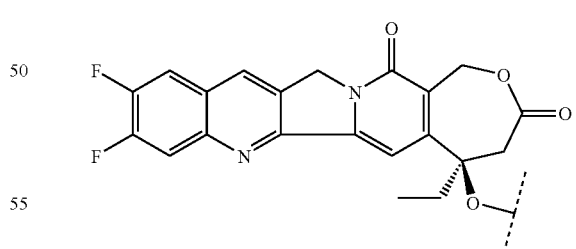

wherein the dashed line "----" in the above indicates the point of attachment of the camptothecin moiety to a second moiety, e.g., a linker or peptide.

A second embodiment of the second aspect of the invention features compounds according to Formula (IB) wherein the targeting moiety is native somatostatin or a fragment and/or analog thereof according to any one of the following formulae:

(SEQ ID NO: 1)
H-Ala-Gly-Cys-Lys-Asn-Phe-Phe-Trp-Lys-Thr-Phe-Thr-Ser-Cys-OH (Native SRIF);

c(Cys-3-(I)Tyr-D-Trp-Lys-Abu-Cys)-Thr-NH$_2$;

c(Cys-Phe-Phe-D-Trp-Lys-Thr-Cys)-NH$_2$; or c(Cys-Tyr-D-Trp-Lys-Abu-Cys)-Thr-NH$_2$ or a pharmaceutically acceptable salt thereof.

A third embodiment of the second aspect of the invention features any one of the following compounds:

Camptothecin-rvD-Asp-Suc-(Doc)$_4$-Aepa-D-Phe-c(Cys-Tyr-D-Trp-Lys-Abu-Cys)-Thr-NH$_2$;
Camptothecin-rvD-Glu-Suc-(Doc)$_4$-Aepa-D-Phe-c(Cys-Tyr-D-Trp-Lys-Abu-Cys)-Thr-NH$_2$;
Camptothecin-rvD-Arg-Suc-(Doc)$_4$-Aepa-D-Phe-c(Cys-Tyr-D-Trp-Lys-Abu-Cys)-Thr-NH$_2$;
Camptothecin-rvD-Dap(Z)-Suc-(Doc)$_4$-Aepa-D-Phe-c(Cys-Tyr-D-Trp-Lys-Abu-Cys)-Thr-NH$_2$;
Camptothecin-rvD-Cha-Suc-(Doc)$_4$-Aepa-D-Phe-c(Cys-Tyr-D-Trp-Lys-Abu-Cys)-Thr-NH$_2$;
Camptothecin-rvD-Phe-Suc-(Doc)$_4$-Aepa-D-Phe-c(Cys-Tyr-D-Trp-Lys-Abu-Cys)-Thr-NH$_2$;
Camptothecin-rvD-Abu-Suc-(Doc)$_4$-Aepa-D-Phe-c(Cys-Tyr-D-Trp-Lys-Abu-Cys)-Thr-NH$_2$;
Camptothecin-rvD-Val-Suc-(Doc)$_4$-Aepa-D-Phe-c(Cys-Tyr-D-Trp-Lys-Abu-Cys)-Thr-NH$_2$;
Camptothecin-rvD-Ala-Suc-(Doc)$_4$-Aepa-D-Phe-c(Cys-Tyr-D-Trp-Lys-Abu-Cys)-Thr-NH$_2$;
Camptothecin-rvDAsp-Suc-(Peg3)$_3$-Aepa-D-Phe-c(Cys-Tyr-D-Trp-Lys-Abu-Cys)-Thr-NH$_2$;
Camptothecin-rvDAsp-Suc-Peg$_{11}$-Aepa-DPhe-c(Cys-Tyr-DTrp-Lys-Abu-Cys)-Thr-NH$_2$; or
Camptothecin-rvDGlu-Suc-(Doc)$_4$-Aepa-DPhe-c(Cys-Tyr-DTrp-Lys-Abu-Cys)-Thr-NH$_2$;

or a pharmaceutically acceptable salt thereof.

A fourth embodiment of the second aspect of the invention features any one of the following compounds:

Camptothecin-rvD-Asp-Suc-(Doc)$_4$-Aepa-D-Phe-c(Cys-Tyr-D-Trp-Lys-Abu-Cys)-Thr-NH$_2$;
Camptothecin-rvD-Glu-Suc-(Doc)$_4$-Aepa-D-Phe-c(Cys-Tyr-D-Trp-Lys-Abu-Cys)-Thr-NH$_2$;
Camptothecin-rvD-Cha-Suc-(Doc)$_4$-Aepa-D-Phe-c(Cys-Tyr-D-Trp-Lys-Abu-Cys)-Thr-NH$_2$;
Camptothecin-rvD-Abu-Suc-(Doc)$_4$-Aepa-D-Phe-c(Cys-Tyr-D-Trp-Lys-Abu-Cys)-Thr-NH$_2$;
Camptothecin-rvD-Ala-Suc-(Doc)$_4$-Aepa-D-Phe-c(Cys-Tyr-D-Trp-Lys-Abu-Cys)-Thr-NH$_2$;
Camptothecin-rvD-Val-Suc-(Doc)$_4$-Aepa-D-Phe-c(Cys-Tyr-D-Trp-Lys-Abu-Cys)-Thr-NH$_2$;
Camptothecin-rvDAsp-Suc-(Peg3)$_3$-Aepa-DPhe-c(Cys-Tyr-DTrp-Lys-Abu-Cys)-Thr-NH$_2$;
Camptothecin-rvDAsp-Suc-Peg$_{11}$-Aepa-DPhe-c(Cys-Tyr-DTrp-Lys-Abu-Cys)-Thr-NH$_2$; or
Camptothecin-rvDGlu-Suc-(Doc)$_4$-Aepa-DPhe-c(Cys-Tyr-DTrp-Lys-Abu-Cys)-Thr-NH$_2$;

or a pharmaceutically acceptable salt thereof.

A fifth embodiment of the second aspect of the invention features any one of the following compounds:

Camptothecin-rvD-Asp-Suc-(Doc)$_4$-Aepa-D-Phe-c(Cys-Tyr-D-Trp-Lys-Abu-Cys)-Thr-NH$_2$;
Camptothecin-rvD-Glu-Suc-(Doc)$_4$-Aepa-D-Phe-c(Cys-Tyr-D-Trp-Lys-Abu-Cys)-Thr-NH$_2$;
Camptothecin-rvD-Cha-Suc-(Doc)$_4$-Aepa-D-Phe-c(Cys-Tyr-D-Trp-Lys-Abu-Cys)-Thr-NH$_2$;
Camptothecin-rvD-Abu-Suc-(Doc)$_4$-Aepa-D-Phe-c(Cys-Tyr-D-Trp-Lys-Abu-Cys)-Thr-NH$_2$;
Camptothecin-rvDAsp-Suc-(Peg3)$_3$-Aepa-DPhe-c(Cys-DTrp-Lys-Abu-Cys)-Thr-NH$_2$;
Camptothecin-rvDAsp-Suc-Peg$_{11}$-Aepa-DPhe-c(Cys-Tyr-DTrp-Lys-Abu-Cys)-Thr-NH$_2$; or
Camptothecin-rvDGlu-Suc-(Doc)$_4$-Aepa-DPhe-c(Cys-Tyr-DTrp-Lys-Abu-Cys)-Thr-NH$_2$;

or a pharmaceutically acceptable salt thereof.

A sixth embodiment of the second aspect of the invention features

Camptothecin-rvD-Asp-Suc-(Doc)$_4$-Aepa-D-Phe-c(Cys-Tyr-D-Trp-Lys-Abu-Cys)-Thr-NH$_2$;
Camptothecin-rvD-Cha-Suc-(Doc)$_4$-Aepa-D-Phe-c(Cys-Tyr-D-Trp-Lys-Abu-Cys)-Thr-NH$_2$;
Camptothecin-rvDAsp-Suc-(Peg3)$_3$-Aepa-DPhe-c(Cys-Tyr-DTrp-Lys-Abu-Cys)-Thr-NH$_2$;
Camptothecin-rvDAsp-Suc-Peg$_{11}$-Aepa-DPhe-c(Cys-Tyr-DTrp-Lys-Abu-Cys)-Thr-NH$_2$; or
Camptothecin-rvDGlu-Suc-(Doc)$_4$-Aepa-DPhe-c(Cys-Tyr-DTrp-Lys-Abu-Cys)-Thr-NH$_2$;

or a pharmaceutically acceptable salt thereof.

A seventh embodiment of the second aspect of the invention features the compound:

Camptothecin-rvD-Asp-Suc-(Doc)$_4$-Aepa-D-Phe-c(Cys-Tyr-D-Trp-Lys-Abu-Cys)-Thr-NH$_2$; or a pharmaceutically acceptable salt thereof.

An eighth embodiment of the second aspect of the invention features the compound:

Camptothecin-rvD-Cha-Suc-(Doc)$_4$-Aepa-D-Phe-c(Cys-Tyr-D-Trp-Lys-Abu-Cys)-Thr-NH$_2$; or a pharmaceutically acceptable salt thereof.

A ninth embodiment of the second aspect of the invention features the compound:

Camptothecin-rvDAsp-Suc-(Peg3)$_3$-Aepa-DPhe-c(Cys-Tyr-DTrp-Lys-Abu-Cys)-Thr-NH$_2$; or a pharmaceutically acceptable salt thereof.

A tenth embodiment of the second aspect of the invention features the compound:

Camptothecin-rvDAsp-Suc-Peg$_{11}$-Aepa-DPhe-c(Cys-Tyr-DTrp-Lys-Abu-Cys)-Thr-NH$_2$;

or a pharmaceutically acceptable salt thereof.

An eleventh embodiment of the second aspect of the invention features the compound:

Camptothecin-rvDGlu-Suc-(Doc)$_4$-Aepa-DPhe-c(Cys-Tyr-DTrp-Lys-Abu-Cys)-Thr-NH$_2$; or a pharmaceutically acceptable salt thereof.

The compounds according to Formulae IA and IB of the invention are featured as substantially pure compounds. Substantially pure compounds are compounds which are determined to contain approximately 98% or greater of identical molecules according to Formulae IA or IB with approximately 2% or less of non-identical molecules, i.e., impurities, partially completed molecules, intermediate molecules or enantiomeric forms. Of course, substantially pure compounds include those compounds containing approximately 99%, 99.5%, 99.8% or 99.9% or greater of identical molecules with approximately 1%, 0.5%, 0.2%, or 0.1% or less of non-identical molecules. Substantially pure compounds are also contemplated to include those compounds containing 100% identical molecules.

In a third aspect, the invention features a mixture of compounds of Formulae IA and IB wherein the rv amino acid linker occurs in the D form (Formula IB) in some compounds in the mixture and in the L form (Formula IA) in some compounds in the mixture. The mixture comprises, weight/weight, about 2:98, about 5:95, about 10:90, about 15:85, about 20:80, about 25:75, about 30:70, about 35:65, about 40:60, about 45:50, about 50:50, about 55:45, about 60:40, about 65:25, about 70:30, about 75:25, about 80:20, about 85:15, about 90:10, about 95:5, about 97:3 or even about 98:2 compounds in the mixture wherein the rv amino acid linker occurs in the D form (Formula IB) and in the L form (Formula IA), respectively. Exemplary mixtures include, but are not limited to, mixtures of compounds Camptothecin-rvD-Asp-Suc-(Doc)$_4$-Aepa-D-Phe-c(Cys-Tyr-D-Trp-Lys-Abu-Cys)-Thr-NH$_2$ and Camptothecin-rvAsp-Suc-(Doc)$_4$-Aepa-D-Phe-c(Cys-Tyr-D-Trp-Lys-Abu-Cys)-Thr-NH$_2$ or a pharmaceutically acceptable salt of each thereof, or Camptothecin-rvD-Glu-Suc-(Doc)$_4$-Aepa-D-Phe-c(Cys-Tyr-D-Trp-Lys-Abu-Cys)-Thr-NH$_2$ and Camptothecin-rvGlu-Suc-(Doc)$_4$-Aepa-D-Phe-c(Cys-Tyr-D-Trp-Lys-Abu-Cys)-Thr-NH$_2$ or a pharmaceutically acceptable salt of each thereof.

The compounds according to Formulae IA and IB of the third aspect of the invention are featured as substantially pure compounds within the mixture. Substantially pure compounds are compounds which are determined to contain approximately 98% or greater of identical molecules according to Formulae IA or IB with approximately 2% or less of non-identical molecules, i.e., impurities, partially completed molecules, intermediate molecules or enantiomeric forms. Of course, substantially pure compounds include those compounds containing approximately 99%, 99.5%, 99.8% or 99.9% or greater of identical molecules with approximately 1%, 0.5%, 0.2%, or 0.1% or less of non-identical molecules. Substantially pure compounds are also contemplated to include those compounds containing 100% identical molecules.

In a first embodiment of the third aspect of the invention, the mixture comprises Camptothecin-rvD-Asp-Suc-(Doc)$_4$-Aepa-D-Phe-c(Cys-Tyr-D-Trp-Lys-Abu-Cys)-Thr-NH$_2$ and Camptothecin-rvAsp-Suc-(Doc)$_4$-Aepa-D-Phe-c(Cys-Tyr-D-Trp-Lys-Abu-Cys)-Thr-NH$_2$ or a pharmaceutically acceptable salt of each thereof. In one aspect of the first embodiment of the third aspect of the invention, the mixture comprises, by weight percentage, about 44:56, about 58:42, about 87:13, about 88:12, about 97:3, or about 98:2 of Camptothecin-rvD-Asp-Suc-(Doc)$_4$-Aepa-D-Phe-c(Cys-Tyr-D-Trp-Lys-Abu-Cys)-Thr-NH$_2$ to Camptothecin-rvAsp-Suc-(Doc)$_4$-Aepa-D-Phe-c(Cys-Tyr-D-Trp-Lys-Abu-Cys)-Thr-NH$_2$ or a pharmaceutically acceptable salt of each thereof, respectively.

In yet another aspect, the mixture comprises, weight/weight, about 44:56 of Camptothecin-rvD-Asp-Suc-(Doc)$_4$-Aepa-D-Phe-c(Cys-Tyr-D-Trp-Lys-Abu-Cys)-Thr-NH$_2$ to Camptothecin-rvAsp-Suc-(Doc)$_4$-Aepa-D-Phe-c(Cys-Tyr-D-Trp-Lys-Abu-Cys)-Thr-NH$_2$ or a pharmaceutically acceptable salt of each thereof, respectively. In yet another aspect, the mixture comprises, weight/weight, about 58:42 of Camptothecin-rvD-Asp-Suc-(Doc)$_4$-Aepa-D-Phe-c(Cys-Tyr-D-Trp-Lys-Abu-Cys)-Thr-NH$_2$ to Camptothecin-rvAsp-Suc-(Doc)$_4$-Aepa-D-Phe-c(Cys-Tyr-D-Trp-Lys-Abu-Cys)-Thr-NH$_2$ or a pharmaceutically acceptable salt of each thereof, respectively. In yet another aspect, the mixture comprises, weight/weight, about 87:13 of Camptothecin-rvD-Asp-Suc-(Doc)$_4$-Aepa-D-Phe-c(Cys-Tyr-D-Trp-Lys-Abu-Cys)-Thr-NH$_2$ to Camptothecin-rvAsp-Suc-(Doc)$_4$-Aepa-D-Phe-c(Cys-Tyr-D-Trp-Lys-Abu-Cys)-Thr-NH$_2$ or a pharmaceutically acceptable salt of each thereof, respectively. In yet another aspect, the mixture comprises, weight/weight, about 88:12 of Camptothecin-rvD-Asp-Suc-(Doc)$_4$-Aepa-D-Phe-c(Cys-Tyr-D-Trp-Lys-Abu-Cys)-Thr-NH$_2$ to Camptothecin-rvAsp-Suc-(Doc)$_4$-Aepa-D-Phe-c(Cys-Tyr-D-Trp-Lys-Abu-Cys)-Thr-NH$_2$ or a pharmaceutically acceptable salt of each thereof, respectively. In yet another aspect, the mixture comprises, weight/weight, about 97:3 of Camptothecin-rvD-Asp-Suc-(Doc)$_4$-Aepa-D-Phe-c(Cys-Tyr-D-Trp-Lys-Abu-Cys)-Thr-NH$_2$ to Camptothecin-rvAsp-Suc-(Doc)$_4$-Aepa-D-Phe-c(Cys-Tyr-D-Trp-Lys-Abu-Cys)-Thr-NH$_2$ or a pharmaceutically acceptable salt of each thereof, respectively. In yet another aspect, the mixture comprises, weight/weight, about 98:2 of Camptothecin-rvD-Asp-Suc-(Doc)$_4$-Aepa-D-Phe-c(Cys-Tyr-D-Trp-Lys-Abu-Cys)-Thr-NH$_2$ to Camptothecin-rvAsp-Suc-(Doc)$_4$-Aepa-D-Phe-c(Cys-Tyr-D-Trp-Lys-Abu-Cys)-Thr-NH$_2$ a or a pharmaceutically acceptable salt of each thereof, respectively.

In a second embodiment of the third aspect of the invention, the mixture comprises, weight/weight, Camptothecin-rvD-Glu-Suc-(Doc)$_4$-Aepa-D-Phe-c(Cys-Tyr-D-Trp-Lys-Abu-Cys)-Thr-NH$_2$ and Camptothecin-rvGlu-Suc-(Doc)$_4$-Aepa-D-Phe-c(Cys-Tyr-D-Trp-Lys-Abu-Cys)-Thr-NH$_2$ or a pharmaceutically acceptable salt of each thereof. In yet another aspect, the mixture comprises, weight/weight, about 80:20, about 85:15, about 87:13, about 88:12, about 90:10, about 95:5, about 97:3, about 98:2 or about 98:2 of Camptothecin-rvD-Glu-Suc-(Doc)$_4$-Aepa-D-Phe-c(Cys-Tyr-D-Trp-Lys-Abu-Cys)-Thr-NH$_2$ and Camptothecin-rvGlu-Suc-(Doc)$_4$-Aepa-D-Phe-c(Cys-Tyr-D-Trp-Lys-Abu-Cys)-Thr-NH$_2$ or a pharmaceutically acceptable salt of each thereof, respectively. In yet another aspect, the mixture comprises, weight/weight, about 80:20 of Camptothecin-rvD-Glu-Suc-(Doc)$_4$-Aepa-D-Phe-c(Cys-Tyr-D-Trp-Lys-Abu-Cys)-Thr-NH$_2$ and Camptothecin-rvGlu-Suc-(Doc)$_4$-Aepa-D-Phe-c(Cys-Tyr-D-Trp-Lys-Abu-Cys)-Thr-NH$_2$ or a pharmaceutically acceptable salt of each thereof, respectively. In yet another aspect, the mixture comprises, weight/weight, about 85:15 of Camptothecin-rvD-Glu-Suc-(Doc)$_4$-Aepa-D-Phe-c(Cys-Tyr-D-Trp-Lys-Abu-Cys)-Thr-NH$_2$ and Camptothecin-rvGlu-Suc-(Doc)$_4$-Aepa-D-Phe-c(Cys-Tyr-D-Trp-Lys-Abu-Cys)-Thr-NH$_2$ or a pharmaceutically acceptable salt of each thereof, respectively. In yet another aspect, the mixture comprises, weight/weight, about 87:13 of Camptothecin-rvD-Glu-Suc-(Doc)$_4$-Aepa-D-Phe-c(Cys-Tyr-D-Trp-Lys-Abu-Cys)-Thr-NH$_2$ and Camptothecin-rvGlu-Suc-(Doc)$_4$-Aepa-D-Phe-c(Cys-Tyr-D-Trp-Lys-Abu-Cys)-Thr-NH$_2$ or a pharmaceutically acceptable salt of each thereof, respectively. In yet another aspect, the mixture comprises, weight/weight, about 88:12 of Camptothecin-rvD-Glu-Suc-(Doc)$_4$-Aepa-D-Phe-c(Cys-Tyr-D-Trp-Lys-Abu-Cys)-Thr-NH$_2$ and Camptothecin-rvGlu-Suc-(Doc)$_4$-Aepa-D-Phe-c(Cys-Tyr-D-Trp-Lys-Abu-Cys)-Thr-NH$_2$ or a pharmaceutically acceptable salt of each thereof, respectively. In yet another aspect, the mixture comprises, weight/weight about 90:10 of Camptothecin-rvD-Glu-Suc-(Doc)$_4$-Aepa-D-Phe-c(Cys-Tyr-D-Trp-Lys-Abu-Cys)-Thr-NH$_2$ and Camptothecin-rvGlu-Suc-(Doc)$_4$-Aepa-D-Phe-c(Cys-Tyr-D-Trp-Lys-Abu-Cys)-Thr-NH$_2$ or a pharmaceutically acceptable salt of each thereof, respectively. In yet another aspect, the mixture comprises, weight/weight, about 95:5 of Camptothecin-rvD-Glu-Suc-(Doc)$_4$-Aepa-D-Phe-c(Cys-Tyr-D-Trp-Lys-Abu-Cys)-Thr-NH$_2$ and Camptothecin-rvGlu-Suc-(Doc)$_4$-Aepa-D-Phe-c(Cys-Tyr-D-Trp-Lys-Abu-Cys)-Thr-NH$_2$ or a pharmaceutically acceptable salt of each thereof, respectively. In yet another aspect, the mixture comprises, weight/weight, about 97:3 of Camptothecin-rvD-Glu-Suc-(Doc)$_4$-Aepa-D-Phe-c(Cys-Tyr-D-Trp-Lys-Abu-Cys)-Thr-NH$_2$ and Camptothecin-rvGlu-Suc-(Doc)$_4$-Aepa-D-Phe-c(Cys-Tyr-D-Trp-Lys-Abu-Cys)-Thr-NH$_2$ or a pharmaceutically acceptable salt of each thereof, respectively. In yet another aspect, the mixture comprises, weight/weight, about 98:2 of Camptothecin-rvD-Glu-Suc-(Doc)$_4$-Aepa-D-Phe-c(Cys-Tyr-D-Trp-Lys-Abu-Cys)-Thr-NH$_2$ and Camptothecin-rvGlu-Suc-(Doc)$_4$-Aepa-D-Phe-c(Cys-Tyr-D-Trp-Lys-Abu-Cys)-Thr-NH$_2$ or a pharmaceutically acceptable salt of each thereof, respectively.

In a fourth aspect, the invention features a pharmaceutical composition comprising a therapeutically effective amount of a substantially pure compound of Formula (IA), a substantially pure compound of Formula (IB) or a mixture of substantially pure compounds of Formulae (IA) and (IB) according to any one of the aforementioned embodiments, or a pharmaceutically acceptable salt thereof and a pharmaceutically acceptable carrier.

In a fifth aspect, the invention features a method of treating a disease or condition in a subject in need thereof comprising administering a therapeutically effective amount of a substantially pure compound of Formula (IA), a substantially pure compound of Formula (IB) or a mixture of substantially pure compounds of Formulae (IA) and (IB) according to any one of the aforementioned embodiments, a pharmaceutically acceptable salt thereof, or a pharmaceutical composition as described above, wherein the disease or condition is characterized by undesired proliferation of cells that express one or more somatostatin-receptors. In another embodiment, the somatostatin receptor is a type-2 somatostatin receptor.

In a sixth aspect, the invention features a method of decreasing tumor size in a subject in need thereof comprising administering a therapeutically effective amount of a substantially pure compound of Formula (IA), a substantially pure compound of Formula (IB) or a mixture of substantially pure compounds of Formulae (IA) and (IB) according to any one of the aforementioned embodiments, a pharmaceutically acceptable salt thereof, or a pharmaceutical composition as described above, wherein the therapeutically effective amount is that amount which decreases the size of the tumor in the subject or a pharmaceutical composition thereof.

In a seventh aspect, the invention features a method of inhibiting the undesired proliferation of tumor cells in a subject in need thereof comprising patient comprising administering a therapeutically effective amount of a substantially pure compound of Formula (IA), a substantially pure compound of Formula (IB) or a mixture of substantially pure compounds of Formulae (IA) and (IB) according to any one of the aforementioned embodiments, a pharmaceutically acceptable salt thereof, or a pharmaceutical composition as described above, wherein the therapeutically effective amount is that amount which inhibits the undesired proliferation of the tumor cells in the subject or a pharmaceutical composition thereof.

In an eighth aspect, the invention features a method of eliciting an agonist effect at a somatostatin receptor in a subject in need thereof comprising administering a therapeutically effective amount of a substantially pure compound of Formula (IA), a substantially pure compound of Formula (IB) or a mixture of substantially pure compounds of Formulae (IA) and (IB) according to any one of the aforementioned embodiments, a pharmaceutically acceptable salt thereof, or a pharmaceutical composition as described above, wherein the therapeutically effective amount is that amount which elicits an agonist effect at a somatostatin receptor.

In a ninth aspect, the invention features a method of eliciting an agonist effect at a somatostatin receptor in a subject in need thereof comprising administering a therapeutically effective amount of a substantially pure compound of Formula (IA), a substantially pure compound of Formula (IB) or a mixture of substantially pure compounds of Formulae (IA) and (IB) according to any one of the aforementioned embodiments, a pharmaceutically acceptable salt thereof, or a pharmaceutical composition as described above, wherein the receptor is an SSTR type-2 receptor and the agonist is an SSTR type-2 agonist.

In a tenth aspect, the invention features a method of eliciting an agonist effect at a somatostatin receptor in a subject in need thereof comprising administering a therapeutically effective amount of a substantially pure compound of Formula (IA), a substantially pure compound of Formula (IB) or a mixture of substantially pure compounds of Formulae (IA) and (IB) according to any one of the aforementioned embodiments, a pharmaceutically acceptable salt thereof, or a pharmaceutical composition as described above, wherein the agonist is an SSTR type-2 selective agonist.

In an eleventh aspect, the invention features a method of eliciting an agonist effect at a somatostatin receptor in a subject in need thereof comprising administering a therapeutically effective amount of Camptothecin-rvAsp-Suc-(Doc)$_4$-Aepa-D-Phe-c(Cys-Tyr-D-Trp-Lys-Abu-Cys)-Thr-NH$_2$, a pharmaceutically acceptable salt thereof, or a pharmaceutical composition as described above.

In a twelfth aspect, the invention features a method of eliciting an agonist effect at a somatostatin receptor in a subject in need thereof comprising administering a therapeutically effective amount of Camptothecin-rvCha-Suc-(Doc)$_4$-Aepa-D-Phe-c(Cys-Tyr-D-Trp-Lys-Abu-Cys)-Thr-NH$_2$, a pharmaceutically acceptable salt thereof, or a pharmaceutical composition as described above.

In a thirteenth aspect, the invention features a method of eliciting an agonist effect at a somatostatin receptor in a subject in need thereof comprising administering a therapeutically effective amount of SN38-rvGly-Suc-(Doc)$_4$-Aepa-D-Phe-c(Cys-Tyr-D-Trp-Lys-Abu-Cys)-Thr-NH$_2$, a pharmaceutically acceptable salt thereof, or a pharmaceutical composition as described above.

In a fourteenth aspect, the invention features a method of eliciting an agonist effect at a somatostatin receptor in a subject in need thereof comprising administering a therapeutically effective amount of Camptothecin-rvD-Asp-Suc-(Doc)$_4$-Aepa-D-Phe-c(Cys-Tyr-D-Trp-Lys-Abu-Cys)-Thr-NH$_2$, a pharmaceutically acceptable salt thereof, or a pharmaceutical composition as described above.

In a fifteenth aspect, the invention features a method of eliciting an agonist effect at a somatostatin receptor in a subject in need thereof comprising administering a therapeutically effective amount of Camptothecin-rvD-Cha-Suc-(Doc)$_4$-Aepa-D-Phe-c(Cys-Tyr-D-Trp-Lys-Abu-Cys)-Thr-NH$_2$, a pharmaceutically acceptable salt thereof, or a pharmaceutical composition as described above.

In a sixteenth aspect, the invention features a method of eliciting an agonist effect at a somatostatin receptor in a subject in need thereof comprising administering a therapeutically effective amount of a mixture comprising Camptothecin-rvD-Asp-Suc-(Doc)$_4$-Aepa-D-Phe-c(Cys-Tyr-D-Trp-Lys-Abu-Cys)-Thr-NH$_2$ and Camptothecin-rvAsp-Suc-(Doc)$_4$-Aepa-D-Phe-c(Cys-Tyr-D-Trp-Lys-Abu-Cys)-Thr-NH$_2$, a pharmaceutically acceptable salt of each thereof, or a pharmaceutical composition as described above.

In a seventeenth aspect, the invention features a method of eliciting an agonist effect at a somatostatin receptor in a subject in need thereof comprising administering a therapeutically effective amount of a mixture comprising Camptothecin-rvD-Glu-Suc-(Doc)$_4$-Aepa-D-Phe-c(Cys-Tyr-D-Trp-Lys-Abu-Cys)-Thr-NH$_2$ and Camptothecin-rvGlu-Suc-(Doc)$_4$-Aepa-D-Phe-c(Cys-Tyr-D-Trp-Lys-Abu-Cys)-Thr- NH$_2$, a pharmaceutically acceptable salt of each thereof, or a pharmaceutical composition as described above.

In an eighteenth aspect, the invention features a method of eliciting an agonist effect at a somatostatin receptor in a subject in need thereof comprising administering a therapeutically effective amount of Camptothecin-rvDAsp-Suc-(Peg3)$_3$-Aepa-DPhe-c(Cys-Tyr-DTrp-Lys-Abu-Cys)-Thr-NH$_2$, a pharmaceutically acceptable salt thereof, or a pharmaceutical composition as described above.

In a nineteenth aspect, the invention features a method of eliciting an agonist effect at a somatostatin receptor in a subject in need thereof comprising administering a therapeutically effective amount of Camptothecin-rvDAsp-Suc-Peg$_{11}$-Aepa-DPhe-c(Cys-Tyr-DTrp-Lys-Abu-Cys)-Thr-NH$_2$, a pharmaceutically acceptable salt thereof, or a pharmaceutical composition as described above.

In a twentieth aspect, the invention features a method of eliciting an agonist effect at a somatostatin receptor in a subject in need thereof comprising administering a therapeutically effective amount of Camptothecin-rvDGlu-Suc-(Doc)$_4$-Aepa-DPhe-c(Cys-Tyr-DTrp-Lys-Abu-Cys)-Thr-NH$_2$, a pharmaceutically acceptable salt thereof, or a pharmaceutical composition as described above.

In a twenty-first aspect, the invention features a method of treating a disease or condition in a subject in need thereof, the method comprising administering a therapeutically effective amount of a substantially pure compound of Formula (IA), a substantially pure compound of Formula (IB) or a mixture of substantially pure compounds of Formulae (IA) and (IB) according to any one of the aforementioned embodiments, a pharmaceutically acceptable salt thereof, or a pharmaceutical composition as described above, wherein the disease or condition is characterized by undesired proliferation of cells that express one or more somatostatin-type receptors, such as tumor or cancer cells. Exemplary diseases or conditions include, but are not limited to, neuroendocrine tumors, fibrosis, benign prostatic hyperplasia, atherosclerosis, restenosis, breast cancer, colon cancer, pancreas cancer, prostate cancer, lung cancer, small cell lung cancer, ovarian cancer, epidermal cancer, non-Hodgkin's lymphoma, Hodgkin's lymphoma, leukemia, and hematopoietic cancer. The cytotoxic peptide conjugates of the instant application may also be used to treat adrenal medullary tumors (pheochromocytoma, neuroblastoma, ganglioneuroma), gastroenteropancreatic (GEP) tumors (glucagonoma, vasoactiveintestinal polypeptide secreting tumor (VIPoma), non-functioning GEP tumors), paraganglioma, pituitary ademona, astrocytomas, benign and malignant bone tumors, differentiated thyroid carcinoma (papillary, follicular, Hurthle cell), meningioma, and non-small cell lung cancer. In another aspect, the tumor or cancer is breast cancer. In yet another aspect, the tumor or cancer is small cell lung cancer. In yet another aspect, the tumor or cancer is prostate cancer. The cytotoxic peptide conjugates of the instant application may also be used to treat angiogenic and/or proliferative conditions associated with the formation of nascent blood vessels which include, but are not limited to, angiogenesis, proliferative diabetic retinopathy, cystic macular odema, rheumatoid arthritis, endometriosis, restenosis and psoriasis. Additional conditions or diseases benefiting from application of the compounds of the invention include but are not limited to autoimmune diseases (Graves' disease, Graves' opthalmopathy), bacterial pneumonia, cerebrovascular accident, fibrous dysplasia, granulomas (tuberculosis, sarcoid) and radiation pneumonitis.

In a first embodiment of the twenty-first aspect, the invention features a method of treating a disease or condition in a subject in need thereof, the method comprising administering to the subject a therapeutically effective amount of a compound of the formula Camptothecin-rvAsp-Suc-(Doc)$_4$-Aepa-D-Phe-c(Cys-Tyr-D-Trp-Lys-Abu-Cys)-Thr-NH$_2$, a pharmaceutically acceptable salt thereof, or a pharmaceutical composition as described above, wherein the disease or condition is characterized by undesired proliferation of cells that express one or more somatostatin-type receptors such as tumor or cancer cells. Exemplary diseases or conditions include, but are not limited to, neuroendocrine tumors, fibrosis, benign prostatic hyperplasia, atherosclerosis, restenosis, breast cancer, colon cancer, pancreas cancer, prostate cancer, lung cancer, small cell lung cancer, ovarian cancer, epidermal cancer, non-Hodgkin's lymphoma, Hodgkin's lymphoma, leukemia, and hematopoietic cancer. Camptothecin-rvAsp-Suc-(Doc)$_4$-Aepa-D-Phe-c(Cys-Tyr-D-Trp-Lys-Abu-Cys)-Thr-NH$_2$, a pharmaceutically acceptable salt thereof, or a pharmaceutical composition as described above may also be used to treat adrenal medullary tumors (pheochromocytoma, neuroblastoma, ganglioneuroma), gastroenteropancreatic (GEP) tumors (glucagonoma, vasoactiveintestinal polypeptide secreting tumor (VIPoma), non-functioning GEP tumors), paraganglioma, pituitary ademona, astrocytomas, benign and malignant bone tumors, differentiated thyroid carcinoma (papillary, follicular, Hurthle cell), meningioma, non-small cell lung cancer and the like. In another aspect, the tumor or cancer is breast cancer. In yet another aspect, the tumor or cancer is small cell lung cancer. In yet another aspect, the tumor or cancer is prostate cancer. In addition, Camptothecin-rvAsp-Suc-(Doc)$_4$-Aepa-D-Phe-c(Cys-Tyr-D-Trp-Lys-Abu-Cys)-Thr-NH$_2$, a pharmaceutically acceptable salt thereof, or a pharmaceutical composition as described previously, may also be used to treat angiogenic and/or proliferative conditions associated with the formation of nascent blood vessels which include, but are not limited to, angiogenesis, proliferative diabetic retinopathy, cystic macular odema, rheumatoid arthritis, endometriosis, restenosis and psoriasis. Additional conditions or diseases benefiting from application of Camptothecin-rvAsp-Suc-(Doc)$_4$-Aepa-D-Phe-c(Cys-Tyr-D-Trp-Lys-Abu-Cys)-Thr-NH$_2$, a pharmaceutically acceptable salt thereof, or a pharmaceutical composition as described above include but are not limited to, autoimmune diseases (Graves' disease, Graves' opthalmopathy), bacterial pneumonia, cerebrovascular accident, fibrous dysplasia, granulomas (tuberculosis, sarcoid) and radiation pneumonitis.

In a second embodiment of the twenty-first aspect, the invention features a method of treating a disease or condition in a subject in need thereof, the method comprising administering to the subject a therapeutically effective amount is Camptothecin-rvCha-Suc-(Doc)$_4$-Aepa-D-Phe-c(Cys-Tyr-D-Trp-Lys-Abu-Cys)-Thr-NH$_2$, a pharmaceutically acceptable salt thereof, or a pharmaceutical composition described above, wherein the disease or condition is characterized by undesired proliferation of cells that express one or more somatostatin-type receptors, such as tumor or cancer cells. Exemplary diseases or conditions include, but are not limited to, neuroendocrine tumors, fibrosis, benign prostatic hyperplasia, atherosclerosis, restenosis, breast cancer, colon cancer, pancreas cancer, prostate cancer, lung cancer, small cell lung cancer, ovarian cancer, epidermal cancer, non-Hodgkin's lymphoma, Hodgkin's lymphoma, leukemia, and hematopoietic cancer. Camptothecin-rvCha-Suc-(Doc)$_4$-Aepa-D-Phe-c(Cys-Tyr-D-Trp-Lys-Abu-Cys)-Thr-NH$_2$, a pharmaceutically acceptable salt thereof, or a pharmaceutical composition described above may also be used to treat adrenal medullary tumors (pheochromocytoma, neuroblastoma, ganglioneuroma), gastroenteropancreatic (GEP) tumors (glucagonoma, vasoactiveintestinal polypeptide secreting tumor (VIPoma), non-functioning GEP tumors), paraganglioma, pituitary ademona, astrocytomas, benign and malignant bone tumors, differentiated thyroid carcinoma (papillary, follicular, Hurthle cell), meningioma, non-small cell lung cancer and the like. In another aspect, the tumor or cancer is breast cancer. In yet another aspect, the tumor or cancer is small cell lung cancer. In yet another aspect, the tumor or cancer is prostate cancer. In addition, Camptothecin-rvCha-Suc-(Doc)$_4$-Aepa-D-Phe-c(Cys-Tyr-D-Trp-Lys-Abu-Cys)-Thr-NH$_2$, a pharmaceutically acceptable salt thereof, or a pharmaceutical composition as described previously, may also be used to treat angiogenic and/or proliferative conditions associated with the formation of nascent blood vessels which include, but are not limited to, angiogenesis, proliferative diabetic retinopathy, cystic macular odema, rheumatoid arthritis, endometriosis, restenosis and psoriasis. Additional conditions or diseases benefiting from application of Camptothecin-rvCha-Suc-(Doc)$_4$-Aepa-D-Phe-c(Cys-Tyr-D-Trp-Lys-Abu-Cys)-Thr-NH$_2$, a pharmaceutically acceptable salt thereof, or a pharmaceutical composition described above include, but are not limited to, autoimmune diseases (Graves' disease, Graves' opthalmopathy), bacterial pneumonia, cerebrovascular accident, fibrous dysplasia, granulomas (tuberculosis, sarcoid) and radiation pneumonitis.

In a third embodiment of the twenty-first aspect, the invention features a method of treating a disease or condition in a subject in need thereof, the method comprising administering to the subject a therapeutically effective amount of a compound of the formula: SN38-rvGly-Suc-(Doc)$_4$-Aepa-D-Phe-c(Cys-Tyr-D-Trp-Lys-Abu-Cys)-Thr-NH$_2$, a pharmaceutically acceptable salt thereof, or a pharmaceutical composition thereof, wherein the disease or condition is characterized by undesired proliferation of cells that express one or more somatostatin-type receptors, such as tumor or cancer cells. Exemplary diseases or conditions include, but are not limited to, neuroendocrine tumors, fibrosis, benign prostatic hyperplasia, atherosclerosis, restenosis, breast cancer, colon cancer, pancreas cancer, prostate cancer, lung cancer, small cell lung cancer, ovarian cancer, epidermal cancer, non-Hodgkin's lymphoma, Hodgkin's lymphoma, leukemia, and hematopoietic cancer. SN38-rvGly-Suc-(Doc)$_4$-Aepa-D-Phe-c(Cys-Tyr-D-Trp-Lys-Abu-Cys)-Thr-NH$_2$, a pharmaceutically acceptable salt thereof, or a pharmaceutical composition thereof may also be used to treat adrenal medullary tumors (pheochromocytoma, neuroblastoma, ganglioneuroma), gastroenteropancreatic (GEP) tumors (glucagonoma, vasoactiveintestinal polypeptide secreting tumor (VIPoma), non-functioning GEP tumors), paraganglioma, pituitary ademona, astrocytomas, benign and malignant bone tumors, differentiated thyroid carcinoma (papillary, follicular, Hurthle cell), meningioma, non-small cell lung cancer and the like. In another aspect, the tumor or cancer is breast cancer. In yet another aspect, the tumor or cancer is small cell lung cancer. In yet another aspect, the tumor or cancer is prostate cancer. In addition, SN38-rvGly-Suc-(Doc)$_4$-Aepa-D-Phe-c(Cys-Tyr-D-Trp-Lys-Abu-Cys)-Thr-NH$_2$, a pharmaceutically acceptable salt thereof, or a pharmaceutical composition as described previously, may also be used to treat angiogenic and/or proliferative conditions associated with the formation of nascent blood vessels which include, but are not limited to, angiogenesis, proliferative diabetic retinopathy, cystic macular odema, rheumatoid arthritis, endometriosis, restenosis and psoriasis. Additional conditions or diseases benefiting from application of SN38-rvGly-Suc-(Doc)$_4$-Aepa-D-Phe-c(Cys-Tyr-D-Trp-Lys-Abu-Cys)-Thr-NH$_2$, a pharmaceutically acceptable salt thereof, or a pharmaceutical composition thereof include, but are not limited to, autoimmune diseases (Graves' disease, Graves' opthalmopathy), bacterial pneumonia, cerebrovascular accident, fibrous dysplasia, granulomas (tuberculosis, sarcoid) and radiation pneumonitis.

In a fourth embodiment of the twenty-first aspect, the invention features a method of treating a disease or condition in a subject in need thereof, the method comprising administering to the subject a therapeutically effective amount of a compound of the formula Camptothecin-rvD-Asp-Suc-(Doc)$_4$-Aepa-D-Phe-c(Cys-Tyr-D-Trp-Lys-Abu-Cys)-Thr-NH$_2$, a pharmaceutically acceptable salt thereof, or a pharmaceutical composition as described above, wherein the disease or condition is characterized by undesired proliferation of cells that express one or more somatostatin-type receptors such as tumor or cancer cells. Exemplary diseases or conditions include, but are not limited to, neuroendocrine tumors, fibrosis, benign prostatic hyperplasia, atherosclerosis, restenosis, breast cancer, colon cancer, pancreas cancer, prostate cancer, lung cancer, small cell lung cancer, ovarian cancer, epidermal cancer, non-Hodgkin's lymphoma, Hodgkin's lymphoma, leukemia, and hematopoietic cancer. Camptothecin-rvD-Asp-Suc-(Doc)$_4$-Aepa-D-Phe-c(Cys-Tyr-D-Trp-Lys-Abu-Cys)-Thr-NH$_2$, a pharmaceutically acceptable salt thereof, or a pharmaceutical composition as described above may also be used to treat adrenal medullary tumors (pheochromocytoma, neuroblastoma, ganglioneuroma), gastroenteropancreatic (GEP) tumors (glucagonoma, vasoactiveintestinal polypeptide secreting tumor (VIPoma), non-functioning GEP tumors), paraganglioma, pituitary ademona, astrocytomas, benign and malignant bone tumors, differentiated thyroid carcinoma (papillary, follicular, Hurthle cell), meningioma, non-small cell lung cancer and the like. In another aspect, the tumor or cancer is breast cancer. In yet another aspect, the tumor or cancer is small cell lung cancer. In yet another aspect, the tumor or cancer is prostate cancer. In addition, camptothecin-rvD-Asp-Suc-(Doc)$_4$-Aepa-D-Phe-c(Cys-Tyr-D-Trp-Lys-Abu-Cys)-Thr-NH$_2$, a pharmaceutically acceptable salt thereof, or a pharmaceutical composition as described previously, may also be used to treat angiogenic and/or proliferative conditions associated with the formation of nascent blood vessels which include, but are not limited to, angiogenesis, proliferative diabetic retinopathy, cystic macular odema, rheumatoid arthritis, endometriosis, restenosis and psoriasis. Additional conditions or diseases benefiting from application of Camptothecin-rvD-Asp-Suc-(Doc)$_4$-Aepa-D-Phe-c(Cys-Tyr-D-Trp-Lys-Abu-Cys)-Thr-NH$_2$, a pharmaceutically acceptable salt thereof, or a pharmaceutical composition as described above include, but are not limited to, autoimmune diseases (Graves' disease, Graves' opthalmopathy), bacterial pneumonia, cerebrovascular accident, fibrous dysplasia, granulomas (tuberculosis, sarcoid) and radiation pneumonitis.

In a fifth embodiment of the twenty-first aspect, the invention features a method of treating a disease or condition in a subject in need thereof, the method comprising administering to the subject a therapeutically effective amount is Camptothecin-rvD-Cha-Suc-(Doc)$_4$-Aepa-D-Phe-c(Cys-Tyr-D-Trp-Lys-Abu-Cys)-Thr-NH$_2$, a pharmaceutically acceptable salt thereof, or a pharmaceutical composition described above, wherein the disease or condition is characterized by undesired proliferation of cells that express one or more somatostatin-type receptors, such as tumor or cancer cells. Exemplary diseases or conditions include, but are not limited to, neuroendocrine tumors, fibrosis, benign prostatic hyperplasia, atherosclerosis, restenosis, breast cancer, colon cancer, pancreas cancer, prostate cancer, lung cancer, small cell lung cancer, ovarian cancer, epidermal cancer, non-Hodgkin's lymphoma, Hodgkin's lymphoma, leukemia, and hematopoietic cancer. Camptothecin-rvD-Cha-Suc-(Doc)$_4$-Aepa-D-Phe-c(Cys-Tyr-D-Trp-Lys-Abu-Cys)-Thr-NH$_2$, a pharmaceutically acceptable salt thereof, or a pharmaceutical composition described above may also be used to treat adrenal medullary tumors (pheochromocytoma, neuroblastoma, ganglioneuroma), gastroenteropancreatic (GEP) tumors (glucagonoma, vasoactiveintestinal polypeptide secreting tumor (VIPoma), non-functioning GEP tumors), paraganglioma, pituitary ademona, astrocytomas, benign and malignant bone tumors, differentiated thyroid carcinoma (papillary, follicular, Hurthle cell), meningioma, non-small cell lung cancer and the like. In another aspect, the tumor or cancer is breast cancer. In yet another aspect, the tumor or cancer is small cell lung cancer. In yet another aspect, the tumor or cancer is prostate cancer. In addition, Camptothecin-rvD-Cha-Suc-(Doc)$_4$-Aepa-D-Phe-c(Cys-Tyr-D-Trp-Lys-Abu-Cys)-Thr-NH$_2$, a pharmaceutically acceptable salt thereof, or a pharmaceutical composition as described previously, may also be used to treat angiogenic and/or proliferative conditions associated with the formation of nascent blood vessels which include, but are not limited to, angiogenesis, proliferative diabetic retinopathy, cystic macular odema, rheumatoid arthritis, endometriosis, restenosis and psoriasis. Additional conditions or diseases benefiting from application of Camptothecin-rvD-Cha-Suc-(Doc)$_4$-Aepa-D-Phe-c(Cys-Tyr-D-Trp-Lys-Abu-Cys)-Thr-NH$_2$, a pharmaceutically acceptable salt thereof, or a pharmaceutical composition described above include but are not limited to autoimmune diseases (Graves' disease, Graves' opthalmopathy), bacterial pneumonia, cerebrovascular accident, fibrous dysplasia, granulomas (tuberculosis, sarcoid) and radiation pneumonitis.

In a sixth embodiment of the twenty-first aspect, the invention features a method of treating a disease or condition in a subject in need thereof, the method comprising administering to the subject a therapeutically effective amount of a mixture of compounds having the formulae Camptothecin-rvD-Asp-Suc-(Doc)$_4$-Aepa-D-Phe-c(Cys-Tyr-D-Trp-Lys-Abu-Cys)-Thr-NH$_2$ and Camptothecin-rvAsp-Suc-(Doc)$_4$-Aepa-D-Phe-c(Cys-Tyr-D-Trp-Lys-Abu-Cys)-Thr-NH$_2$ or pharmaceutically acceptable salts or compositions thereof, wherein the disease or condition is characterized by undesired proliferation of cells that express one or more somatostatin-type receptors such as tumor or cancer cells. Exemplary diseases or conditions include, but are not limited to, neuroendocrine tumors, fibrosis, benign prostatic hyperplasia, atherosclerosis, restenosis, breast cancer, colon cancer, pancreas cancer, prostate cancer, lung cancer, small cell lung cancer, ovarian cancer, epidermal cancer, non-Hodgkin's lymphoma, Hodgkin's lymphoma, leukemia, and hematopoietic cancer. A mixture of Camptothecin-rvD-Asp-Suc-(Doc)$_4$-Aepa-D-Phe-c(Cys-Tyr-D-Trp-Lys-Abu-Cys)-Thr-NH$_2$ and Camptothecin-rvAsp-Suc-(Doc)$_4$-Aepa-D-Phe-c(Cys-Tyr-D-Trp-Lys-Abu-Cys)-Thr-NH$_2$ or pharmaceutically acceptable salts or compositions thereof may also be used to treat adrenal medullary tumors (pheochromocytoma, neuroblastoma, ganglioneuroma), gastroenteropancreatic (GEP) tumors (glucagonoma, vasoactiveintestinal polypeptide secreting tumor (VIPoma), non-functioning GEP tumors), paraganglioma, pituitary ademona, astrocytomas, benign and malignant bone tumors, differentiated thyroid carcinoma (papillary, follicular, Hurthle cell), meningioma, non-small cell lung cancer and the like. In another aspect, the tumor or cancer is breast cancer. In yet another aspect, the tumor or cancer is small cell lung cancer. In yet another aspect, the tumor or cancer is prostate cancer. In addition, mixture of compounds having the formulae Camptothecin-rvD-Asp-Suc-(Doc)$_4$-Aepa-D-Phe-c(Cys-Tyr-D-Trp-Lys-Abu-Cys)-Thr-NH$_2$ or a pharmaceutically acceptable salt thereof and Camptothecin-rvAsp-Suc-(Doc)$_4$-Aepa-D-Phe-c(Cys-Tyr-D-Trp-Lys-Abu-Cys)-Thr-NH$_2$ or a pharmaceutically acceptable salt thereof, or a pharmaceutical composition as described previously, may also be used to treat angiogenic and/or proliferative conditions associated with the formation of nascent blood vessels which include, but are not limited to, angiogenesis, proliferative diabetic retinopathy, cystic macular odema, rheumatoid arthritis, endometriosis, restenosis and psoriasis. Additional conditions or diseases benefiting from application of a mixture of Camptothecin-rvD-Asp-Suc-(Doc)$_4$-Aepa-D-Phe-c(Cys-Tyr-D-Trp-Lys-Abu-Cys)-Thr-NH$_2$ and Camptothecin-rvAsp-Suc-(Doc)$_4$-Aepa-D-Phe-c(Cys-Tyr-D-Trp-Lys-Abu-Cys)-Thr-NH$_2$ or pharmaceutically acceptable salts or compositions thereof include, but are not limited to, autoimmune diseases (Graves' disease, Graves' opthalmopathy), bacterial pneumonia, cerebrovascular accident, fibrous dysplasia, granulomas (tuberculosis, sarcoid) and radiation pneumonitis.

The mixture of the immediately foregoing sixth embodiments comprises, weight/weight, about 2:98, about 5:95, about 10:90, about 15:85, about 20:80, about 25:75, about 30:70, about 35:65, about 40:60, about 45:50, about 50:50, about 55:45, about 60:40, about 65:25, about 70:30, about 75:25, about 80:20, about 85:15, about 90:10, about 95:5, about 97:3 or even about 98:2 of Camptothecin-rvD-Asp-Suc-(Doc)$_4$-Aepa-D-Phe-c(Cys-Tyr-D-Trp-Lys-Abu-Cys)-Thr-NH$_2$ or a pharmaceutically acceptable salt thereof and Camptothecin-rvAsp-Suc-(Doc)$_4$-Aepa-D-Phe-c(Cys-Tyr-D-Trp-Lys-Abu-Cys)-Thr-NH$_2$ or a pharmaceutically acceptable salt thereof. In a further aspect, the mixture comprises, weight/weight, about 44:56, about 58:42, about 87:13, about 88:12, about 97:3, or about 98:2 of Camptothecin-rvD-Asp-Suc-(Doc)$_4$-Aepa-D-Phe-c(Cys-Tyr-D-Trp-Lys-Abu-Cys)-Thr-NH$_2$ to Camptothecin-rvAsp-Suc-(Doc)$_4$-Aepa-D-Phe-c(Cys-Tyr-D-Trp-Lys-Abu-Cys)-Thr-NH$_2$ or a pharmaceutically acceptable salt of each thereof, respectively. In a further aspect, the mixture comprises, weight/weight, about 44:56 of Camptothecin-rvD-Asp-Suc-(Doc)$_4$-Aepa-D-Phe-c(Cys-Tyr-D-Trp-Lys-Abu-Cys)-Thr-NH$_2$ to Camptothecin-rvAsp-Suc-(Doc)$_4$-Aepa-D-Phe-c(Cys-Tyr-D-Trp-Lys-Abu-Cys)-Thr-NH$_2$ or a pharmaceutically acceptable salt of each thereof, respectively. In a further aspect, the mixture comprises, weight/weight, about 58:42 of Camptothecin-rvD-Asp-Suc-(Doc)$_4$-Aepa-D-Phe-c(Cys-Tyr-D-Trp-Lys-Abu-Cys)-Thr-NH$_2$ to Camptothecin-rvAsp-Suc-(Doc)$_4$-Aepa-D-Phe-c(Cys-Tyr-D-Trp-Lys-Abu-Cys)-Thr-NH$_2$ or a pharmaceutically acceptable salt of each thereof, respectively. In a further aspect, the mixture comprises, weight/weight, about 87:13 of Camptothecin-rvD-Asp-Suc-(Doc)$_4$-Aepa-D-Phe-c(Cys-Tyr-D-Trp-Lys-Abu-Cys)-Thr-NH$_2$ to Camptothecin-rvAsp-Suc-(Doc)$_4$-Aepa-D-Phe-c(Cys-Tyr-D-Trp-Lys-Abu-Cys)-Thr-NH$_2$ or a pharmaceutically acceptable salt of each thereof, respectively. In a further aspect, the mixture comprises, weight/weight, about 88:12 of Camptothecin-rvD-Asp-Suc-(Doc)$_4$-Aepa-D-Phe-c(Cys-Tyr-D-Trp-Lys-Abu-Cys)-Thr-NH$_2$ to Camptothecin-rvAsp-Suc-(Doc)$_4$-Aepa-D-Phe-c(Cys-Tyr-D-Trp-Lys-Abu-Cys)-Thr-NH$_2$ or a pharmaceutically acceptable salt of each thereof, respectively. In a further aspect, the mixture comprises, weight/weight, about 97:3 of Camptothecin-rvD-Asp-Suc-(Doc)$_4$-Aepa-D-Phe-c(Cys-Tyr-D-Trp-Lys-Abu-Cys)-Thr-NH$_2$ to Camptothecin-rvAsp-Suc-(Doc)$_4$-Aepa-D-Phe-c(Cys-Tyr-D-Trp-Lys-Abu-Cys)-Thr-NH$_2$ or a pharmaceutically acceptable salt of each thereof, respectively. In a further aspect, the mixture comprises, weight/weight, about 98:2 of Camptothecin-rvD-Asp-Suc-(Doc)$_4$-Aepa-D-Phe-c(Cys-Tyr-D-Trp-Lys-Abu-Cys)-Thr-NH$_2$ to Camptothecin-rvAsp-Suc-(Doc)$_4$-Aepa-D-Phe-c(Cys-Tyr-D-Trp-Lys-Abu-Cys)-Thr-NH$_2$ or a pharmaceutically acceptable salt of each thereof, respectively.

In a seventh embodiment of the twenty-first aspect, the invention features a method of treating a disease or condition in a subject in need thereof, the method comprising administering to the subject a therapeutically effective amount of a mixture of compounds Camptothecin-rvD-Glu-Suc-(Doc)$_4$-Aepa-D-Phe-c(Cys-Tyr-D-Trp-Lys-Abu-Cys)-Thr-NH$_2$ and Camptothecin-rvGlu-Suc-(Doc)$_4$-Aepa-D-Phe-c(Cys-Tyr-D-Trp-Lys-Abu-Cys)-Thr-NH$_2$ or pharmaceutically acceptable salts or compositions thereof, wherein the disease or condition is characterized by undesired proliferation of cells that express one or more somatostatin-type receptors such as tumor or cancer cells. Exemplary diseases or conditions include, but are not limited to, neuroendocrine tumors, fibrosis, benign prostatic hyperplasia, atherosclerosis, restenosis, breast cancer, colon cancer, pancreas cancer, prostate cancer, lung cancer, small cell lung cancer, ovarian cancer, epidermal cancer, non-Hodgkin's lymphoma, Hodgkin's lymphoma, leukemia, and hematopoietic cancer. A mixture of Camptothecin-rvD-Glu-Suc-(Doc)$_4$-Aepa-D-Phe-c(Cys-Tyr-D-Trp-Lys-Abu-Cys)-Thr-NH$_2$ and Camptothecin-rvGlu-Suc-(Doc)$_4$-Aepa-D-Phe-c(Cys-Tyr-D-Trp-Lys-Abu-Cys)-Thr-NH$_2$ or pharmaceutically acceptable salts or compositions thereof may also be used to treat adrenal medullary tumors (pheochromocytoma, neuroblastoma, ganglioneuroma), gastroenteropancreatic (GEP) tumors (glucagonoma, vasoactiveintestinal polypeptide secreting tumor (VIPoma), non-functioning GEP tumors), paraganglioma, pituitary ademona, astrocytomas, benign and malignant bone tumors, differentiated thyroid carcinoma (papillary, follicular, Hurthle cell), meningioma, non-small cell lung cancer and the like. In another aspect, the tumor or cancer is breast cancer. In yet another aspect, the tumor or cancer is small cell lung cancer. In yet another aspect, the tumor or cancer is prostate cancer. In addition, mixture of compounds having the formulae Camptothecin-rvD-Glu-Suc-(Doc)$_4$-Aepa-D-Phe-c(Cys-Tyr-D-Trp-Lys-Abu-Cys)-Thr-NH$_2$ and Camptothecin-rvGlu-Suc-(Doc)$_4$-Aepa-D-Phe-c(Cys-Tyr-D-Trp-Lys-Abu-Cys)-Thr-NH$_2$ or a pharmaceutically acceptable salt of each thereof, or a pharmaceutical composition as described previously, may also be used to treat angiogenic and/or proliferative conditions associated with the formation of nascent blood vessels which include, but are not limited to, angiogenesis, proliferative diabetic retinopathy, cystic macular odema, rheumatoid arthritis, endometriosis, restenosis and psoriasis. Additional conditions or diseases benefiting from application of a mixture of Camptothecin-rvD-Glu-Suc-(Doc)$_4$-Aepa-D-Phe-c(Cys-Tyr-D-Trp-Lys-Abu-Cys)-Thr-NH$_2$ and Camptothecin-rvGlu-Suc-(Doc)$_4$-Aepa-D-Phe-c (Cys-Tyr-D-Trp-Lys-Abu-Cys)-Thr-NH$_2$ or pharmaceutically acceptable salts or compositions thereof include, but are not limited to, autoimmune diseases (Graves' disease, Graves' opthalmopathy), bacterial pneumonia, cerebrovascular accident, fibrous dysplasia, granulomas (tuberculosis, sarcoid) and radiation pneumonitis.

The mixture of the immediately foregoing seventh embodiment comprises, weight/weight, about 2:98, about 5:95, about 10:90, about 15:85, about 20:80, about 25:75, about 30:70, about 35:65, about 40:60, about 45:50, about 50:50, about 55:45, about 60:40, about 65:25, about 70:30, about 75:25, about 80:20, about 85:15, about 90:10, about 95:5, about 97:3 or even about 98:2 of Camptothecin-rvD-Glu-Suc-(Doc)$_4$-Aepa-D-Phe-c(Cys-Tyr-D-Trp-Lys-Abu-Cys)-Thr-NH$_2$ and Camptothecin-rvGlu-Suc-(Doc)$_4$-Aepa-D-Phe-c(Cys-Tyr-D-Trp-Lys-Abu-Cys)-Thr-NH$_2$ or a pharmaceutically acceptable salt of each thereof. In a further aspect, the mixture comprises, weight/weight, about 80:20 of Camptothecin-rvD-Glu-Suc-(Doc)$_4$-Aepa-D-Phe-c(Cys-Tyr-D-Trp-Lys-Abu-Cys)-Thr-NH$_2$ and Camptothecin-rvGlu-Suc-(Doc)$_4$-Aepa-D-Phe-c(Cys-Tyr-D-Trp-Lys-Abu-Cys)-Thr-NH$_2$ or a pharmaceutically acceptable salt of each thereof. In a further aspect, the mixture comprises, weight/weight, about 85:15 of Camptothecin-rvD-Glu-Suc-(Doc)$_4$-Aepa-D-Phe-c(Cys-Tyr-D-Trp-Lys-Abu-Cys)-Thr-NH$_2$ and Camptothecin-rvGlu-Suc-(Doc)$_4$-Aepa-D-Phe-c(Cys-Tyr-D-Trp-Lys-Abu-Cys)-Thr-NH$_2$ or a pharmaceutically acceptable salt of each thereof. In a further aspect, the mixture comprises, weight/weight, about 87:13 of Camptothecin-rvD-Glu-Suc-(Doc)$_4$-Aepa-D-Phe-c(Cys-Tyr-D-Trp-Lys-Abu-Cys)-Thr-NH$_2$ and Camptothecin-rvGlu-Suc-(Doc)$_4$-Aepa-D-Phe-c(Cys-Tyr-D-Trp-Lys-Abu-Cys)-Thr-NH$_2$ or a pharmaceutically acceptable salt of each thereof. In a further aspect, the mixture comprises, weight/weight, about 88:12 of Camptothecin-rvD-Glu-Suc-(Doc)$_4$-Aepa-D-Phe-c(Cys-Tyr-D-Trp-Lys-Abu-Cys)-Thr-NH$_2$ and Camptothecin-rvGlu-Suc-(Doc)$_4$-Aepa-D-Phe-c(Cys-Tyr-D-Trp-Lys-Abu-Cys)-Thr-NH$_2$ or a pharmaceutically acceptable salt of each thereof. In a further aspect, the mixture comprises, weight/weight, about 90:10 of Camptothecin-rvD-Glu-Suc-(Doc)$_4$-Aepa-D-Phe-c(Cys-Tyr-D-Trp-Lys-Abu-Cys)-Thr-NH$_2$ and Camptothecin-rvGlu-Suc-(Doc)$_4$-Aepa-D-Phe-c(Cys-Tyr-D-Trp-Lys-Abu-Cys)-Thr-NH$_2$ or a pharmaceutically acceptable salt of each thereof. In a further aspect, the mixture comprises, weight/weight, about 95:5 of Camptothecin-rvD-Glu-Suc-(Doc)$_4$-Aepa-D-Phe-c(Cys-Tyr-D-Trp-Lys-Abu-Cys)-Thr-NH$_2$ and Camptothecin-rvGlu-Suc-(Doc)$_4$-Aepa-D-Phe-c(Cys-Tyr-D-Trp-Lys-Abu-Cys)-Thr-NH$_2$ or a pharmaceutically acceptable salt of each thereof. In a further aspect, the mixture comprises, weight/weight, about 97:3 of Camptothecin-rvD-Glu-Suc-(Doc)$_4$-Aepa-D-Phe-c(Cys-Tyr-D-Trp-Lys-Abu-Cys)-Thr-NH$_2$ and Camptothecin-rvGlu-Suc-(Doc)$_4$-Aepa-D-Phe-c(Cys-Tyr-D-Trp-Lys-Abu-Cys)-Thr-NH$_2$ or a pharmaceutically acceptable salt of each thereof. In a further aspect, the mixture comprises, weight/weight, about 98:2 of Camptothecin-rvD-Glu-Suc-(Doc)$_4$-Aepa-D-Phe-c(Cys-Tyr-D-Trp-Lys-Abu-Cys)-Thr-NH$_2$ and Camptothecin-rvGlu-Suc-(Doc)$_4$-Aepa-D-Phe-c(Cys-Tyr-D-Trp-Lys-Abu-Cys)-Thr-NH$_2$ or a pharmaceutically acceptable salt of each thereof.

In an eighth embodiment of the twenty-first aspect, the invention features a method of treating a disease or condition in a subject in need thereof, the method comprising administering to the subject a therapeutically effective amount is Camptothecin-rvDAsp-Suc-(Peg3)$_3$-Aepa-DPhe-c(Cys-Tyr-DTrp-Lys-Abu-Cys)-Thr-NH$_2$, a pharmaceutically acceptable salt thereof, or a pharmaceutical composition described above, wherein the disease or condition is characterized by undesired proliferation of cells that express one or more somatostatin-type receptors, such as tumor or cancer cells. Exemplary diseases or conditions include, but are not limited to, neuroendocrine tumors, fibrosis, benign prostatic hyperplasia, atherosclerosis, restenosis, breast cancer, colon cancer, pancreas cancer, prostate cancer, lung cancer, small cell lung cancer, ovarian cancer, epidermal cancer, non-Hodgkin's lymphoma, Hodgkin's lymphoma, leukemia, and hematopoietic cancer. Camptothecin-rvDAsp-Suc-(Peg3)$_3$-Aepa-DPhe-c(Cys-Tyr-DTrp-Lys-Abu-Cys)-Thr-NH$_2$, a pharmaceutically acceptable salt thereof, or a pharmaceutical composition described above may also be used to treat adrenal medullary tumors (pheochromocytoma, neuroblastoma, ganglioneuroma), gastroenteropancreatic (GEP) tumors (glucagonoma, vasoactiveintestinal polypeptide secreting tumor (VIPoma), non-functioning GEP tumors), paraganglioma, pituitary ademoma, astrocytomas, benign and malignant bone tumors, differentiated thyroid carcinoma (papillary, follicular, Hurthle cell), meningioma, non-small cell lung cancer and the like. In another aspect, the tumor or cancer is breast cancer. In yet another aspect, the tumor or cancer is small cell lung cancer. In yet another aspect, the tumor or cancer is prostate cancer. In addition, Camptothecin-rvDAsp-Suc-(Peg3)$_3$-Aepa-DPhe-c(Cys-Tyr-DTrp-Lys-Abu-Cys)-Thr-NH$_2$, a pharmaceutically acceptable salt thereof, or a pharmaceutical composition as described previously, may also be used to treat angiogenic and/or proliferative conditions associated with the formation of nascent blood vessels which include, but are not limited to, angiogenesis, proliferative diabetic retinopathy, cystic macular odema, rheumatoid arthritis, endometriosis, restenosis and psoriasis. Additional conditions or diseases benefiting from application of Camptothecin-rvDAsp-Suc-(Peg3)$_3$-Aepa-DPhe-c(Cys-Tyr-DTrp-Lys-Abu-Cys)-Thr-NH$_2$, a pharmaceutically acceptable salt thereof, or a pharmaceutical composition described above include but are not limited to autoimmune diseases (Graves' disease, Graves' opthalmopathy), bacterial pneumonia, cerebrovascular accident, fibrous dysplasia, granulomas (tuberculosis, sarcoid) and radiation pneumonitis.

In a ninth embodiment of the twenty-first aspect, the invention features a method of treating a disease or condition in a subject in need thereof, the method comprising administering to the subject a therapeutically effective amount is Camptothecin-rvDAsp-Suc-Peg$_{11}$-Aepa-DPhe-c(Cys-Tyr-DTrp-Lys-Abu-Cys)-Thr-NH$_2$, a pharmaceutically acceptable salt thereof, or a pharmaceutical composition described above, wherein the disease or condition is characterized by undesired proliferation of cells that express one or more somatostatin-type receptors, such as tumor or cancer cells. Exemplary diseases or conditions include, but are not limited to, neuroendocrine tumors, fibrosis, benign prostatic hyperplasia, atherosclerosis, restenosis, breast cancer, colon cancer, pancreas cancer, prostate cancer, lung cancer, small cell lung cancer, ovarian cancer, epidermal cancer, non-Hodgkin's lymphoma, Hodgkin's lymphoma, leukemia, and hematopoietic cancer. Camptothecin-rvDAsp-Suc-Peg$_{11}$-Aepa-DPhe-c(Cys-Tyr-DTrp-Lys-Abu-Cys)-Thr-NH$_2$, a pharmaceutically acceptable salt thereof, or a pharmaceutical composition described above may also be used to treat adrenal medullary tumors (pheochromocytoma, neuroblastoma, ganglioneuroma), gastroenteropancreatic (GEP) tumors (glucagonoma, vasoactiveintestinal polypeptide secreting tumor (VIPoma), non-functioning GEP tumors), paraganglioma, pituitary ademoma, astrocytomas, benign and malignant bone tumors, differentiated thyroid carcinoma (papillary, follicular, Hurthle cell), meningioma, non-small cell lung cancer and the like. In another aspect, the tumor or cancer is breast cancer. In yet another aspect, the tumor or cancer is small cell lung cancer. In yet another aspect, the tumor or cancer is prostate cancer. In addition, Camptothecin-rvDAsp-Suc-Peg$_{11}$-Aepa-DPhe-c(Cys-Tyr-DTrp-Lys-Abu-Cys)-Thr-NH$_2$, a pharmaceutically acceptable salt thereof, or a pharmaceutical composition as described previously, may also be used to treat angiogenic and/or proliferative conditions associated with the formation of nascent blood vessels which include, but are not limited to, angiogenesis, proliferative diabetic retinopathy, cystic macular odema, rheumatoid arthritis, endometriosis, restenosis and psoriasis. Additional conditions or diseases benefiting from application of Camptothecin-rvDAsp-Suc-Peg$_{11}$-Aepa-DPhe-c(Cys-Tyr-DTrp-Lys-Abu-Cys)-Thr-NH$_2$, a pharmaceutically acceptable salt thereof, or a pharmaceutical composition described above include but are not limited to autoimmune diseases (Graves' disease, Graves' opthalmopathy), bacterial pneumonia, cerebrovascular accident, fibrous dysplasia, granulomas (tuberculosis, sarcoid) and radiation pneumonitis.

In a tenth embodiment of the twenty-first aspect, the invention features a method of treating a disease or condition in a subject in need thereof, the method comprising administering to the subject a therapeutically effective amount is Camptothecin-rvDGlu-Suc-(Doc)$_4$-Aepa-DPhe-c(Cys-Tyr-DTrp-Lys-Abu-Cys)-Thr-NH$_2$, a pharmaceutically acceptable salt thereof, or a pharmaceutical composition described above, wherein the disease or condition is characterized by undesired proliferation of cells that express one or more somatostatin-type receptors, such as tumor or cancer cells. Exemplary diseases or conditions include, but are not limited to, neuroendocrine tumors, fibrosis, benign prostatic hyperplasia, atherosclerosis, restenosis, breast cancer, colon cancer, pancreas cancer, prostate cancer, lung cancer, small cell lung cancer, ovarian cancer, epidermal cancer, non-Hodgkin's lymphoma, Hodgkin's lymphoma, leukemia, and hematopoietic cancer. Camptothecin-rvDGlu-Suc-(Doc)$_4$-Aepa-DPhe-c(Cys-Tyr-DTrp-Lys-Abu-Cys)-Thr-NH$_2$, a pharmaceutically acceptable salt thereof, or a pharmaceutical composition described above may also be used to treat adrenal medullary tumors (pheochromocytoma, neuroblastoma, ganglioneuroma), gastroenteropancreatic (GEP) tumors (glucagonoma, vasoactiveintestinal polypeptide secreting tumor (VIPoma), non-functioning GEP tumors), paraganglioma, pituitary ademoma, astrocytomas, benign and malignant bone tumors, differentiated thyroid carcinoma (papillary, follicular, Hurthle cell), meningioma, non-small cell lung cancer and the like. In another aspect, the tumor or cancer is breast cancer. In yet another aspect, the tumor or cancer is small cell lung cancer. In yet another aspect, the tumor or cancer is prostate cancer. In addition, Camptothecin-rvDGlu-Suc-(Doc)$_4$-Aepa-DPhe-c(Cys-Tyr-DTrp-Lys-Abu-Cys)-Thr-NH$_2$, a pharmaceutically acceptable salt thereof, or a pharmaceutical composition as described previously, may also be used to treat angiogenic and/or proliferative conditions associated with the formation of nascent blood vessels which include, but are not limited to, angiogenesis, proliferative diabetic retinopathy, cystic macular odema, rheumatoid arthritis, endometriosis, restenosis and psoriasis. Additional conditions or diseases benefiting from application of Camptothecin-rvDGlu-Suc-(Doc)$_4$-Aepa-DPhe-c(Cys-Tyr-DTrp-Lys-Abu-Cys)-Thr-NH$_2$, a pharmaceutically acceptable salt thereof, or a pharmaceutical composition described above include but are not limited to autoimmune diseases (Graves' disease, Graves' opthalmopathy), bacterial pneumonia, cerebrovascular accident, fibrous dysplasia, granulomas (tuberculosis, sarcoid) and radiation pneumonitis.

In a twenty-second aspect of the invention, the cytotoxic moiety and targeting moiety are described by Formula II:

$$A\text{-}rv\text{Gly-C-E} \qquad (\text{II})$$

wherein:
A is camptothecin or a camptothecin derivative;
C is $D^1$-$D^2$-$D^3$-$D^4$ wherein
$D^1$ is glutaryl, succinyl or deleted,
$D^2$ is $(Doc)_m$ wherein m is, independently for each occurrence thereof,
4, 5 or 6 or $[Peg]_x$ wherein x is, independently for each occurrence thereof, 0-100;

D³ is (Aepa)ₙ wherein n is, independently for each occurrence thereof, 0 or 1; and D⁴ is Ahx, Nle, Apn-Asn, Arg-D-Ala-D-Tyr, Gaba-Asn, Gaba-D-Ser-D-Tyr, Leu-Gaba, Lys-D-Ser-D-Tyr, Nle or D-Ser-D-Tyr;

E is a bombesin analog of the formula

Gln-Trp-Ala-Val-β-Ala-His-Leu-Nle-R (SEQ ID NO:3); wherein

R is NH₂ or OH;

or a pharmaceutically acceptable salt thereof.

A first embodiment of the nineteenth aspect of the invention features compounds of Formula (II) having a camptothecin moiety selected from the group consisting of:

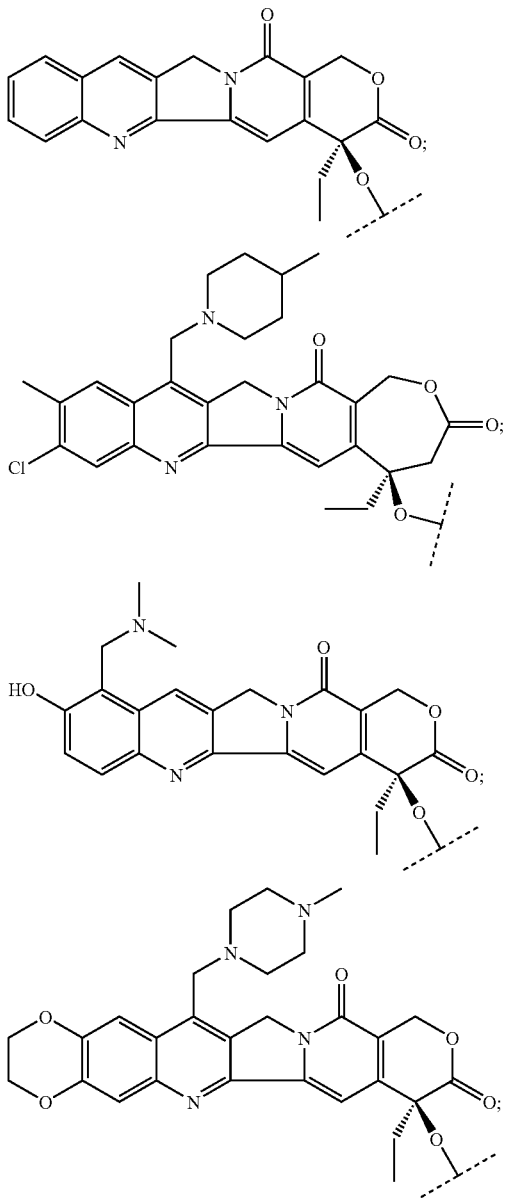

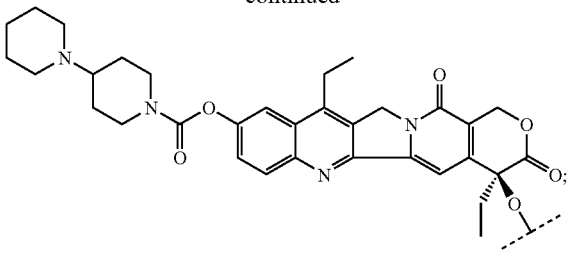

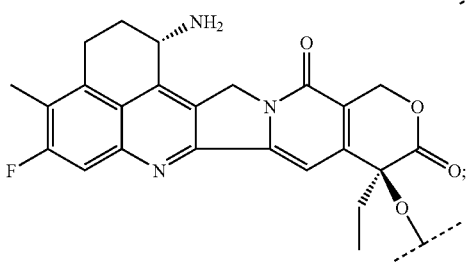

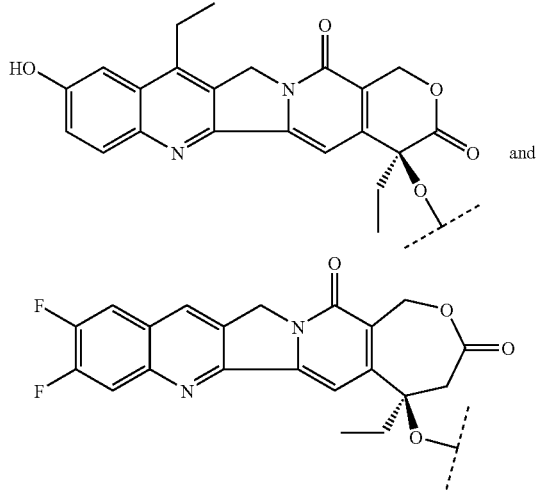

wherein the dashed line "----" in the above indicates the point of attachment of the camptothecin moiety to a second moiety, e.g., a linker or peptide.

A second embodiment of the nineteenth aspect of the invention features any of the following compounds:

Camptothecin-rvGly-Suc-(Doc)₄-Aepa-Nle-Gln-Trp-Ala-Val-β-Ala-His-Leu-Nle-NH₂ (SEQ ID NO:4);

Camptothecin-rvGly-Suc-(Doc)₄-Aepa-Ahx-Gln-Trp-Ala-Val-β-Ala-His-Leu-Nle-NH₂ (SEQ ID NO:5);

Camptothecin-rvGly-Suc-(Doc)₄-Aepa-Leu-Gaba-Gln-Trp-Ala-Val-3-Ala-His-Leu-Nle-NH₂ (SEQ ID NO:6);

Camptothecin-rvGly-Suc-(Doc)₄-Aepa-Gaba-Asn-Gln-Trp-Ala-Val-β-Ala-His-Leu-Nle-NH₂ (SEQ ID NO:7);

Camptothecin-rvGly-Suc-(Doc)₄-Aepa-Apn-Asn-Gln-Trp-Ala-Val-(3-Ala-His-Leu-Nle-NH₂ (SEQ ID NO:8);

Camptothecin-rvGly-Suc-(Doc)₄-Lys-D-Ser-D-Tyr-Gln-Trp-Ala-Val-β-Ala-His-Leu-Nle-NH₂;

Camptothecin-rvGly-Suc-(Doc)₄-Arg-D-Ala-D-Tyr-Gln-Trp-Ala-Val-β-Ala-His-Leu-Nle-NH₂;

Camptothecin-rvGly-Suc-(Doc)₄-Aepa-D-Ser-D-Tyr-Gln-Trp-Ala-Val-β-Ala-His-Leu-Nle-NH₂; o Camptothecin-rvGly-Suc-(Doc)₄-Aepa-Gaba-D-Ser-D-Tyr-Gln-Trp-Ala-Val-β-Ala-His-Leu-Nle-NH₂; or or a pharmaceutically acceptable salt thereof.

A third embodiment of the nineteenth aspect of the invention features the compound:

Camptothecin-rvGly-Suc-(Doc)$_4$-Aepa-Nle-Gln-Trp-Ala-Val-β-Ala-His-Leu-Nle-NH$_2$ (SEQ ID NO:4); or a pharmaceutically acceptable salt thereof.

The compounds according to Formula II of the invention are featured as substantially pure compounds. Substantially pure compounds are compounds which are determined to contain approximately 98% or greater of identical molecules according to Formulae IA or IB with approximately 2% or less of non-identical molecules, i.e., impurities, partially completed molecules, intermediate molecules or enantiomeric forms. Of course, substantially pure compounds include those compounds containing approximately 99%, 99.5%, 99.8% or 99.9% or greater of identical molecules with approximately 1%, 0.5%, 0.2%, or 0.1% or less of non-identical molecules. Substantially pure compounds are also contemplated to include those compounds containing 100% identical molecules.

A fourth embodiment of the nineteenth aspect of the invention features a pharmaceutical composition comprising a therapeutically effective amount of a compound of Formula (II) according to any one of the foregoing embodiments, or a pharmaceutically acceptable salt thereof and a pharmaceutically acceptable carrier.

A fifth embodiment of the nineteenth aspect of the invention features a method of treating a disease or condition in a subject in need thereof, the method comprising administering to the subject a therapeutically effective amount of a compound of Formula (II), a pharmaceutically acceptable salt thereof, or a pharmaceutical composition described above, wherein the disease or condition is characterized by undesired proliferation of cells that express one or more bombesin receptors.

A sixth embodiment of the nineteenth aspect of the invention features a method of decreasing tumor size in a subject in need thereof comprising administering a therapeutically effective amount of a compound of Formula (II), a pharmaceutically acceptable salt thereof, or a pharmaceutical composition described above, wherein the therapeutically effective amount is that amount which decreases the size of the tumor in the subject or a pharmaceutical composition thereof.

A seventh embodiment of the nineteenth aspect of the invention features a method of inhibiting the undesired proliferation of tumor cells in a subject in need thereof comprising patient comprising administering a therapeutically effective amount of a compound of Formula (II), a pharmaceutically acceptable salt thereof, or a pharmaceutical composition described above, wherein the therapeutically effective amount is that amount which inhibits the undesired proliferation of the tumor cells in the subject or a pharmaceutical composition thereof.

An eighth embodiment of the nineteenth aspect of the invention features a method of eliciting an agonist effect at a bombesin receptor in a subject in need thereof comprising patient comprising administering a therapeutically effective amount of a compound of Formula (II), a pharmaceutically acceptable salt thereof, or a pharmaceutical composition described above, wherein the therapeutically effective amount is that amount which elicits an agonist effect at a bombesin receptor in the subject or a pharmaceutical composition thereof.

A ninth embodiment of the nineteenth aspect of the invention features a method of eliciting an agonist effect at a bombesin receptor in a subject in need thereof comprising administering a therapeutically effective amount of a compound of Formula (II), a pharmaceutically acceptable salt thereof, or a pharmaceutical composition described above, wherein the compound is Camptothecin-rvGly-Suc-(Doc)$_4$-Aepa-Nle-Gln-Trp-Ala-Val-β-Ala-His-Leu-Nle-NH$_2$ (SEQ ID NO:4).

A tenth embodiment of the nineteenth aspect of the invention features a method of treating a disease or condition in a subject in need thereof, the method comprising administering to the subject a therapeutically effective amount of a compound of Formula (II), a pharmaceutically acceptable salt thereof, or a pharmaceutical composition described above, wherein the disease or condition is characterized by undesired proliferation of cells that express one or more of bombesin-type receptors. Further, the present invention is directed to a peptide-cytotoxic conjugate featuring a biologically-active analog of naturally-occurring bombesin having an active site responsible for the binding of bombesin to a receptor of a target cell. In particular, the bombesin-cytotoxic conjugates according to Formula (II) are suitable for the treatment of all forms of cancer where bombesin-related substances act as autocrine or paracrine mitotic factors especially pancreatic adenocarcinoma and small-cell lung carcinoma.

An eleventh embodiment of the nineteenth aspect of the invention features a method of treating a disease or condition in a subject in need thereof, the method comprising administering to the subject a therapeutically effective amount Camptothecin-rvGly-Suc-(Doc)$_4$-Aepa-Nle-Gln-Trp-Ala-Val-β-Ala-His-Leu-Nle-NH$_2$ (SEQ ID NO:4) a pharmaceutically acceptable salt thereof, or a pharmaceutical composition as described above, wherein the disease or condition is characterized by undesired proliferation of cells that express one or more of bombesin-type receptors, such as tumor or cancer cells. Exemplary diseases or conditions include, but are not limited to, small cell lung and pancreatic carcinomas.

As used herein, the terms "about" or "approximately" are defined to include the value presented ±5%.

As used herein the term "amino acid" refers to any naturally occurring and unnatural amino acids, including but not limited to, α-amino acids, β-amino acids, γ-amino acids and may be either D-amino acids or L-amino acids unless otherwise indicated. With the exception of the N-terminal amino acid, all abbreviations (e.g., Ala) of amino acids in this disclosure stand for the structure of —NH—C(R)(R')—CO—, wherein R and R' each is, independently, hydrogen or the side chain of an amino acid (e.g., R=CH$_3$ and R'=H for Ala), or R and R' may be joined to form a ring system. For the N-terminal amino acid, the abbreviation stands for the structure of (R$^2$R$^3$)—N—C(R)(R')—CO—, wherein R$^2$ and R$^3$ are as defined in Formula (IA) or Formula (IB) or Formula (II).

An exemplary list of preferred amino acids includes, but is not limited to, Abu, Acc (where Acc is A3c, A4c, A5c or A6c), Act, Adc, Ado, Ahp, Ahx, Aib, Ala, β-Ala, Anc, Anc, Aoc, Apc, Apn, Arg, hArg, Asp, Asn, Aun, Caeg, Cha, Cit, Cys, Dab, Dap, Dap(Z), D-Dap(Z), Dhp, Dmt, 2-Fua, Gaba, Gln, Gly, Glu, pGlu, His, 3-Hyp, 4-Hyp, Ile, Inc, hip, Ktp, Leu, hLeu, Lys, Met, Nle, Nva, Oic, Orn, 4-Pal, 3-Pal, 2-Pal, Phe, hPhe, Phg, Pip, Pro, Ser, Taz, 2-Thi, Thr, Thz, Tle, Tic, Trp, Tyr, Sar, Val or D-Val.

The peptide portion of compounds of the invention may also be denoted herein by another format, e.g., (Tyr$^{11}$)Somatostatin(1-14)-NH$_2$, with the substituted amino acid(s) from the natural sequence placed between the first set of parentheses (e.g., (Tyr$^{11}$)Somatostatin(1-14)-NH$_2$ indicates that Tyrosine has been substituted for Phenylalanine in the 11$^{th}$ residue position in the sequence of native somatostatin, i.e., H-Ala-Gly-Cys-Lys-Asn-Phe-Phe-Trp-Lys-Thr-Phe-Thr-Ser-Cys-OH). The numbers between the second set of parentheses refer to the number of amino acids present in the peptide (e.g., somatostatin(1-11) refers to amino acids 1 through 11 of the peptide sequence for somatostatin). The designation "NH$_2$" in e.g., (Tyr[11])Somatostatin(1-14)-NH$_2$ indicates that the C-terminus of the peptide is amidated whereas (Tyr[11])Somatostatin(1-14)-OH indicates the free acid form.

"Alkyl" refers to a hydrocarbon group containing one or more carbon atoms, where multiple carbon atoms if present are joined by single bonds, examples of which include but are not limited to methyl, ethyl, propyl and butyl. The alkyl hydrocarbon group may be straight-chain or contain one or more branches or cyclic groups, examples of which include but are not limited to isopropyl or tertbutyl.

"Substituted alkyl" refers to an alkyl wherein one or more hydrogen atoms of the hydrocarbon group are replaced with one or more substituents selected from the group consisting of halogen, (i.e., fluorine, chlorine, bromine and iodine), —OH, —CN, —SH, —NH$_2$, —NHCH$_3$, —NO$_2$, —C$_{1-2}$ alkyl substituted with 1 to 6 halogens, —CF$_3$, —OCH$_3$, —OCF$_3$ and/or —(CH$_2$)$_{0-4}$—COOH. In different embodiments, 1, 2, 3 or 4 substituents are present. The presence of —(CH$_2$)$_{0-4}$—COOH results in the production of an alkyl acid. Examples of alkyl acids containing, or consisting of, —(CH$_2$)$_{0-4}$—COOH, include but are not limited to 2-norbornane acetic acid, tert-butyric acid and 3-cyclopentyl propionic acid.

"Heteroalkyl" refers to an alkyl wherein one of more of the carbon atoms in the hydrocarbon group are replaced with one or more of the following atoms or groups: amino, amido, —O—, —S—, —N— or carbonyl. In different embodiments 1 or 2 heteroatoms are present.

"Substituted heteroalkyl" refers to a heteroalkyl wherein one or more hydrogen atoms of the hydrocarbon group are replaced with one or more substituents selected from the group consisting of halogen, (i.e., fluorine, chlorine, bromine and iodine), —OH, —CN, —SH, —NH$_2$, —NHCH$_3$, —NO$_2$, —C$_{1-2}$ alkyl substituted with 1 to 6 halogens, —CF$_3$, —OCH$_3$, —OCF$_3$ and/or —(CH$_2$)$_{0-4}$—COOH. In different embodiments 1, 2, 3 or 4 substituents are present.

"Alkenyl" refers to a hydrocarbon group made up of two or more carbons where one or more carbon-carbon double bonds are present, examples of which include but are not limited to, vinyl, allyl, butenyl and propenyl. The alkenyl hydrocarbon group may be straight-chain or contain one or more branches or cyclic groups, examples of which include but are not limited to, n-butenyl versus t-butenyl and n-pentenyl compared to cyclpentenyl.

"Substituted alkenyl" refers to an alkenyl wherein one or more hydrogens are replaced with one or more substituents selected from the group consisting of halogen (i.e., fluorine, chlorine, bromine, and iodine), —OH, —CN, —SH, —NHCH$_3$, —NO$_2$, —C$_{1-2}$ alkyl substituted with 1 to 6 halogens, —CF$_3$, —OCF$_3$ and/or —(CH$_2$)$_{0-4}$—COOH. In different embodiments 1, 2, 3 or 4 substituents are present.

"Aryl" refers to an optionally substituted aromatic group with at least one ring having a conjugated π-electron system containing up to two conjugated or fused ring systems. An aryl includes, but is not limited to, carboxylic aryl, heterocyclic aryl and biaryl groups. Preferably, the aryl is a 5- or 6-membered ring. Preferred atoms for a heterocyclic aryl include, but are not limited to, one or more of sulfur, oxygen and/or nitrogen. Examples of aryl include, but are not limited to, phenyl, 1-naphthyl, 2-naphthyl, indole, quinoline, 2-imidazole and 9-anthracene. Aryl substituents are selected from the group consisting of —C$_{(1-4)}$ alkyl, —C$_{(1-4)}$ alkoxy, halogen (i.e., fluorine, chlorine, bromine and iodine), —OH, —CN, —SH, —NH$_2$, —NO$_2$, —C$_{(1-2)}$ alkyl substituted with 1 to 5 halogens, —CF$_3$, —OCF$_3$ and —(CH$_2$)$_{0-4}$—COOH. In different embodiments the aryl contains 0, 1, 2, 3 or 4 substituents.

"Alkylaryl" refers to an "alkyl" joined to an "aryl", as defined above.

The term "cycloalkyl" is intended to include a mono-cycloalkyl group or a bi-cycloalkyl group of the indicated carbon number known to those of skill in the art.

The term "heterocycle" includes mono-cyclic and bi-cyclic systems having one or more heteroatoms, such as oxygen, nitrogen and/or sulfur. The ring systems may be aromatic, for example pyridine, indole, quinoline, pyrimidine, thiophene (also known as thienyl), furan, benzothiophene, tetrazole, dihydroindole, indazole, N-formylindole, benzimidazole, thiazole and thiadiazole. The ring systems also may be non-aromatic, for example, but not limited to, pyrrolidine, piperidine, morpholine and the like.

The chemist of ordinary skill will recognize that certain combinations of heteroatom-containing substituents listed in this invention define compounds which will be less stable under physiological conditions. Accordingly, such compounds are less preferred.

In the structures exemplified below and elsewhere in this application, a dashed line "----" indicates the point of attachment of the representative moiety, e.g. a camptothecin, to a second moiety, e.g., a linker or peptide.

The following list of some of the abbreviations used through the present application is provided for ease of reference, however, any abbreviation used in the instant application not defined herein are not used contrary to the recognized meanings thereof.

Doc is 8-amino-3,6-dioxaoctanoic acid is represented by the structure:

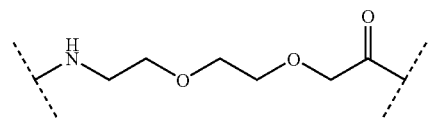

Aepa is 4-(2-aminoethyl)-1-carboxy methyl-piperazine is represented by the structure:

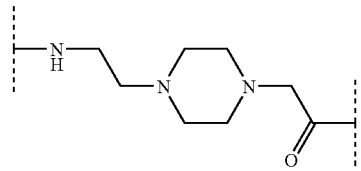

Suc or succinyl is represented by the structure:

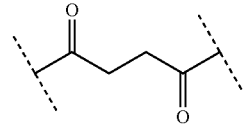

Glut or glutaryl is represented by the structure:
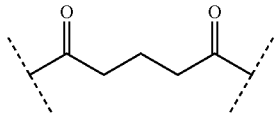
A camptothecin moiety has the structure of:
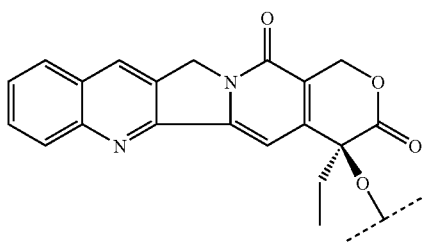
Camptothecin derivative moieties include, but are not limited to, the following structures:
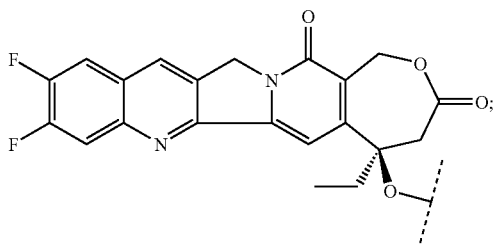
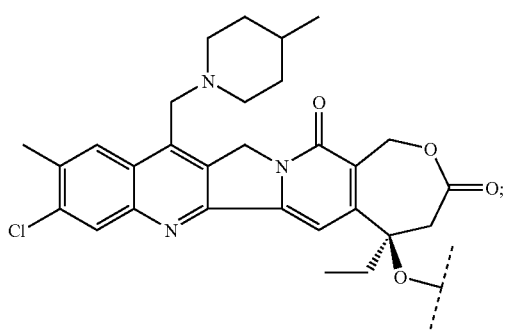
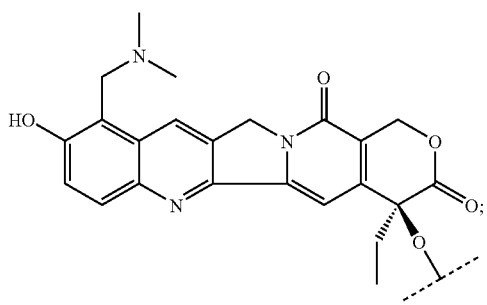
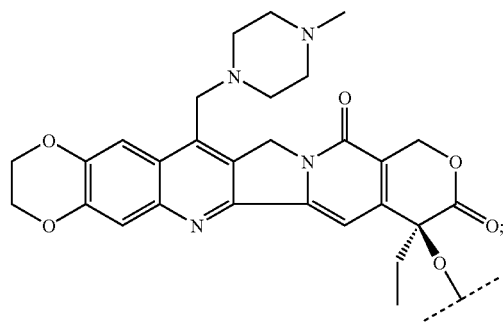
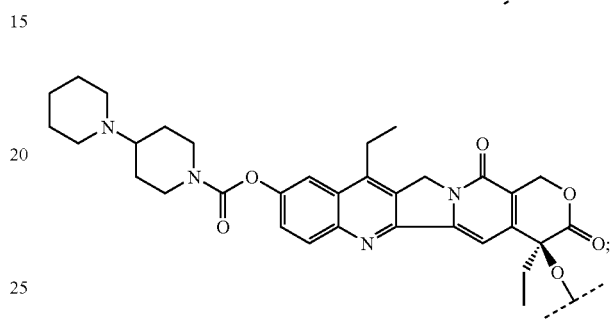
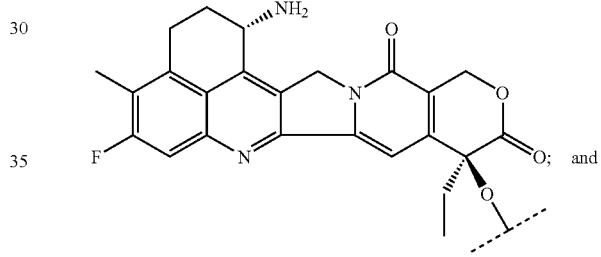; and
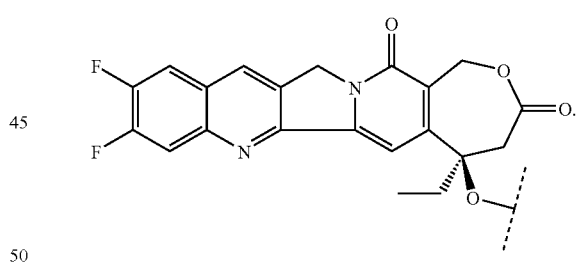
"SN38" represents:
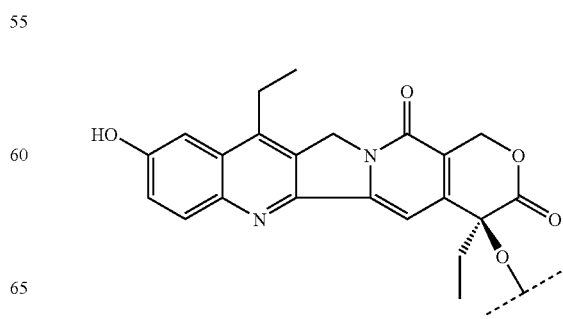

D-Lys(–) is represented by the structure:

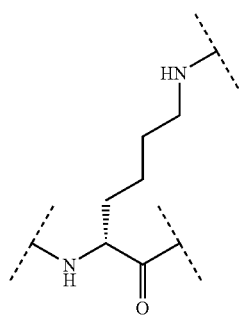

D-Orn(–) is represented by the structure:

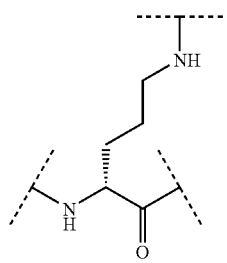

D-Dab(–) is represented by the structure:

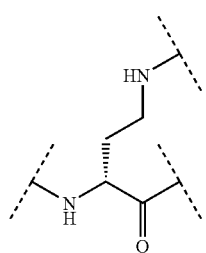

D-Dap(–) is represented by the structure:

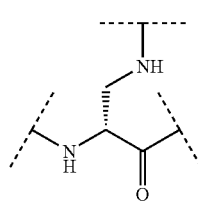

D-Apa(–) is represented by the structure:

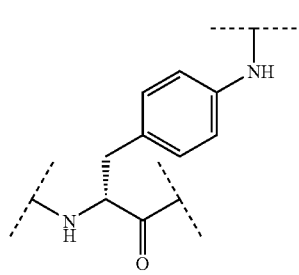

Certain abbreviations used herein are defined as follows:
Abu α-aminobutyric acid
Acc 1-amino-1-cyclo($C_3$-$C_9$)alkyl carboxylic acid, wherein A3c represents 1-amino-1-cyclopropanecarboxylic acid;
A4c represents 1-amino-1-cyclobutanecarboxylic acid;
A5c represents 1-amino-1-cyclopentanecarboxylic acid; and
A6c represents 1-amino-1-cyclohexanecarboxylic acid
Act 4-amino-4-carboxytetrahydropyran denotes the structure:

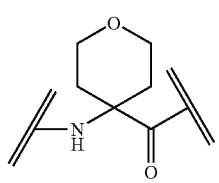

where, as used herein and elsewhere in the application, parallel lines "=" indicate points of attachment of the moiety to another moiety or sequence.
Aib α-aminoisobutyric acid
Ala or A alanine
β-Ala beta-alanine
Apc denotes the structure:

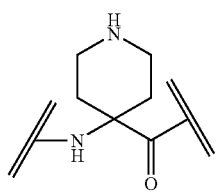

Arg or R arginine
hArg homoarginine
Asn or N asparagine
Asp or D aspartic acid
Apn 5-aminopentanoic acid
Cha β-cyclohexylalanine
Cys or C cysteine
Dab 2,4-diaminobutyric acid
Dap 2,3-diaminopropionic acid
Dhp 3,4-dehydroproline
Dmt 5,5-dimethylthiazolidine-4-carboxylic acid
Doc 8-amino-3,6-dioxaoctanoic acid denoted by the structure:

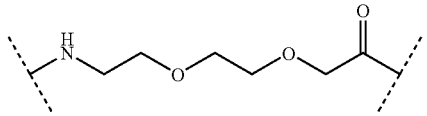

2-Fua β-(2-furyl)-alanine
Gln or Q glutamine
Glu or E glutamic acid
pGlu or Glp pyroglutamic acid
Gly or G glycine
His or H histidine
3-Hyp trans-3-hydroxy-L-proline, i.e., (2S,3S)-3-hydroxypyrrolidine-2-carboxylic acid
4-Hyp 4-hydroxyproline, i.e., (2S,4R)-4-hydroxypyrrolidine-2-carboxylic acid Ile or I isoleucine
Inc indoline-2-carboxylic acid
Inp isonipecotic acid
Ktp 4-ketoproline
Leu or L leucine
hLeu homoleucine
Lys or K lysine
Met or M methionine
Nle norleucine
$N^\epsilon$ indicates that the entity within the brackets is coupled to the epsilon-nitrogen of the Lysine sidechain
Nva norvaline
Oic octahydroindole-2-carboxylic acid
Orn ornithine
2-Pal β-(2-pyridyl)alanine
3-Pal β-(3-pyridyl)alanine
4-Pal β-(4-pyridyl)alanine
$Peg_{11}$ Peg wherein w is, independently for each occurrence thereof, 2-100, and when w is 2, the structure is referred to as Peg3.
Phe or F phenylalanine
hPhe homophenylalanine
Pip pipecolic acid
Pro or P proline
Sar sarcosine or N-methyl glycine
Ser or S serine
Taz β-(4-thiazolyl)alanine denoted by the structure:

2-Thi β-(2-thienyl)alanine
3-Thi β-(3-thienyl)alanine
Thr or T threonine
Thz thiazolidine-4-carboxylic acid
Tic 1,2,3,4-tetrahydroisoquinoline-3-carboxylic acid
Tle tert-leucine
3-(I)Tyr 3-iodo-tyrosine 3-(I)Tyr(Dop2) denoted by the structure:

Val or V valine
Gaba 4-aminobutyric acid
Apn 5-aminopentanoic acid
Ahx 6-aminohexanoic acid
Ahp 7-aminoheptanoic acid
Aoc 8-aminooctanoic acid
Anc 9-aminononanoic acid
Adc 10-aminodecanoic acid
Aim 11-aminoundecanoic acid
Ado 12-aminododecanoic acid
Phg phenylglycine
Caeg N-(2-aminoethyl)-N-(2-cytosinyl-1-oxo-ethyl)-glycine denoted by the structure:

rv(AA) the designated amino acid bonded in reverse orientation in the compound, for example,
Camptothecin-rvD-Asp-Suc- or CPT-rvD-Asp-Suc- has the structure of:

Camptothecin-rvD-Asp- or CPT-rvD-Asp- has the structure of:

Camptothecin-rvAsp-Suc- or CPT-rvAsp-Suc- has the structure of:

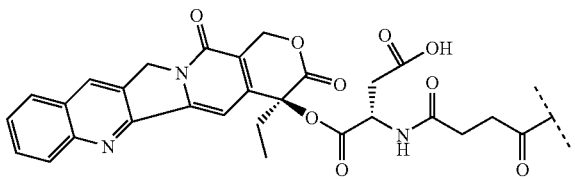

Camptothecin-rvAsp- or CPT-rvAsp- has the structure of:

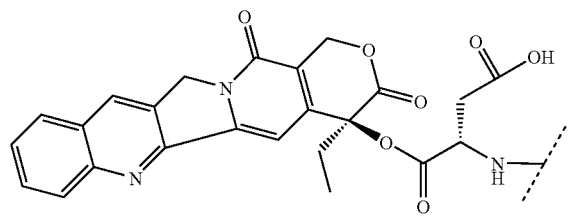

Certain other abbreviations used herein are defined as follows:
Aloc: allyloxycarbonyl
Boc: tert-butyloxycarbonyl
Bhoc benzhydryloxycarbonyl
Bzl: benzyl
DCM: dichloromethane
Dde: 1-(4,4-dimethyl-2,6-dioxocyclohex-1-ylidine)ethyl]
DIC: N,N-diisopropylcarbodiimide
DIEA: diisopropylethyl amine
Dmab: 4-{N-(1-(4,4-dimethyl-2,6-dioxocyclohexylidene)-3-methylbutyl)-amino}benzyl
DMAP: 4-(dimethylamino)pyridine
DMF: dimethylformamide
DNP: 2,4-dinitrophenyl
et: ethyl
Fmoc: fluorenylmethyloxycarbonyl
HATU: O-(7-azabenzotriazole-1-yl)-1,1,3,3-tetramethyluronium hexafluorophosphate
HBTU: 2-(1H-benzotriazole-1-yl)-1,1,3,3-tetramethyluronium hexafluorophosphate
cHex cyclohexyl
HOAT: O-(7-azabenzotriazol-1-yl)-1,1,3,3-tetramethyluronium hexafluorophosphate
HOBt: 1-hydroxy-benzotriazole
MBHA: 4-methylbenzhydrylamine
Mmt: 4-methoxytrityl
NMP: N-methylpyrrolidone
Pbf: 2,2,4,6,7-pentamethyldihydrobenzofuran-5-sulfonyl
tBu: tert-butyl
TIS: triisopropylsilane
TOS: tosyl
Trt: trityl
TFA: trifluoro acetic acid
TFFH: tetramethylfluoroforamidinium hexafluorophosphate
Z: benzyloxycarbonyl

BRIEF DESCRIPTION OF THE DRAWINGS

FIG. 3: Effects of Example 5C against small cell lung carcinoma tumor model H345 SCLC in female athymic nude mice. Suppression of tumor growth in vivo in mice (qwk×3, iv. schedule; H345 SCLC xenograft model) untreated (circle symbol) treated with 165.6 mg/kg (square symbol), 138 mg/kg (downward triangle), 55.2 mg/kg (upward triangle) Example 5C or 7.5 mg/kg camptothecin (diamond symbol).

DETAILED DESCRIPTION

Figure 1:
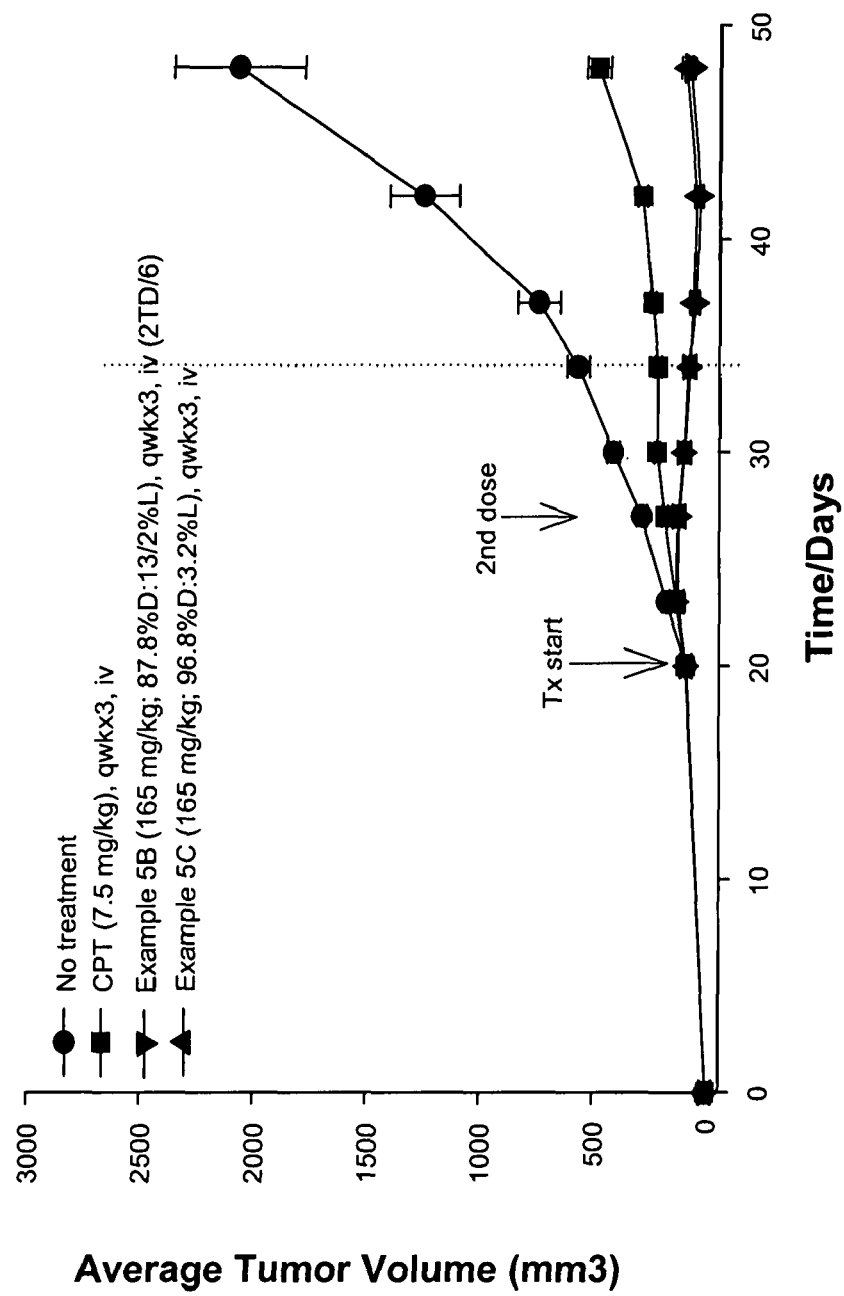
FIG. 1: Effects of Examples 5B and 5C against small cell lung carcinoma tumor model NCI-H69 in female athymic nude mice. Suppression of tumor growth in vivo in mice (qwk×3, i.v. schedule; NCI-H69 SCLS xenograft model) treated with mixtures of compounds comprising, weight/weight, 87.8:13.2 (downward triangle, Example 5B) or 96.8:3.2 (upward triangle, Example 5C) Camptothecin-rvD-Asp-Suc-(Doc)$_4$-Aepa-D-Phe-c(Cys-Tyr-D-Trp-Lys-Abu-Cys)-Thr-NH$_2$ and Camptothecin-rvAsp-Suc-(Doc)$_4$-Aepa-D-Phe-c(Cys-Tyr-D-Trp-Lys-Abu-Cys)-Thr-NH$_2$.

The invention features targeted cytotoxic compounds comprising a cytotoxic moiety bound to a targeting moiety, such as, for example, a ligand of a biological receptor, and methods relating to their therapeutic use for the treatment of neoplasia, hyperplasia, and other conditions associated with undesired proliferation of cells.

Examples of somatostatin peptides useful in the present invention are described herein. Further examples are those covered by formulae or those specifically recited in the publications set forth below, each of which is hereby incorporated by reference in its entirety:
PCT Application No. WO 03/057214 (2003)
U.S. Application No. 20030191134 (2003)
U.S. Application No. 20030083241 (2003)
U.S. Pat. No. 6,316,414 (2001)
PCT Application No. WO 02/10215 (2002)
PCT Application No. WO 99/22735 (1999)
PCT Application No. WO 98/08100 (1998)
PCT Application No. WO 98/44921 (1998)
PCT Application No. WO 98/45285 (1998)
PCT Application No. WO 98/44922 (1998)
EP Application No. P5164 EU (Inventor: G. Keri);
Van Binst, G. et al., Peptide Research, 1992, 5:8;
Horvath, A. et al., Abstract, "Conformations of Somatostatin Analogs Having Antitumor Activity", 22nd European peptide Symposium, Sep. 13-19, 1992, Interlaken, Switzerland;
PCT Application No. WO 91/09056 (1991);
EP Application No. 0 363 589 A2 (1990);
U.S. Pat. No. 4,904,642 (1990);
U.S. Pat. No. 4,871,717 (1989);
U.S. Pat. No. 4,853,371 (1989);
U.S. Pat. No. 4,725,577 (1988);
U.S. Pat. No. 4,684,620 (1987);
U.S. Pat. No. 4,650,787 (1987);
U.S. Pat. No. 4,603,120 (1986);
U.S. Pat. No. 4,585,755 (1986);
EP Application No. 0 203 031 A2 (1986);
U.S. Pat. No. 4,522,813 (1985);
U.S. Pat. No. 4,486,415 (1984);
U.S. Pat. No. 4,485,101 (1984);
U.S. Pat. No. 4,435,385 (1984);

U.S. Pat. No. 4,395,403 (1983);
U.S. Pat. No. 4,369,179 (1983);
U.S. Pat. No. 4,360,516 (1982);
U.S. Pat. No. 4,358,439 (1982);
U.S. Pat. No. 4,328,214 (1982);
U.S. Pat. No. 4,316,890 (1982);
U.S. Pat. No. 4,310,518 (1982);
U.S. Pat. No. 4,291,022 (1981);
U.S. Pat. No. 4,238,481 (1980);
U.S. Pat. No. 4,235,886 (1980);
U.S. Pat. No. 4,224,199 (1980);
U.S. Pat. No. 4,211,693 (1980);
U.S. Pat. No. 4,190,648 (1980);
U.S. Pat. No. 4,146,612 (1979);
U.S. Pat. No. 4,133,782 (1979);
U.S. Pat. No. 5,506,339 (1996);
U.S. Pat. No. 4,261,885 (1981);
U.S. Pat. No. 4,728,638 (1988);
U.S. Pat. No. 4,282,143 (1981);
U.S. Pat. No. 4,215,039 (1980);
U.S. Pat. No. 4,209,426 (1980);
U.S. Pat. No. 4,190,575 (1980);
EP Patent No. 0 389 180 (1990);
EP Application No. 0 505 680 (1982);
EP Application No. 0 083 305 (1982);
EP Application No. 0 030 920 (1980);
PCT Application No. WO 88/05052 (1988);
PCT Application No. WO 90/12811 (1990);
PCT Application No. WO 97/01579 (1997);
PCT Application No. WO 91/18016 (1991);
U.K. Application No. GB 2,095,261 (1981);
French Application No. FR 2,522,655 (1983); and
PCT Application No. WO 04/093807 (2004).

Examples of bombesin peptides useful in the present invention are described herein. Further examples are those covered by formulae or those specifically recited in the publications set forth below, each of which is hereby incorporated by reference in its entirety:
EP Application No. 0 309 297 (1989)
EP Application No. 0 339 193 (1989)
EP Application No. 0 402 852 (1990)
EP Application No. 0 434 979 (1991)
EP Application No. 0 468 497 (1992)
EP Application No. 0 835 662 (1998)
U.S. Application No. 2003050436 (2003)
U.S. Application No. 2003166539 (2003)
U.S. Pat. No. 5,084,555 (1992)
U.S. Pat. No. 5,100,873 (1992)
U.S. Pat. No. 5,217,955 (1993)
U.S. Pat. No. 5,369,094 (1994)
U.S. Pat. No. 5,410,018 (1995)
U.S. Pat. No. 5,620,955 (1997)
U.S. Pat. No. 5,723,578 (1998)
U.S. Pat. No. 5,843,903 (1998)
U.S. Pat. No. 5,877,277 (1999)
U.S. Pat. No. 6,156,725 (2000)
U.S. Pat. No. 6,307,017 (2001)
PCT Application No. WO 90/03980 (1990)
PCT Application No. WO 91/06563 (1991)
PCT Application No. WO 91/17181 (1991)
PCT Application No. WO 94/02018 (1994)
PCT Application No. WO 94/21674 (1994)
PCT Application No. WO 04/093807 (2004);

The methods for synthesizing somatostatin and bombesin peptides are well documented and are within the ability of a person of ordinary skill in the art (e.g., particularly synthesis details of compounds, moieties and intermediates as found in PCT Publication No. WO 04/093807, incorporated herein by reference in its entirety). Further synthetic procedures are provided in the following examples. The following examples also illustrate methods for synthesizing the targeted cytotoxic compounds of the present invention.

EXAMPLES

The cytotoxic conjugates of the invention comprise a cytotoxic agent, a linker and a peptide joined together in a single molecule. The peptide portion of the molecule was synthesized using solid phase chemistry while the cytotoxic agent and linker were joined using solution based chemistry. The conjugate was formed by coupling the cytotoxic agent to the N-terminal portion of the peptide resin via the linker moiety. The final product was produced by cleavage of the resin and oxidation of the crude liner peptide followed by purification via HPLC. Further details of the syntheses of the cytotoxic conjugates contemplated by the invention are described below.

Example 1

Preparation of Camptothecin-rvCha-Suc-(Doc)$_4$-Aepa-DPhe-c(Cys-Tyr-DTrp-Lys-Abu-Cys)-Thr-NH$_2$ Step A. Synthesis of H-(Doc)$_4$-Aepa-D-Phe-Cys(Trt)-Tyr(tBu)-D-Trp(Boc)-Lys(Boc)-Abu-Cys(Trt)-Thr(tBu)-Resin The protected peptide-resin was automatically synthesized on an Applied Biosystems® model 433A peptide synthesizer (obtained from Applied Biosystems, Foster City, Calif., U.S.A.) using fluorenylmethyloxycarbonyl (Fmoc) chemistry. A 1 mmol scale of Rink Amide MBHA® resin (4-methylbenzhydrylamine) (obtained from Nova Biochem, La Jolla, Calif., U.S.A.) with a substitution of 0.72 mmol/g was used.

Fmoc-8-amino-3,6-dioxaoctanoic acid (Fmoc-Doc-OH) was purchased from Chem-Impex International® (Wood Dale, Ill.). Fmoc-4(2-aminoethyl)1-carboxymethyl-piperazine.2HCl (Fmoc-Aepa-OH) was purchased from Neosystem® (Strasbourg, France). Fmoc-DPhe-OH, Fmoc-Cys(Trt)-OH, Fmoc-Tyr(tBu)-OH, Fmoc-D-Trp(Boc)-OH, Fmoc-Lys(Boc)-OH, Fmoc-Abu-OH, and Fmoc-Thr(tBu)-OH were purchased from AnaSpec® (San Jose, Calif., U.S.A.).

Prior to coupling, the Fmoc groups were removed by treatment with 20% piperidine in N-methylpyrrolidone (NMP) for 30 minutes. For each coupling step, the Fmoc amino acid (3 equivalents, 3 mmol) was first pre-activated by using 6 ml of 0.45M 2-(1-H-benzotriazole-1-yl)-1,1,2,3-tetramethyluronium hexafluorophosphate/1-hydroxy-benzotriazole (HBTU/HOBT) in DMF. The activated amino acid ester, 3 ml of 2M diisopropylethylamine (DIEA) and 3 ml of NMP were added to the resin. The ABI 433A® peptide synthesizer was programmed to perform the following reaction cycle:
(1) washing with NMP;
(2) removal of Fmoc protecting group with 20% piperidine in NMP for 30 minutes;
(3) washing with NMP; and
(4) double-coupling with pre-activated amino acid twice (1 hour intervals each time).

The protected peptide-resin i.e., H-DPhe-Cys(Trt)-Tyr(tBu)-D-Trp(Boc)-Lys(Boc)-Abu-Cys(Trt)-Thr(tBu)-Rink Amid MBHA, was then manually coupled to Fmoc-Aepa-OH and Fmoc-Doc-OH. Coupling to Fmoc-Aepa-OH was carried out by dissolving 2 equivalents of Fmoc-Aepa-OH, 1.8 equivalents of HATU, 2 equivalents of HOAT and 24 equivalents of DIEA in DMF and mixing for two minutes; the activated amino acid ester/DMF mixture was shaken with the protected peptide resin for 2 hours. An aliquot of the resin was subjected to a ninhydrin test which confirmed that the reaction was complete. The resin was washed with DMF and deprotected Fmoc with 25% piperidine in DMF for 30 minutes. After washing with DMF, the resin was coupled with Fmoc-Doc-OH by using DIC/HOBT as the coupling reagent. For each Fmoc-Doc-OH coupling, the resin was mixed with a solution containing 3.2 equivalents of Fmoc-Doc-OH in 0.4N HOBT/NMP and 5.3 equivalents of DIC in 0.4N DIC/DMF for one hour; the coupling reaction was repeated one time. The resin was washed with DMF and treated with 25% piperidine/DMF to remove the Fmoc-protecting group. After washing with DMF and DCM, the peptide-resin was ready to couple with the desired cytotoxic moiety.

Step B. Synthesis of Camptothecin-rvCha-Succinic Acid

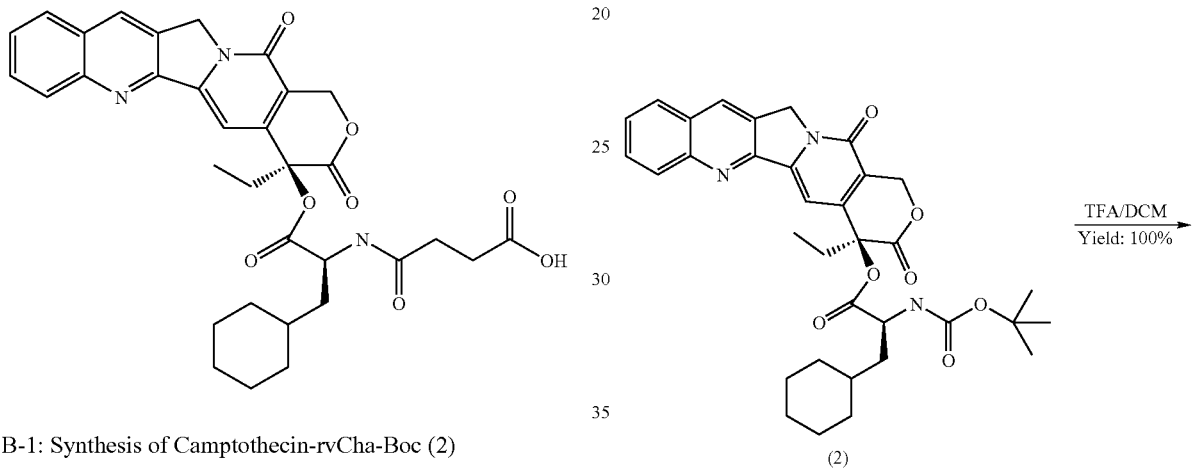

B-1: Synthesis of Camptothecin-rvCha-Boc (2)

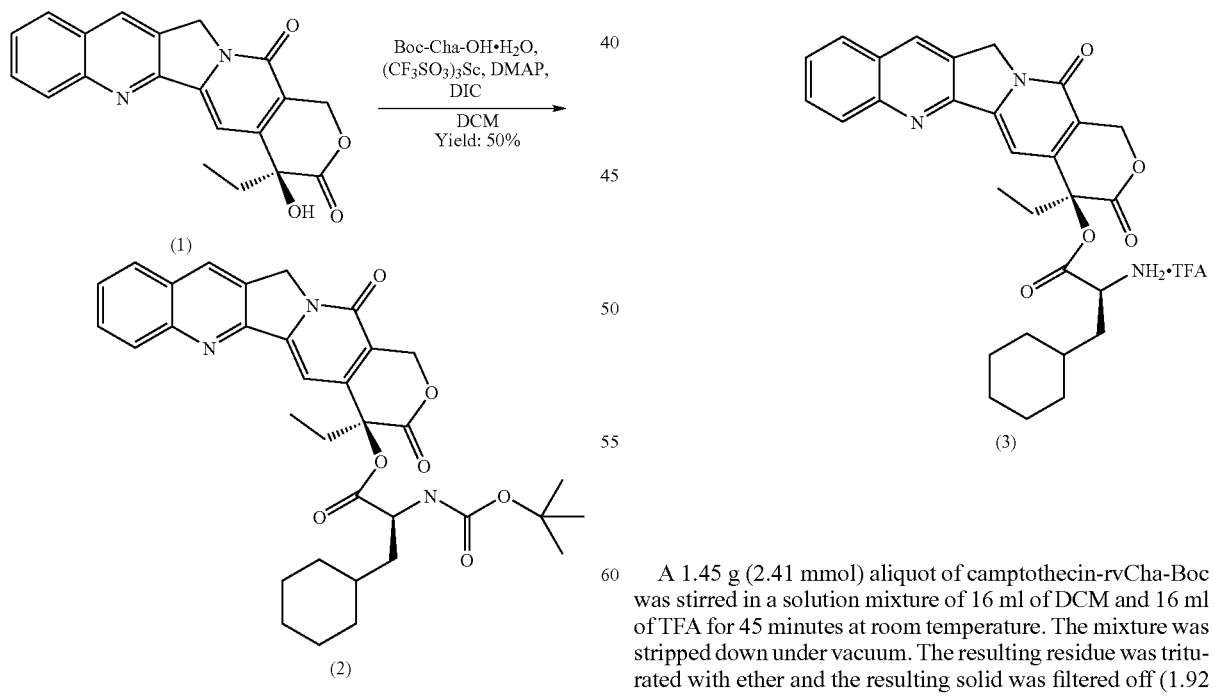

To an ice cooled suspension of Camptothecin ((1); 1.669 g, 4.79 mmol), Boc-L-Cha-OH·H$_2$O (4.9952 g, 30.995 mmol), (Cf$_3$SO$_3$)$_3$Sc (1.6972 g, 3.4485 mmol) and DMAP (2.119 g, 17.24 mmol) in DCM (162 ml) were added followed by the addition of DIC (2.958 ml, 18.87 mmol). The reaction solution was stirred under a blanket of N$_2$ in a salt-ice bath for 1 hour. After removal from the salt-ice bath, the reaction suspension was stirred overnight producing a clear solution which was then diluted with DCM and washed successively with 10% citric acid (50 ml×3 rinses), saturated NaHCO$_3$ (50 ml×3 rinses) and brine (50 ml×3 rinses), dried over Na$_2$SO$_4$ and stripped down under vacuum. The crude product (2.28 g) was separated using silica gel chromatography and eluted with a solution containing DCM/MeOH, 8/0.2, v/v. The fractions containing pure product were pooled and evaporated under vacuum to give 1.45 g of a yellow powder with a yield of 50%. The actual molecular weight of the camptothecin-rvCha-Boc as determined by MS (electro-spray) was 602.5 consistent with the calculated molecular weight 601.7.

B-2: Synthesis of Camptothecin-rvCha TFA Salt (3)

A 1.45 g (2.41 mmol) aliquot of camptothecin-rvCha-Boc was stirred in a solution mixture of 16 ml of DCM and 16 ml of TFA for 45 minutes at room temperature. The mixture was stripped down under vacuum. The resulting residue was triturated with ether and the resulting solid was filtered off (1.92 g). The actual molecular weight of the camptothecin-rvCha TFA salt as determined by MS (electro-spray) was 502.7 consistent with the calculated molecular weight of 501.7.

B-3: Synthesis of Camptothecin-rvCha-Succinic Acid

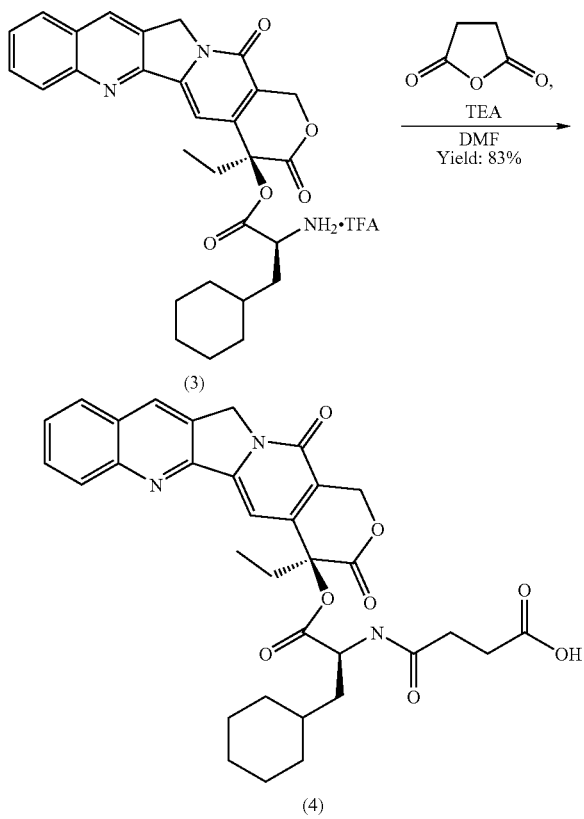

To 40 ml DMF solution of camptothecin-rvCha TFA salt (1.07 g, 1.74 mmol) was added succinic anhydride (0.28 g, 2.77 mmol) followed by the addition of TEA (1.16 ml, 8.31 mmol). The mixture was stirred for 2 hours at room temperature and HPLC analysis indicated that the reaction was complete. The solution was evaporated under vacuum, the resulting residue was stirred with water for one hour and precipitate was collected by filtration. Approximately 0.8642 g of the product was obtained. The actual molecular weight of the camptothecin-rvCha-succinic acid as determined by MS (electro-spray) was 602.7 consistent with the calculated molecular weight of 601.1. The yield was 83%.

Step C. Synthesis of Camptothecin-rvCha-Suc-(Doc)$_4$-Aepa-DPhe-c(Cys-Tyr-DTrp-Lys-Abu-Cys)-Thr-NH$_2$ A 0.6 mmol aliquot of the resin prepared according to section (A) was mixed with 20 ml DMF/DCM (1:1, v/v) containing camptothecin-rvCha-succinic acid (0.397 g, 0.66 mmol, 1.1 equivalents), DIC (0.75 ml, 8 equivalents), HOAt (0.163 g, 2 equivalents) and DIEA (3 ml, 20 equivalents) for 48 hours. The resin was drained and washed successively with DMF, MeOH and DCM. After air drying, the resin was cleaved in a mixture of TFA, H$_2$O and TIS (24 ml/2.2 ml/1.92 ml) for 2 hours. The resin was filtered off and the filtrate was poured into 300 ml of cold ether. The resulting precipitate was centrifuged and collected. The crude linear product was dissolved in a solvent system containing 300 ml of 5% AcOH and 30 ml of CH$_3$CN, to which 0.25N iodine solution in MeOH was added dropwise until a yellow color was maintained. The reaction solution was stirred for 1 hour, quenched using a few drops of 10% Na$_2$SSO$_3$ aqueous solution, and then filtered. The filtrate was purified using reverse-phase preparative HPLC using a 4×43 cm column of C$_{18}$ DYNAMAX-100® A° (Varian®, Walnut Creek, Calif., U.S.A.). The column was eluted with a linear gradient from 20% B to 45% B in 50 minutes, where A was 0.1% TFA in water and B was 0.1% TFA in CH$_3$CN. Fractions were analyzed by MS and those fractions containing the desired product were pooled and subjected to salt exchange. The pooled fractions were analyzed by MS and HPLC, and the fractions containing the pure product were pooled and lyophilized to dryness. The actual molecular weight of the camptothecin-rvCha-Suc-(Doc)$_4$-Aepa-DPhe-c(Cys-Tyr-DTrp-Lys-Abu-Cys)-Thr-NH$_2$ as determined by MS (electro-spray) was 2365.6 consistent with calculated molecular weight 2365.74. The yield was 99.9%.

Example 2

Preparation of Camptothecin-rvGly-Glut-(Doc)$_6$-Lys-D-Tyr-D-Tyr-c(Cys-3-(I)Tyr-D-Trp-Lys-Abu-Cys)-Thr-NH$_2$ The titled compound was synthesized substantially according to the procedure described in Example 1

Example 3

Preparation of Camptothecin-rvGly-Glut-(Doc)$_4$-Lys-D-Tyr-D-Tyr-c(Cys-3-(I)Tyr-D-Trp-Lys-Abu-Cys)-Thr-NH$_2$ The titled compound was synthesized substantially according to the procedure described in Example 1.

Example 4

Preparation of Camptothecin-rvGly-Glut-(Doc)$_4$-Lys-D-Tyr-D-Tyr-c(Cys-Phe-Phe-D-Trp-Lys-Thr-Cys)-NH$_2$ The titled compound was synthesized substantially according to the procedure described in Example 1.

Example 5A

Preparation of a mixture of Camptothecin-rvD-Asp-Suc-(Doc)$_4$-Aepa-D-Phe-c(Cys-Tyr-D-Trp-Lys-Abu-Cys)-Thr-NH$_2$ Camptothecin-rvAsp-Suc-(Doc)$_4$-Aepa-D-Phe-c(Cys-Tyr-D-Trp-Lys-Abu-Cys)-Thr-NH$_2$ The titled conjugate was synthesized substantially according to the procedure described in synthesis of Example 1 except for the preparation of cytotoxic portion of the molecule. After the synthesis of camptothecin-rvAsp(tBu)Boc, the N-Boc was selectively deprotected in the presence of its β-COOtBu-ester using AcOtBu/BuOH with 4M HCl in dioxane. The actual molecular weight as determined by MS (electro-spray; see Table 1B).

The product was determined to be a mixture of approximately 44.2% Camptothecin-rvD-Asp-Suc-(Doc)$_4$-Aepa-D-Phe-c(Cys-Tyr-D-Trp-Lys-Abu-Cys)-Thr-NH$_2$ and 55.8% Camptothecin-rvAsp-Suc-(Doc)$_4$-Aepa-D-Phe-c(Cys-Tyr-D-Trp-Lys-Abu-Cys)-Thr-NH$_2$. The product of a second synthesis reaction was determined to contain approximately 58.2% Camptothecin-rvD-Asp-Suc-(Doc)$_4$-Aepa-D-Phe-c(Cys-Tyr-D-Trp-Lys-Abu-Cys)-Thr-NH$_2$ and 41.8% Camptothecin-rvAsp-Suc-(Doc)$_4$-Aepa-D-Phe-c(Cys-Tyr-D-Trp-Lys-Abu-Cys)-Thr-NH$_2$.

The skilled artisan would know that chiral column purification may be utilized to further isolate the rvL-Asp or rvD-Asp forms of the two conjugated peptides.

Example 5B

Preparation of a mixture of Camptothecin-rvD-Asp-Suc-(Doc)₄-Aepa-D-Phe-c(Cys-Tyr-D-Trp-Lys-Abu-Cys)-Thr-NH₂ Camptothecin-rvAsp-Suc-(Doc)₄-Aepa-D-Phe-c(Cys-Tyr-D-Trp-Lys-Abu-Cys)-Thr-NH₂

The titled conjugate was synthesized substantially according to the procedure described in synthesis of Example 1 except for the preparation of cytotoxic portion of the molecule. After the synthesis of camptothecin-rvAsp(tBu)Boc, the N-Boc was selectively deprotected in the presence of its β-COOtBu-ester using AcOtBu/BuOH with 4M HCl in dioxane and the rvD-Asp form of the molecule (peak 1) selected prior to the conjugation to the protein moiety. The actual molecular weight as determined by MS (electro-spray; see Table 1B).

The product was determined to be a mixture of approximately 87.8% Camptothecin-rvD-Asp-Suc-(Doc)₄-Aepa-D-Phe-c(Cys-Tyr-D-Trp-Lys-Abu-Cys)-Thr-NH₂ and 13.2% Camptothecin-rvAsp-Suc-(Doc)₄-Aepa-D-Phe-c(Cys-Tyr-D-Trp-Lys-Abu-Cys)-Thr-NH₂. The product of a second reaction was determined to be a mixture of approximately 87.3% Camptothecin-rvD-Asp-Suc-(Doc)₄-Aepa-D-Phe-c(Cys-Tyr-D-Trp-Lys-Abu-Cys)-Thr-NH₂ and 12.7% Camptothecin-rvAsp-Suc-(Doc)₄-Aepa-D-Phe-c(Cys-Tyr-D-Trp-Lys-Abu-Cys)-Thr-NH₂.

The skilled artisan would know that chiral column purification may be utilized to further isolate the rvL-Asp or rvD-Asp forms of the two conjugated peptides.

Example 5C

Preparation of Camptothecin-rvD-Asp-Suc-(Doc)₄-Aepa-D-Phe-c(Cys-Tyr-D-Trp-Lys-Abu-Cys)-Thr-NH₂

Step A. Synthesis of H-(Doc)₄-Aepa-D-Phe-Cys(Trt)-Tyr(tBu)-D-Trp(Boc)-Lys(Boc)-Abu-Cys(Trt)-Thr(tBu)-resin The protected peptide-resin was automatically synthesized on an Applied Biosystems® model 433A peptide synthesizer (Foster City, Calif.) using Fluorenylmethyloxycarbonyl (Fmoc) chemistry. A 1 mmol scale of Rink Amide MBHA® resin (4-methylbenzhydrylamine; Nova Biochem., La Jolla, Calif.) with a substitution of 0.72 mmol/g was used. Fmoc-8-amino-3,6-dioxaoctanoic acid (Fmoc-Doc-OH) was purchased from Chem-Impex International® (Wood Dale, Ill.). Fmoc-4(2-aminoethyl)-1-carboxymethyl-piperazine.2HCl (Fmoc-Aepa-OH) was purchased from Neosystem® (Strasbourg, France). Fmoc-D-Phe-OH, Fmoc-Cys(Trt)-OH, Fmoc-Tyr(tBu)-OH, Fmoc-D-Trp(Boc)-OH, Fmoc-Lys(Boc)-OH, Fmoc-Abu-OH, and Fmoc-Thr(tBu)-OH were purchased from AnaSpec® (San Jose, Calif.).

Prior to coupling, the Fmoc groups were removed by treatment with 20% piperidine in N-methylpyrrolidone (NMP) for 30 minutes. For each coupling step, the Fmoc amino acid (3 eq, 3 mmol) was first pre-activated by using 6 ml of 0.45M 2-(1-H-benzotriazole-1-yl)-1,1,2,3-tetramethyluronium-hexafluorophosphate/1-hydroxy-benzotriazole (HBTU/HOBT) in DMF. The activated amino acid ester, 3 ml of 2M diisopropylethylamine (DIEA) and 3 ml of NMP were added to the resin. The ABI 433A® peptide synthesizer was programmed to perform the following reaction cycle: (1) wash with NMP, (2) remove Fmoc protecting group with 20% piperidine in NMP for 30 minutes, (3) wash with NMP, and (4) double-couple with pre-activated amino acid for two times, one hour each.

The protected peptide-resin i.e., H-D-Phe-Cys(Trt)-Tyr(tBu)-D-Trp(Boc)-Lys(Boc)-Abu-Cys(Trt)-Thr(tBu)-Rink Amid MBHA, was then manually coupled to Fmoc-Aepa-OH and Fmoc-Doc-OH. Coupling to Fmoc-Aepa-OH was carried out by dissolving 2 equivalents of Fmoc-Aepa-OH, 1.8 equivalents of HATU, 2 equivalents of HOAT and 24 equivalents of DIEA in DMF and mixing for two minutes; the activated amino acid ester/DMF mixture was shaken with the protected peptide resin for two hours. An aliquot of the resin was subjected to a ninhydrin test which confirmed that the reaction was complete. The resin was washed with DMF and deprotected Fmoc with 25% piperidine in DMF for 30 minutes. After washing with DMF, the resin was coupled with Fmoc-Doc-OH by using DIC/HOBT as the coupling reagent. For each Fmoc-Doc-OH coupling, the resin was mixed with a solution containing 3.2 equivalents of Fmoc-Doc-OH in 0.4N HOBT/NMP and 5.3 equivalents of DIC in 0.4N DIC/DMF for one hour; the coupling reaction was repeated one time. The resin was washed with DMF and treated with 25% piperiden/DMF to remove the Fmoc-protecting group. After washing with DMF and DCM, the peptide-resin was ready to couple with the desired cytotoxic moiety.

Step B. Synthesis of Camptothecin-rvD-Asp(OtBu)-Succinic Acid

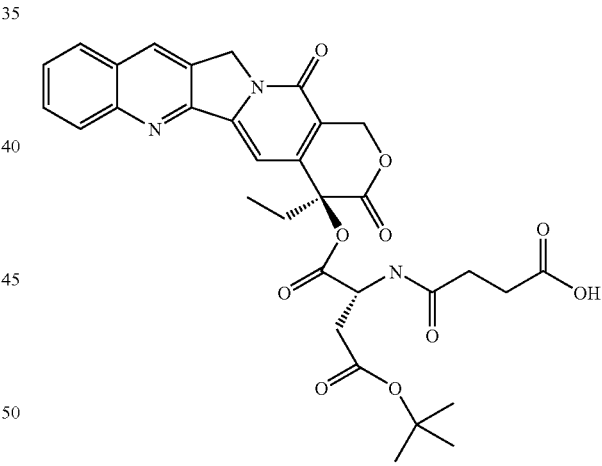

B-1. Synthesis of Camptothecin-rvD-Asp(OtBu)-NHBoc (2)

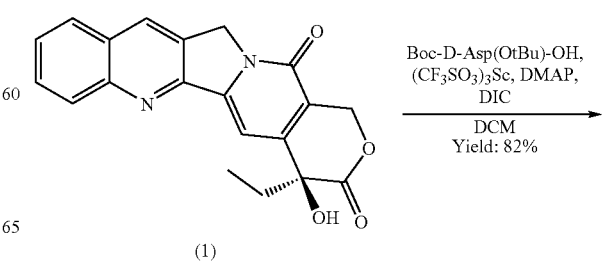

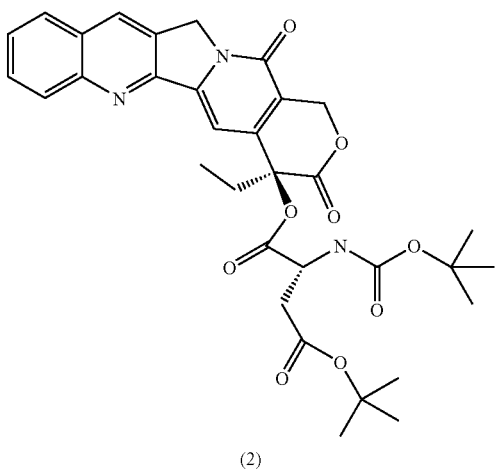

(2)

To an ice cooled suspension of Camptothecin (1) (1.006 g, 2.889 mmol), Boc-D-Asp(OtBu)-OH (2.51 g, 8.67 mmol), (Cf$_3$SO$_3$)$_3$Sc (0.855 g, 1.733 mmol) and DMAP (1.061 g, 8.667 mmol) in DCM (20 ml) was added followed by the addition of DIC (9.1 ml, 1.424 mmol). The reaction solution was stirred under a blanket of N$_2$ in a salt-ice bath for 0.5 h. After removal from the salt-ice bath, the reaction suspension was stirred and become a clear solution within 20 minutes. After one hour later, TLC (DCM/MeOH, v/v 9/1) analysis showed the reaction was done. The reaction mixture was diluted with DCM and washed successively with 10% citric acid (50 ml×3), saturated NaHCO$_3$ (50 ml×3) and brine (50 ml×3), dried over Na$_2$SO$_4$ and stripped down under vacuum. The crude product (3.19 g) was purified by crystallization from 20 ml of MeOH to give pure 1.4642 g product. The yield was 82%. The actual molecular weight of the camptothecin-rvD-Asp(OtBu)-NHBoc as determined by MS (electrospray) was 620, in keeping with calculated molecular weight 619.7.

B-2. Synthesis of Camptothecin-rvD-Asp(OtBu)-NH$_2$.HCl (3)

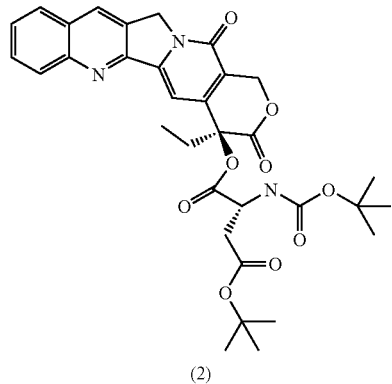

(2)

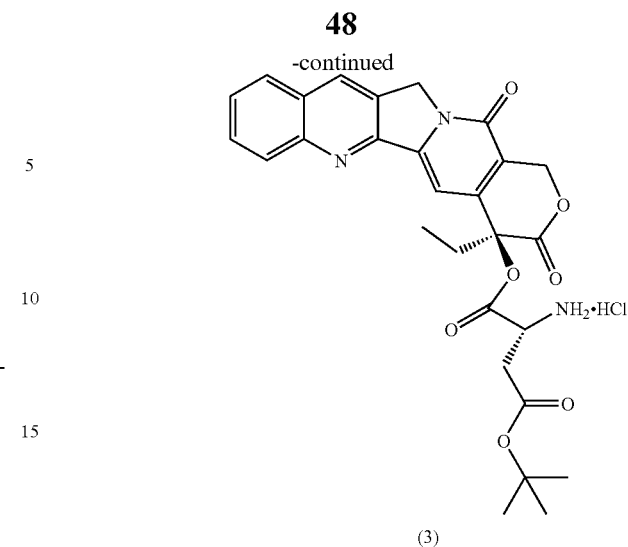

(3)

To a suspension of Camptothecin-rvD-Asp(OtBu)-NHBoc (4.89 g, 7.9 mmol) in tert-BuOH (48 ml) was added 4M HCl/dioxane (59 ml, 30 eq) with stirring. After the suspension became clear solution, it was stirred for 10 minutes. The reaction solution was diluted with 450 ml of ether and stirred for another 5 minutes. It was filtered. The filtered cake was washed thoroughly by ether. Yield was 100%. MS (electrospray) showed 520 (M+1), 464.2 (M−56) 1039.2 (2M+1), 1557.6 (M+1), which was in keeping with calculated molecular weight of 519.9. HPLC showed 92% purity with 8% of Camptothecin-rvAsp-NH$_2$.

B-3. Synthesis of Camptothecin-rvD-Asp(OtBu)-Succinic Acid (4)

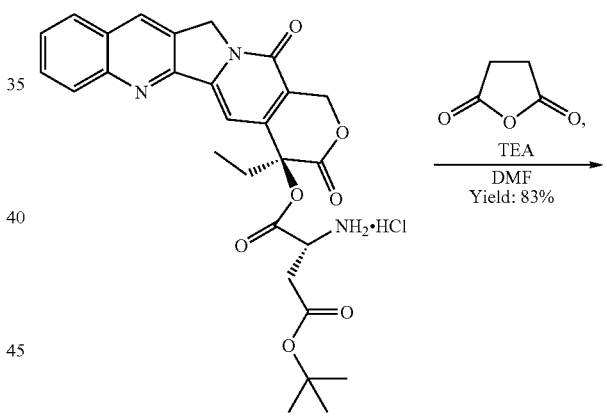

(3)

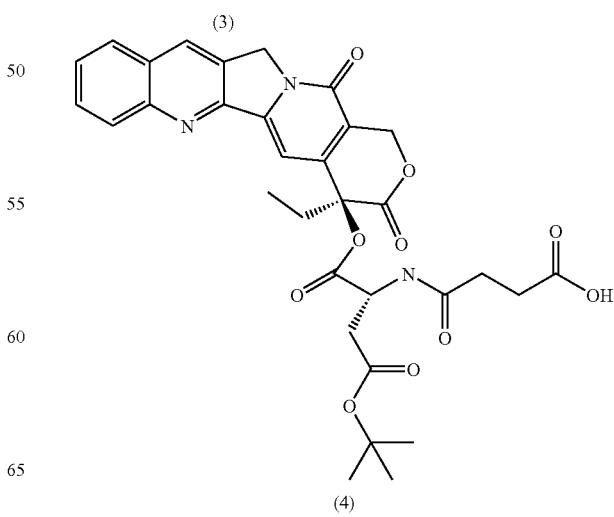

(4)

To a solution of Camptothecin-rvD-Asp(OtBu)-NH$_2$.HCl (4.48 g, 8.05 mmol) in DMF (95 ml) were successively added succinic anhydride (1.2 g, 12 mmol) and TEA (7.456 ml, 53.85 mmol). The mixture was stirred for 2 hours at room temperature and HPLC analysis indicated that the reaction was complete. The solution was evaporated under vacuum. The resulting residue was stirred with water for 1 h and precipitate was collected by filtration. After dried in oven (60° C.) under vacuum overnight, it provided 1.84 g product. Its actual molecular weight of Camptothecin-rvD-Asp(OtBu)-Succinic acid (4) as determined by MS (electro-spray) was 620.1 in keeping with calculated molecular weight 619.7. The yield was 47%.

Step C. Synthesis of Camptothecin-rvD-Asp-Suc-(Doc)$_4$-Aepa-D-Phe-c(Cys-Tyr-D-Trp-Lys-Abu Cys)-Thr-NH$_2$ A 0.8 mmol aliquot of the resin prepared according to section (A) was mixed with 20 ml DMF/DCM (1:1, v/v) containing camptothecin-rvD-Asp(OtBu)-succinic acid(4) (0.544 g, 0.88 mmol, 1.1 equivalents), DIC (1 ml, 8 equivalents), HOAt (0.217 g, 2 equivalents) and DIEA (4 ml, 20 equivalents) for 48 hours. The resin was drained and washed successively with DMF, MeOH and DCM. After air drying, the resin was cleaved in a mixture of TFA, H$_2$O and TIS (24 ml/2.2 ml/1.92 ml) for 2 hours. The resin was filtered off and the filtrate was poured into 300 ml of cold ether. The resulting precipitate was centrifuged and collected. The crude linear product was dissolved in a solvent system containing 350 ml of 5% AcOH and 60 ml of CH$_3$CN, to which 0.25N iodine solution in MeOH was added dropwise until a yellow color was maintained. The reaction solution was stirred for 1 hour, quenched using a few drops of 10% Na$_2$SSO$_3$ aqueous solution and then filtered. The filtrate was purified via reverse-phase preparative HPLC using a 4×43 cm column of C$_{18}$ DYNAMAX-100® A° (Varian, Walnut Creek, Calif.). The column was eluted with a linear gradient from 20% B to 45% B in 50 minutes, where A was 0.1% TFA in water and B was 0.1% TFA in CH$_3$CN. Fractions were analyzed by MS and those fractions containing the desired product were pooled and subjected to salt exchange. The pooled fractions were analyzed by MS and HPLC, and the fractions containing the pure product were pooled and lyophilized to dryness. The actual molecular weight of the camptothecin-rvD-Asp-Suc-(Doc)$_4$-Aepa-D-Phe-c(Cys-Tyr-D-Trp-Lys-Abu-Cys)-Thr-NH$_2$ as determined by MS (electro-spray) was 2327.3, in keeping with calculated molecular weight 2327.6 (see Table 1B). The yield was 13.9%.

Example 6

Preparation of a mixture of Camptothecin-rvD-Glu-Suc-(Doc)$_4$-Aepa-D-Phe-c(Cys-Tyr-D-Trp-Lys-Abu-Cys)-Thr-NH$_2$ and Camptothecin-rvGlu-Suc-(Doc)$_4$-Aepa-D-Phe-c(Cys-Tyr-D-Trp-Lys-Abu-Cys)-Thr-NH$_2$ The titled compound was synthesized substantially according to the procedure described in Example 1. The product was determined to be a mixture of approximately 17% Camptothecin-rvD-Glu-Suc-(Doc)$_4$-Aepa-D-Phe-c(Cys-Tyr-D-Trp-Lys-Abu-Cys)-Thr-NH$_2$ and approximately 83% Camptothecin-rvGlu-Suc-(Doc)$_4$-Aepa-D-Phe-c(Cys-Tyr-D-Trp-Lys-Abu-Cys)-Thr-NH$_2$.

Example 7

Preparation of Camptothecin-rvArg-Suc-(Doc)$_4$-Aepa-D-Phe-c(Cys-Tyr-D-Trp-Lys-Abu-Cys)-Thr-NH$_2$ The titled compound was synthesized substantially according to the procedure described in Example 1.

Example 8

Preparation of Camptothecin-rvDap(Z)-Suc-(Doc)$_4$-Aepa-D-Phe-c(Cys-Tyr-D-Trp-Lys-Abu-Cys)-Thr-NH$_2$ The titled compound was synthesized substantially according to the procedure described in Example 1.

Example 9

Preparation of Camptothecin-rvD-Dap(Z)-Suc-(Doc)$_4$-Aepa-D-Phe-c(Cys-Tyr-D-Trp-Lys-Abu-Cys)-Thr-NH$_2$ The titled compound was synthesized substantially according to the procedure described in Example 1.

Example 10

Preparation of Camptothecin-rvPhe-Suc-(Doc)$_4$-Aepa-D-Phe-c(Cys-Tyr-D-Trp-Lys-Abu-Cys)-Thr-NH$_2$ The titled compound was synthesized substantially according to the procedure described in Example 1.

Example 11

Preparation of Camptothecin-rvApn-Suc-(Doc)$_4$-Aepa-D-Phe-c(Cys-Tyr-D-Trp-Lys-Abu-Cys)-Thr-NH$_2$ The titled compound was synthesized substantially according to the procedure described in Example 1.

Example 12

Preparation of Camptothecin-rvAbu-Suc-(Doc)$_4$-Aepa-D-Phe-c(Cys-Tyr-D-Trp-Lys-Abu-Cys)-Thr-NH$_2$ The titled compound was synthesized substantially according to the procedure described in Example 1.

Example 13

Preparation of Camptothecin-rvD-Val-Suc-(Doc)$_4$-Aepa-D-Phe-c(Cys-Tyr-D-Trp-Lys-Abu-Cys)-Thr-NH$_2$ The titled compound was synthesized substantially according to the procedure described in Example 1.

Example 14

Preparation of Camptothecin-rvAla-Suc-(Doc)$_4$-Aepa-D-Phe-c(Cys-Tyr-D-Trp-Lys-Abu-Cys)-Thr-NH$_2$ The titled compound was synthesized substantially according to the procedure described in Example 1.

Example 15

Preparation of Camptothecin-rvVal-Suc-(Doc)$_4$-Aepa-D-Phe-c(Cys-Tyr-D-Trp-Lys-Abu-Cys)-Thr-NH$_2$ The titled compound was synthesized substantially according to the procedure described in Example 1.

Example 16

Preparation of Camptothecin-Glut-(Doc)$_4$-Aepa-D-Phe-c(Cys-Tyr-D-Trp-Lys-Abu-Cys)-Thr-NH$_2$ The titled compound was synthesized substantially according to the procedure described in Example 1.

Example 17

Preparation of Camptothecin-rvAnc-Suc-(Doc)$_4$-Aepa-D-Phe-cyclo(Cys-Tyr-D-Trp-Lys-Abu-Cys)-Thr-NH$_2$ The titled compound was synthesized substantially according to the procedure described in Example 1.

Example 18

Preparation of Camptothecin-rvAhp-Suc-(Doc)$_4$-Aepa-D-Phe-cyclo(Cys-Tyr-D-Trp-Lys-Abu-Cys)-Thr-NH$_2$ The titled compound was synthesized substantially according to the procedure described in Example 1.

Example 19

Preparation of SN38-rvGly-Suc-(Doc)$_4$-Aepa-D-Phe-c(Cys-Tyr-D-Trp-Lys-Abu-Cys)-Thr-NH$_2$ The titled conjugate was synthesized substantially according to the procedure described in synthesis of Example 1. Bz-SN38 was used as the cytotoxic moiety. The Bz-SN38-rvGly-Succinic acid portion of the molecule was synthesized using the procedure described in step B for synthesis of camptothecin-rvCha-succinic acid. After removing Bz protecting group by hydrogenation, the SN38-rvGly-succinic acid moiety was coupled to the desired peptide resin. The final product was found to be homogenous by HPLC analysis. The actual molecular weight as determined by MS (electro-spray) was 2315.6 consistent with the calculated molecular weight 2315.7.

Example 20

Preparation of Camptothecin-rvGly-Suc-(Doc)$_4$-Aepa-Nle-Gln-Trp-Ala-Val-β-Ala-His-Leu-Nle-NH$_2$ (SEQ ID NO:4)

The titled conjugate was synthesized substantially according to the procedure described in the synthesis of Example 1. The product was found to be homogenous using high performance liquid chromatography (HPLC). The actual molecular weight as determined by MS (electro-spray) was 2286.5 consistent with calculated molecular weight 2286.6.

Example 21

Preparation of Camptothecin-rvGly-Suc-(Doc)$_4$-Aepa-Ahx-Gln-Trp-Ala-Val-β-Ala-His-Leu-Nle-NH$_2$ (SEQ ID NO:5)

The titled compound was synthesized substantially according to the procedure described in Example 1.

Example 22

Preparation of Camptothecin-rvGly-Suc-(Doc)$_4$-Aepa-Leu-Gaba-Gln-Trp-Ala-Val-β-Ala-His-Leu-Nle-NH$_2$ (SEQ ID NO:6)

The titled compound was synthesized substantially according to the procedure described in Example 1.

Example 23

Preparation of Camptothecin-rvGly-Suc-(Doc)$_4$-Aepa-Gaba-Asn-Gln-Trp-Ala-Val-β-Ala-His-Leu-Nle-NH$_2$ (SEQ ID NO:7)

The titled compound was synthesized substantially according to the procedure described in Example 1.

Example 24

Preparation of Camptothecin-rvGly-Suc-(Doc)$_4$-Aepa-Apn-Asn-Gln-Trp-Ala-Val-β-Ala-His-Leu-Nle-NH$_2$ (SEQ ID NO:8)

The titled compound was synthesized substantially according to the procedure described in Example 1.

Example 25

Preparation of Camptothecin-rvGly-Suc-(Doc)$_4$-Lys-D-Ser-D-Tyr-Gln-Trp-Ala-Val-β-Ala-His-Leu-Nle-NH$_2$ The titled compound was synthesized substantially according to the procedure described in Example 1.

Example 26

Preparation of Camptothecin-rvGly-Suc-(Doc)$_4$-Arg-D-Ala-D-Tyr-Gln-Trp-Ala-Val-β-Ala-His-Leu-Nle-NH$_2$ The titled compound was synthesized substantially according to the procedure described in Example 1.

Example 27

Preparation of Camptothecin-rvGly-Suc-(Doc)$_4$-Aepa-D-Ser-D-Tyr-Gln-Trp-Ala-Val-β-Ala-His-Leu-Nle-NH$_2$ The titled compound was synthesized substantially according to the procedure described in Example 1.

Example 28

Preparation of Camptothecin-rvGly-Suc-(Doc)$_4$-Aepa-Gaba-D-Ser-D-Tyr-Gln-Trp-Ala-Val-β-Ala-His-Leu-Nle-NH$_2$ The titled compound was synthesized substantially according to the procedure described in Example 1.

Example 29

Preparation of Camptothecin-rvDAsp-Suc-(Peg3)$_3$-Aepa-DPhe-c(Cys-Tyr-DTrp-Lys-Abu-Cys)-Thr-NH$_2$ The titled compound was synthesized substantially according to the procedure described in Example 1.

Example 30

Preparation of Camptothecin-rvDAsp-Suc-Peg$_{11}$-Aepa-DPhe-c(Cys-Tyr-DTrp-Lys-Abu-Cys)-Thr-NH$_2$ The titled compound was synthesized substantially according to the procedure described in Example 1.

Example 31

Preparation of Camptothecin-rvDGlu-Suc-(Doc)$_4$-Aepa-DPhe-c(Cys-Tyr-DTrp-Lys-Abu-Cys)-Thr-NH$_2$ The titled compound was synthesized substantially according to the procedure described in Example 1.

The estimated molecular weights, the actual molecular weights and the purity of the compounds of Examples 1 to 31 are found in Tables 1A, 1B and 1C.

TABLE 1A

| Example | Purity (%) | Real MW | Est MW |
|---|---|---|---|
| 1 | 99 | 2364.6 | 2365.74 |
| 2 | 99 | 2837.9 | 2837.93 |
| 3 | 99 | 2547.6 | 2547.61 |
| 4 | 99 | 2467.8 | 2467.79 |
| 6 | 94.2 | 2340.8 | 2341.63 |
| 7 | 92.3 | 2367.9 | 2368.71 |
| 8 | 99 | 2431.9 | 2432.75 |
| 9 | 99 | 2431.9 | 2432.75 |
| 10 | 99 | 2358.6 | 2359.70 |
| 11 | 99 | 2310.8 | 2311.65 |
| 12 | 99 | 2296.9 | 2297.62 |
| 13 | 99.9 | 2310.9 | 2311.65 |
| 14 | 99.9 | 2282.9 | 2283.60 |
| 15 | 99 | 2310.9 | 2311.65 |
| 16 | 96.8 | 2226.0 | 2226.55 |
| 17 | 99 | 2367.1 | 2367.76 |
| 18 | 99 | 2339.2 | 2339.71 |
| 19 | 98.6 | 2313.2 | 2313.62 |
| 20 | 99 | 2286.5 | 2286.60 |
| 21 | 99 | 2286.5 | 2286.60 |
| 22 | 99 | 2372.0 | 2371.71 |
| 23 | 99 | 2372.8 | 2372.69 |
| 24 | 99 | 2386.7 | 2386.68 |
| 25 | 99.9 | 2382.1 | 2382.64 |
| 26 | 97.6 | 2394.2 | 2394.66 |
| 27 | 99.9 | 2423.3 | 2423.69 |
| 28 | 99.9 | 2508.5 | 2508.50 |

TABLE 1B

| Example | Purity (%) | Real MW | Est MW | Ratio of D/L isomers |
|---|---|---|---|---|
| 5A | 99.9 | 2327.5 | 2327.61 | 58.2:41.8 |
| 5B | 97.8 | 2327.3 | 2327.61 | 87.8:13.2 |
| 5C | 99.0 | 2327.3 | 2327.61 | 96.8:3.2 |

TABLE 1C

| Example | Purity (%) | Real MW | Est MW |
|---|---|---|---|
| 29 | 99.9 | 2314.40 | 2314.61 |
| 30 | 99.9 | 2346.60 | 2346.69 |
| 31 | 100 | 2341.80 | 2341.63 |

Biological Assays

Half-Life Determinations

Samples containing approximately 50 µg/ml up to and including approximately 500 µg/ml of test compound according to Formula IA or IB or II was added to 450 µl human or mouse plasma, vortexed briefly and incubated at 37° C. At various time intervals, e.g., 0, 0.5, 1, 2, 4, 6, 8, 24, 36 and 48 hours, 50 µl of the compound-plasma mixture was added to 150 µl acetonitrile in a microcentrifuge tube. The mixture was vortexed, centrifuged for 5 minutes at 10K RPM, and 135 µl of supernatant was transferred to an injection vial. The recovered supernatant was analyzed by using a liquid chromatography-mass spectrophotometer system (LC-MS) consisting of a Finnigan Deca XP® mass spectrometer with an ESI probe at the positive ion mode. HPLC separation was carried out on a Luna 3µ C8 (2)® 3×50 mm column with a gradient decreasing from 100% A to 80% B for 10 minutes at a flow rate of 0.25 ml/min. Buffer A was 0.1% acetic acid in water and buffer B was 0.1% acetic acid acetonitrile. Half-life data are reported in Tables 2A and 2B.

TABLE 2A

| Example | Half-life in Mouse Plasma (hrs) | Half-life in Human Plasma (hrs) | In vivo mouse PK T½ (hrs) |
|---|---|---|---|
| 1 | 2.0 | 4.7 | 1.5 |
| 2 | 4.6 | 2.2 | |
| 3 | 5.7 | 3.8 | |
| 4 | 4.4 | 3.2 | |
| 6 | 13.1 | 10.7 | |
| 7 | 1.2 | 1.5 | |
| 8 | 2.2 | 0.7 | |
| 9 | 1.7 | 0.7 | |
| 10 | 2.4 | 0.3 | |
| 11 | 3.7 | 5.0 | |
| 12 | 6.0 | 0.7 | |
| 13 | 7.7 | 0.3 | |
| 14 | 4.6 | 1.3 | |
| 15 | 5.0 | 0.4 | |
| 16 | 4.2 | 3.6 | |
| 17 | 15.6 | 28.6 | |
| 18 | 16.2 | 8.0 | |
| 19 | 2.6 | 6.9 | 1.2 |
| 20 | 2.8 | 4.8 | |
| 21 | 5.4 | 3.2 | |
| 22 | 2.1 | 1.8 | |
| 23 | 2.9 | 4.2 | |
| 24 | 2.6 | 4.6 | |
| 25 | 2.6 | 2.4 | |
| 26 | 1.8 | 1.4 | |
| 27 | 3.8 | 4.5 | |
| 28 | 2.9 | 1.9 | |

TABLE 2B

| Example | Half-life in Mouse Plasma (hrs) | Half-life in Human Plasma (hrs) | Ratio of D/L isomers |
|---|---|---|---|
| 5A | 20.8 | 10.8 | 58.2:41.8 |
| 5B | 27.5 | 10.3 | 87.8:13.2 |

TABLE 2C

| Example | Half-life in Mouse Plasma (hrs) | Half-life in Human Plasma (hrs) |
|---|---|---|
| 29 | 44.1 | 9.3 |

Somatostatin Receptor-Radioligand Binding Assays

Membranes for in vitro receptor binding assays were obtained by homogenizing (Polytron setting 6, 15 sec) CHO-K1 cells expressing human somatostatin receptor subtypes hSSTR-1, hSSTR-2, hSSTR-3, hSSTR-4 or hSSTR-5 in ice-cold 50 mM Tris-HCl. The homogenized cells were centrifuged twice at 39,000 g for 10 minutes with an intermediate resuspension in fresh buffer. The final pellets were resuspended in 10 mM Tris-HCl to prepare the cell membrane homogenate for use in the binding assay.

For the hSSTR-1, hSSTR-3, and hSSTR-4 assays, aliquots of the membrane preparations were incubated for 90 minutes at 25° C. with 0.05 nM [$^{125}$I-Tyr11]SRIF-14 in 50 mM HEPES (pH 7.4) buffer containing 0.2% BSA and 5 mM $MgCl_2$. The final assay volume was 0.3 ml. For the hSSTR-2 and hSSTR-5 assays, [$^{125}$I]-[4-(2-hydroxyethyl)]-1-piperazinylacetyl-D-Phe-c(Cys-Tyr-D-Trp-Lys-Abu-Cys)-Thr-$NH_2$ (0.05 nM) and [$^{125}$I]-D-Phe-c(Cys-Tyr-D-Trp-Lys-Val-Cys)-Thr-$NH_2$ were employed as the radioligands, respectively.

The cell membrane homogenate was incubated with the radioligands for 90 minutes at 25° C. The incubations were terminated by rapid filtration through GF/C filters pre-soaked in 0.3% polyethylenimine using a Brandel® filtration manifold (Gaithersberg, Md., U.S.A.). Each tube and filter was washed three times with 5-ml aliquots of ice-cold buffer. Specific binding was defined as the total radioligand bound minus that bound in the presence of 1000 nM SRIF-14 (for hSSTR-1, hSSTR-3, hSSTR-4 or hSSTR-5), or 1000 nM DPhe-c(Cys-Tyr-D-Trp-Lys-Abu-Cys)-Thr-$NH_2$ for hSSTR-2. Specific binding data are reported in Tables 3A and 3B.

TABLE 3A

| Example # | Ki (nM) hSSTR1 ± (SEM)* | Ki (nM) hSSTR2 ± (SEM) | Ki (nM) hSSTR3 ± (SEM) | Ki (nM) hSSTR4 ± (SEM) | Ki (nM) hSSTR5 ± (SEM) |
|---|---|---|---|---|---|
| 1 | 1000** | 0.54 (0.04) | 155.5 (56.4) | 1000 | 211 |
| 2 | 1000 | 0.36 (0.25) | 125 | 1000 | 3 (0.47) |
| 3 | 1000 | 0.10 (0.02) | 94 | 1000 | 3.86 (1.27) |
| 4 | 1000 | 9.38 (5.03) | 1000 | 1000 | 480.9 (96) |
| 6 | 1000 | 4.70 (0.17) | 781.5 (218.5) | 1000 | ND |
| 7 | 1000 | 1.09 (0.24) | 479.5 (366.5) | 1000 | ND |
| 8 | 1000 | 1.83 (0.80) | 420.5 (295.5) | 1000 | ND |
| 9 | 1000 | 2.35 (0.72) | 892 (108) | 1000 | ND |
| 10 | 1000 | 1.73 (0.90) | 235 (83) | 1000 | ND |
| 11 | 1000 | 1.89 (1.17) | 1090.5 (537.5) | 1000 | ND |
| 12 | 1000 | 1.23 (0.11) | 909.3 (217.8) | 1000 | ND |
| 13 | 1000 | 0.92 (0.11) | 510 (128.8) | 1000 | ND |
| 14 | 1000 | 1.20 (0.10) | 1000 | 1000 | ND |
| 15 | 1000 | 1.03 (0.01) | 850 (150) | 1000 | ND |
| 16 | 1000 | 0.75 (0.28) | 915.2 (84.8) | 1000 | ND |
| 17 | 1000 | 0.38 (0.02) | 576.5 (423.5) | ND | 1000 |
| 18 | 1000 | 0.37 (0.16) | 682.5 (317.5) | ND | 1000 |
| 19 | 1000 | 1.78 | 627 | 188 | 4.33 |

*SEM = standard error
**value of 1000 indicates a value of at least 1000
ND = not determined

TABLE 3B

| Example # | Ki (nM) hSSTR1 ± (SEM)* | Ki (nM) hSSTR2 ± (SEM) | Ki (nM) hSSTR3 ± (SEM) | Ki (nM) hSSTR4 ± (SEM) | Ki (nM) hSSTR5 ± (SEM) |
|---|---|---|---|---|---|
| 5A' | 1000** | 2.94 (2.44) | 1000 | 1000 | 842 |

*SEM = standard error
**value of 1000 indicates a value of at least 1000
A' = racemic components to be determined

TABLE 3C

| Example # | Ki (nM) hSSTR1 ± (SEM)* | Ki (nM) hSSTR2 ± (SEM) | Ki (nM) hSSTR3 ± (SEM) | Ki (nM) hSSTR4 ± (SEM) | Ki (nM) hSSTR5 ± (SEM) |
|---|---|---|---|---|---|
| 29 | 1000** | 3.32 (0.67) | ND | ND | ND |
| 30 | 1000** | 3.04 (0.94) | ND | ND | ND |
| 31 | 1000** | 0.27 90.08) | ND | ND | ND |

*SEM = standard error
**value of 1000 indicates a value of at least 1000
ND = not determined Bombesin/GRP Radioligand Binding Membranes were prepared for radioligand binding studies by homogenization of AR42J rat pancreas cells expressing the native bombesin/GRP receptor in 20 ml of ice-cold 50 mM Tris-HCl with a Brinkman Polytron® (Westbury, N.Y., U.S.A.) at settings of 6, 15 seconds. The homogenates were washed twice by centrifugation (39,000 g/10 minutes) and the final pellets were resuspended in 50 mM Tris-HCl containing 2.5 mM $MgCl_2$ and 0.1% BSA. For the assay, aliquots of membrane homogenate (0.4 ml) were incubated with 0.05 nM [$^{125}$I-Tyr4]bombesin (2200 Ci/mmol) (New England Nuclear®, Boston, Mass., U.S.A.) with and without 0.05 ml of unlabeled competing test peptides. After a 30 minute incubation period at 4° C., the bound [$^{125}$I-Tyr4]bombesin was separated from the free bombesin by rapid filtration through GF/B filters (Brandel®, Gaithersburg, Md., U.S.A.) which had been previously soaked in 0.3% polyethyleneimine. The filters were then washed three times with 5-ml aliquots of ice-cold 50 mM Tris-HCl. The bound radioactivity trapped on the filters was counted by gamma spectrometry (Wallac LKB®, Gaithersburg, Md., U.S.A.). Specific binding was defined as the total [$^{125}$I-Tyr4]bombesin bound minus that bound in the presence of 1000 nM bombesin (Bachem®, Torrence, Calif., U.S.A>). Specific binding data are reported in Table 4.

TABLE 4

| Example # | Ki (nM) bombesin receptor ± (SEM) |
|---|---|
| 20 | 4.57 (0.82) |
| 21 | 1.90 (0.41) |
| 22 | 18.22 (3.59) |
| 23 | 7.65 (2.58) |
| 24 | 4.07 (1.15) |
| 25 | 1.45 (0.37) |
| 26 | 1.10 (0.32) |
| 27 | 3.96 (0.69) |
| 28 | 4.82 (1.77) |

In Vitro Growth Assays

For the in vitro proliferation assays, cultured CHO-K1 cells or CHO-K1 cells expressing the hSSTR-2 receptor are seeded into plastic 24-well plates in RPMI 1640 Medium (DMEM) containing 10% fetal bovine serum (FBS) at a density of approximately 104 cells/well/1.0 ml. The test peptides are added at the desired concentration and maintained in culture (5% $CO_2$, 37° C., humidified air) for one to three days. The cells are rinsed with serum-free RPMI media, trypsinized, resuspended RPMI 1640 (+10% FBS), and counted using a Coulter Counter at 1:20 dilution.

In Vivo Growth Assays

Female NCr-nude mice of 6-8 weeks of age were fed ad libitum water (reverse osmosis, 0.17% Cl) and an autoclaved standard rodent diet (NIH31®; 18% protein, 5% fat, 5% fiber, 8% ash and 3% minerals). The mice were housed in microisolators on a 12-hour light cycle at 22° C. (72° F.) and 40%-60% humidity.

Tumors for implantation were derived from human NCI-H69 cells which is a small cell lung carcinoma tumor cell line which expresses somatostatin type-2 receptors. Mice were implanted subcutaneously in the flank with 5×10$^6$ cells of NCI-H69 cells along with an equal volume of Matrigel® Matrix (BD Biosciences, San Jose, Calif., U.S.A.), a solubilized basement membrane preparation extracted from EHS mouse sarcoma, a tumor rich in ECM proteins. The tumors were monitored initially twice weekly and then daily as the neoplasms reached the desired size of approximately 100 mm$^3$, (100 mg). When the small cell lung carcinomas attained the desired size in calculated tumor weight, the animals were pair-matched on Day 1 into various treatment groups. The estimated tumor weight was calculated using the formula:

$$\text{Tumor weight (mg)} = \frac{w^2 \times l}{2}$$

where w=width and l=length, both measured in mm, of a small cell lung carcinoma.

Animals with tumors were then subject to either no treatment at all, treatment with a vehicle control (either saline or water), treatment with a camptothecin only control (7.5 mg/kg) or treatment with a compound according to Formula I or II as discussed above. All treatments were administered intravenously. The results of the in vim tumor studies are reported in Table 5 and FIG. 1.

Figure 2:
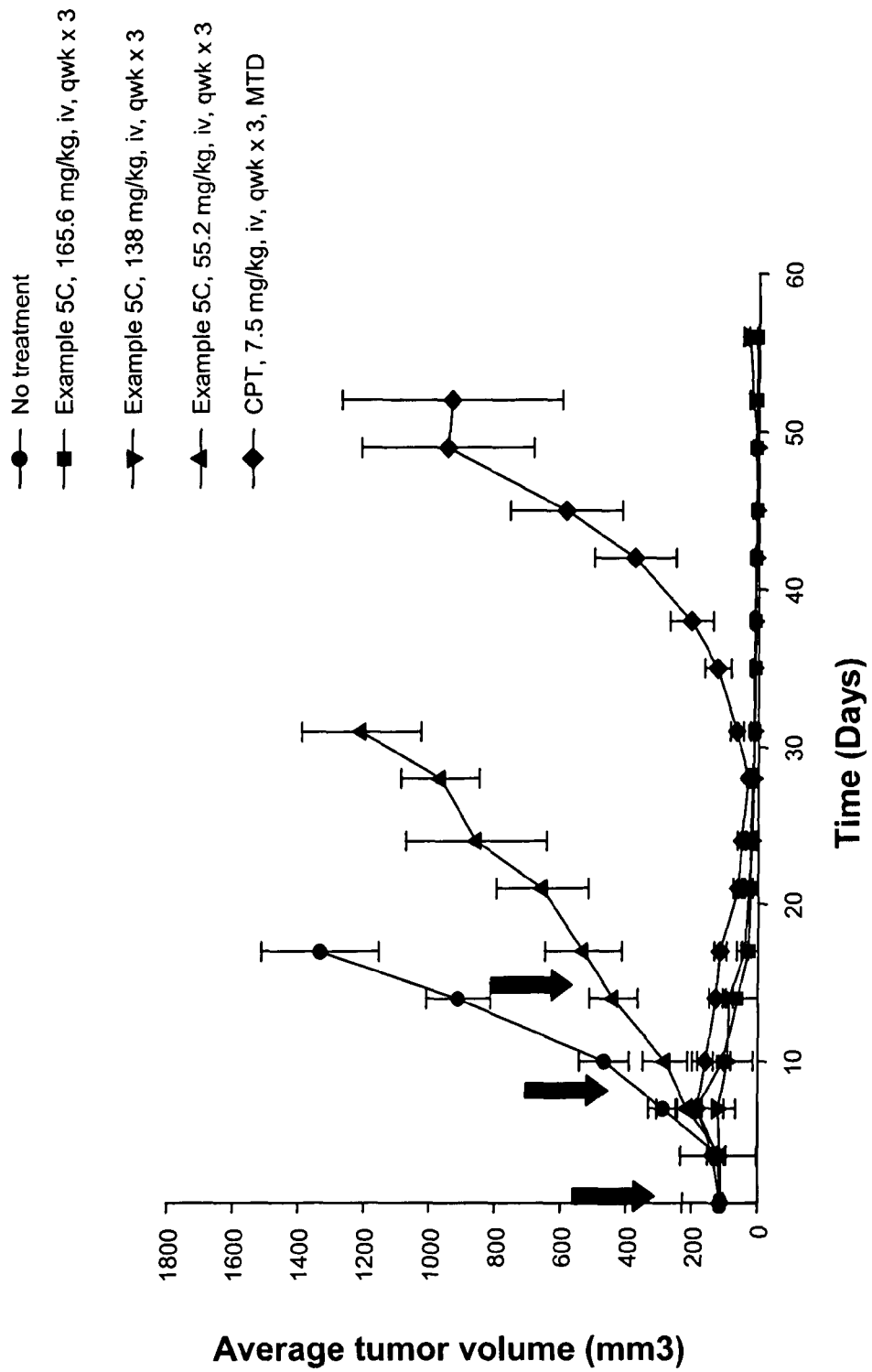
FIG. 2: Effects of Example 5C against tumor model human chronic myelogenous leukemia K562 in female athymic nude mice. Suppression of tumor growth in vivo in mice (qwk×3, i.v. schedule; HCML K562 xenograft model) untreated (circle symbol) treated with 165.6 mg/kg (square symbol), 138 mg/kg (downward triangle), 55.2 mg/kg (upward triangle) Example 5C or 7.5 mg/kg camptothecin (diamond symbol).

In other experiments, animals were implanted with human xenografts derived from NCI-H345 cells (human small cell lung carcinoma; see FIG. 2), A549 cells (non-small cell lung carcinoma), MDA-MB-231 cells (breast cancer) and K562 cells (human chronic myelogenous leukemia; see FIG. 3) and then subjected to treatment with the compounds of Formula I or II and the appropriate controls as described herein. As seen in FIGS. 2 and 3, the compound of Example 5C suppressed growth of small cell lung carcinoma and Human chronic myelogenous leukemia xenografts in mice.

TABLE 5A

NCI-H69 cells

| Example # | Treatment concentration (mg/Kg) | Relative to camptothecin treatment (7.5 mg/Kg) | Relative to vehicle treatment |
|---|---|---|---|
| 1 | 112 mg/Kg | 9X reduction | 16X reduction |
| 2 | ND | ND | ND |
| 3 | ND | ND | ND |
| 4 | ND | ND | ND |
| 6 | 111 mg/Kg | 1.5X reduction | 2.5X reduction |
| 7 | 27.75 mg/Kg | 3.5X reduction | 8X reduction |
| 8 | ND | ND | ND |
| 9 | ND | ND | ND |
| 10 | ND | ND | ND |
| 11 | 109.8 mg/Kg | 1.5X increase** | ⅓X increase |
| 12 | 109.2 mg/Kg | 18X reduction | 32X reduction |
| 13 | 109.8 mg/Kg | 4X increase | Same |
| 14 | 27.15 mg/kg | 4X reduction | 16X reduction |
| 15 | 109.8 mg/kg | 2X increase | 2X reduction |
| 16 | 26.5 mg/Kg | 3X increase | Same |
| 17 | 112.2 mg/Kg | 3.5X increase | Same |
| 18 | 55.5 mg/Kg | 3.5X increase | 1X reduction |

*approximate fold reduction in tumor size as compared to camptothecin or vehicle treatments
**approximate fold increase in tumor size as compared to camptothecin or vehicle treatments

TABLE 5B

NCI-H69 cells

| Example # | Treatment concentration (mg/Kg) | Relative to camptothecin treatment (7.5 mg/Kg) | Relative to vehicle treatment | Ratio of D/L isomers |
|---|---|---|---|---|
| 5A' | 110.4 mg/Kg | 2X reduction* | 4X reduction | — |
| 5B | 165 mg/kg | 5X reduction | 20X reduction | 87.8:13.2 |
| 5C | 165 mg/kg | 5X reduction | 20X reduction | 96.8:3.2 |

*approximate fold reduction in tumor size as compared to camptothecin or vehicle treatments
**approximate fold increase in tumor size as compared to camptothecin or vehicle treatments
A' = racemic components to be determined As evidenced by FIG. 1 and Table 5B, Example 5, as indicated above, reduced the growth of treated NCI-H69 tumor cells.

Some of the compounds of the instant invention have at least one asymmetric center. Additional asymmetric centers may be present in the molecule depending upon the nature of the various substituents of the molecule. Each such asymmetric center will produce two optical isomers and it is intended that all such optical isomers, as separated, pure or partially purified optical isomers, mixtures or diastereomeric mixtures thereof, are included within the scope of the instant invention.

The compounds of the instant invention generally can be provided in the form of their pharmaceutically acceptable acid addition salts, such as the salts derived from using inorganic and organic acids. Examples of such acids are hydrochloric, nitric, sulfuric, phosphoric, formic, acetic, trifluoro-acetic, propionic, maleic, succinic, D-tartaric, L-tartaric, malonic, methane sulfonic and the like. In addition, certain compounds containing an acidic function such as a carboxy can be isolated in the form of their inorganic salt in which the counter-ion can be selected from sodium, potassium, lithium, calcium, magnesium and the like, as well as from organic bases.

The pharmaceutically acceptable salts can be formed by taking about 1 equivalent of a compound of the invention and contacting it with about 1 equivalent or more of the appropriate corresponding acid of the salt which is desired. Work-up and isolation of the resulting salt is well-known to those of ordinary skill in the art.

The compounds of this invention can be administered by oral, parenteral (e.g., intramuscular, intraperitoneal, intravenous or subcutaneous injection, or implant), nasal, vaginal, rectal, sublingual or topical routes of administration and can be formulated with pharmaceutically acceptable carriers to provide dosage forms appropriate for each route of administration. Accordingly, the present invention features pharmaceutical compositions comprising, as an active ingredient, at least one compound of the invention in association with a pharmaceutically acceptable carrier.

Solid dosage forms for oral administration include capsules, tablets, pills, powders and granules. In such solid dosage forms, the active compound is admixed with at least one inert pharmaceutically acceptable carrier such as sucrose, lactose or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

In general, a therapeutically effective dose of an active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment, all of which are within the realm of knowledge of one of ordinary skill in the art. Generally, dosage levels of between 0.0001 to 100 mg/kg of body weight daily are administered to humans and other animals, e.g., mammals.

Preferred dosage ranges are from 0.01 to 10.0 mg/kg of body weight. Such dosages may be administered, for example, daily as a single dose or divided into multiple doses.

Other Embodiments

Various modifications and variations of the described method and system of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of medicine, immunology, pharmacology, endocrinology or related fields are intended to be within the scope of the invention.

All publications mentioned in this specification are herein incorporated by reference to the same extent as if the disclosure of each independent publication was explicitly provided herein.

We claim:

1. A compound according to Formula (IA):

$$A\text{-}B\text{-}C\text{-}E \qquad (IA)$$

wherein:

A is camptothecin or a derivative thereof;

B is, rvAhp, rvAla, rvAnc, rvApn, rvArg, rvAsp, rvCha, rvDap(Z), rvGlu, or rvPhe;

C is $D^1$-$D^2$-$D^3$-$D^4$ wherein $D^1$ is glutaryl, succinyl, or deleted, $D^2$ is $(Doc)_m$ wherein m is, independently for each occurrence thereof, 4, 5 or 6 or [Peg]x, wherein x is, independently for each occurrence thereof, 0-100;

$D^3$ is $(Aepa)_n$ wherein n is, independently for each occurrence thereof, 0 or 1; and $D^4$ is D-Phe or Lys-D-Tyr-D-Tyr;

E is a somatostatin analog of the formula $c(Cys\text{-}A^2\text{-}A^3\text{-}D\text{-}Trp\text{-}Lys\text{-}A^6\text{-}Cys)\text{-}A^8\text{-}R$ wherein $A^2$ is Phe or deleted;

$A^3$ is Phe, 3-(I)Tyr or Tyr, $A^6$ is Abu, Thr or deleted;

$A^8$ is Thr or deleted; and

R is $NH_2$ or OH;

or a pharmaceutically acceptable salt thereof.

2. A compound according to claim 1, wherein said camptothecin derivative is selected from the group consisting of:

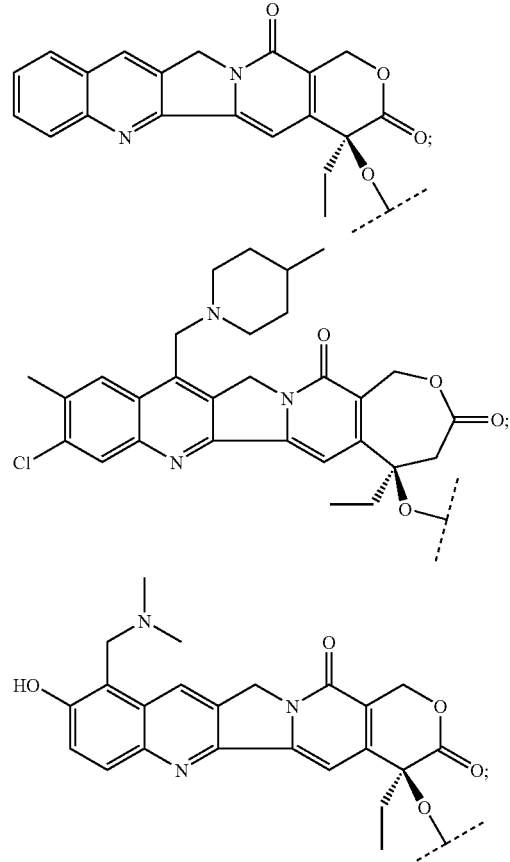

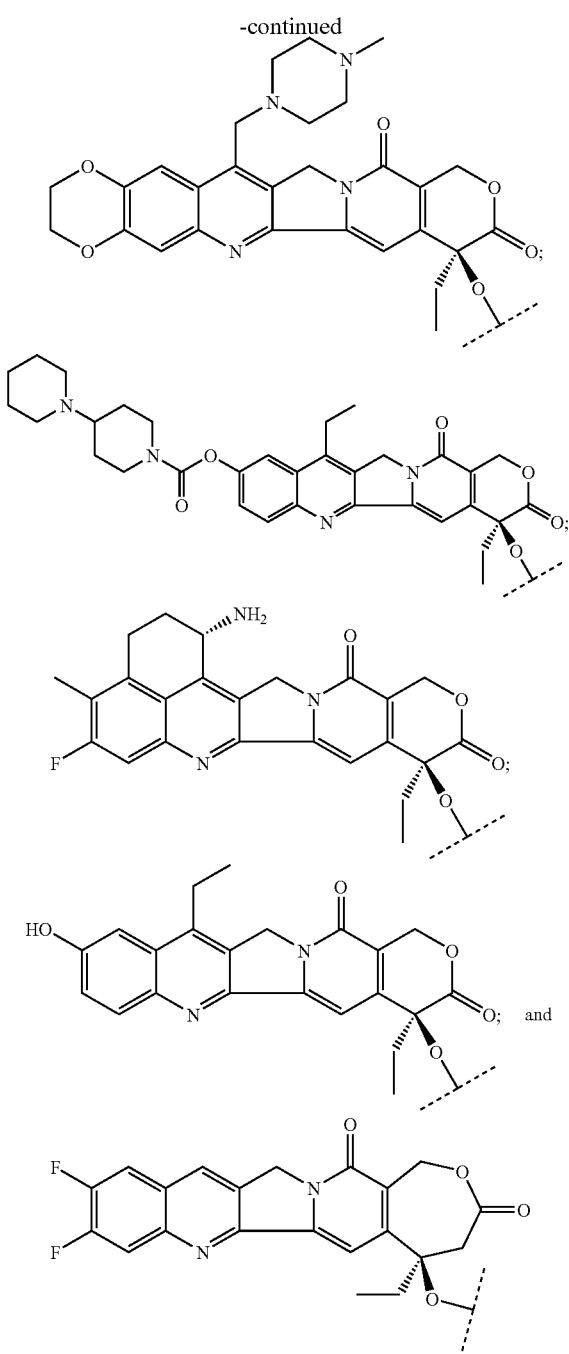

wherein "----" indicates the point of attachment of said camptothecin derivative to B-C-E; or a pharmaceutically acceptable salt thereof.

3. A compound according to claim 1, wherein said somatostatin analog is selected from the group consisting of c(Cys-3-(I)Tyr-D-Trp-Lys-Abu-Cys)-Thr-NH$_2$, c(Cys-Phe-Phe-D-Trp-Lys-Thr-Cys)-NH$_2$ and c(Cys-Tyr-D-Trp-Lys-Abu-Cys)-Thr-NH$_2$; or a pharmaceutically acceptable salt thereof.

4. A compound according to claim 3, wherein said compound is selected from the group consisting of:

Camptothecin-rvAsp-Suc-(Doc)$_4$-Aepa-D-Phe-c(Cys-Tyr-D-Trp-Lys-Abu-Cys)-Thr-NH$_2$;
Camptothecin-rvGlu-Suc-(Doc)$_4$-Aepa-D-Phe-c(Cys-Tyr-D-Trp-Lys-Abu-Cys)-Thr-NH$_2$;
Camptothecin-rvArg-Suc-(Doc)$_4$-Aepa-D-Phe-c(Cys-Tyr-D-Trp-Lys-Abu-Cys)-Thr-NH$_2$;
Camptothecin-rvDap(Z)-Suc-(Doc)$_4$-Aepa-D-Phe-c(Cys-Tyr-D-Trp-Lys-Abu-Cys)-Thr-NH$_2$;
Camptothecin-rvCha-Suc-(Doc)$_4$-Aepa-D-Phe-c(Cys-Tyr-D-Trp-Lys-Abu-Cys)-Thr-NH$_2$;
Camptothecin-rvPhe-Suc-(Doc)$_4$-Aepa-D-Phe-c(Cys-Tyr-D-Trp-Lys-Abu-Cys)-Thr-NH$_2$;
Camptothecin-rvApn-Suc-(Doc)$_4$-Aepa-D-Phe-c(Cys-Tyr-D-Trp-Lys-Abu-Cys)-Thr-NH$_2$;
Camptothecin-rvAla-Suc-(Doc)$_4$-Aepa-D-Phe-c(Cys-Tyr-D-Trp-Lys-Abu-Cys)-Thr-NH$_2$;
Camptothecin-Glut-(Doc)$_4$-Aepa-D-Phe-c(Cys-Tyr-D-Trp-Lys-Abu-Cys)-Thr-NH$_2$;
Camptothecin-rvAnc-Suc-(Doc)$_4$-Aepa-D-Phe-cyclo(Cys-Tyr-D-Trp-Lys-Abu-Cys)-Thr-NH$_2$;
Camptothecin-rvAhp-Suc-(Doc)$_4$-Aepa-D-Phe-cyclo(Cys-Tyr-D-Trp-Lys-Abu-Cys)-Thr-NH$_2$;
or a pharmaceutically acceptable salt thereof.

5. A compound according to claim 4, wherein said compound comprises the formula according to:

Camptothecin-rvAsp-Suc-(Doc)$_4$-Aepa-D-Phe-c(Cys-Tyr-D-Trp-Lys-Abu-Cys)-Thr-NH$_2$;
or a pharmaceutically acceptable salt thereof.

6. A pharmaceutical composition comprising an effective amount of a compound according to claim 1 or a pharmaceutically acceptable salt thereof and a pharmaceutically acceptable carrier.

7. A method of treating a disease or condition in a subject in need thereof, said method comprising administering to said subject a therapeutically effective amount of a compound according to claim 1, a pharmaceutically acceptable salt thereof, or a pharmaceutical composition thereof, wherein said a disease or condition is characterized by undesired proliferation of cells that express one or more somatostatin receptors.

8. A method of decreasing tumor size in a subject in need thereof comprising administering a therapeutically effective amount of a compound according to claim 1, a pharmaceutically acceptable salt thereof, or a pharmaceutical composition thereof, wherein said therapeutically effective amount is that amount which decreases the size of said tumor in said subject.

9. A method of inhibiting the undesired proliferation of tumor cells in a subject in need thereof comprising administering a therapeutically effective amount of a compound according to claim 1, a pharmaceutically acceptable salt thereof, or a pharmaceutical composition thereof, wherein said therapeutically effective amount is that amount which inhibits the undesired proliferation of said tumor cells in said subject.

10. A method according to claim 7, wherein said a disease or condition is a type of cancer, wherein said cancer is selected from the group consisting of neuroendocrine tumors, fibrosis, benign prostatic hyperplasia, atherosclerosis, restenosis, breast cancer, colon cancer, pancreas cancer, prostate cancer, lung cancer, small cell lung cancer, ovarian cancer, epidermal cancer, non-Hodgkin's lymphoma, Hodgkin's lymphoma, leukemia, hematopoietic cancer, adrenal medullary tumors pheochromocytoma, neuroblastoma, ganglioneuroma, gastroenteropancreatic tumors, glucagonoma, vasoactiveintestinal polypeptide secreting tumor, non-functioning GEP tumors, paraganglioma, pituitary ademona, astrocytomas, benign and malignant bone tumors, differentiated thyroid carcinoma, papillary thyroid carcinoma, follicular thyroid carcinoma, Hurthle cell thyroid carcinoma, meningioma, and non-small cell lung cancer.

11. A method according to claim 7, wherein said cancer is prostate cancer.

12. A compound according to Formula (IB):

A-B-C-E (IB)

wherein:
A is camptothecin or a derivative thereof;
B is rvD-Ala, rvD-Arg, rvD-Asp, rvD-Cha, rvD-Dap(Z), rvD-Glu or rvD-Phe;
C is $D^1$-$D^2$-$D^3$-$D^4$ wherein
$D^1$ is glutaryl, succinyl or deleted;
$D^2$ is $(Doc)_m$ wherein m is, independently for each occurrence thereof,
4, 5 or 6 or [Peg]x, wherein x is, independently for each occurrence thereof, 0-100;
$D^3$ is $(Aepa)_n$ wherein n is, independently for each occurrence thereof, 0 or 1; and
$D^4$ is D-Phe or Lys-D-Tyr-D-Tyr;
E is a somatostatin analog of the formula c(Cys-$A^2$-$A^3$-D-Trp-Lys-$A^6$-Cys)-$A^8$-R wherein $A^2$ is Phe or deleted;
$A^3$ is Phe, 3-(I)Tyr or Tyr,
$A^6$ is Abu, Thr or deleted;
$A^8$ is Thr or deleted; and
R is $NH_2$ or OH;
or a pharmaceutically acceptable salt thereof.

13. A compound according to claim 12, wherein said camptothecin derivative is selected from the group consisting of:

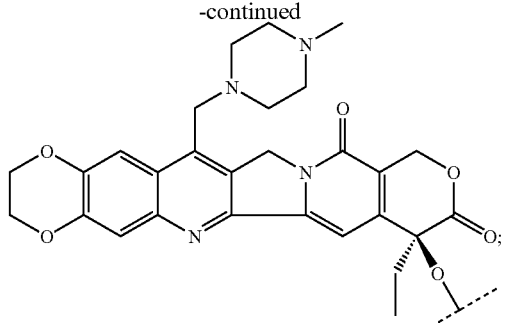

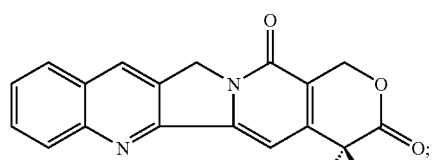

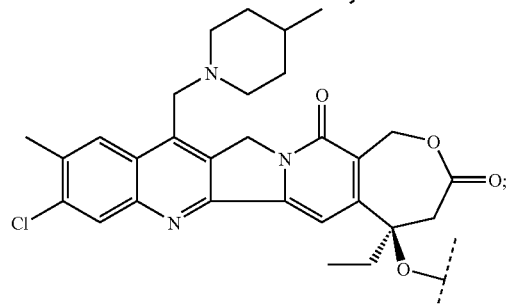

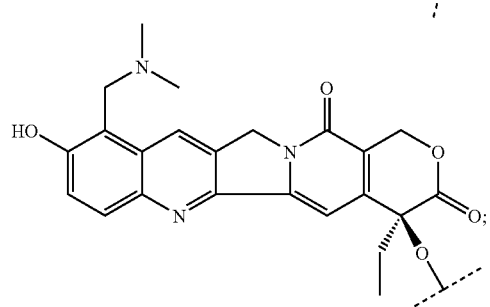

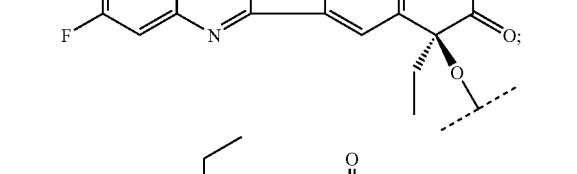

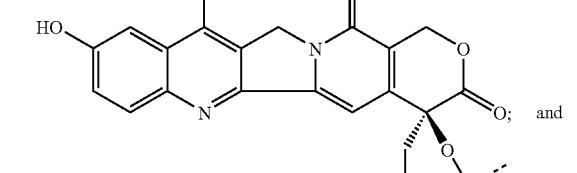

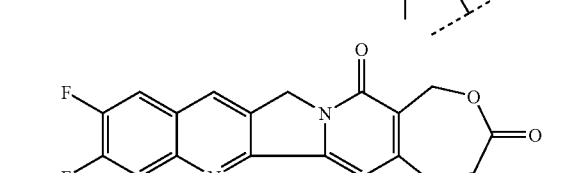

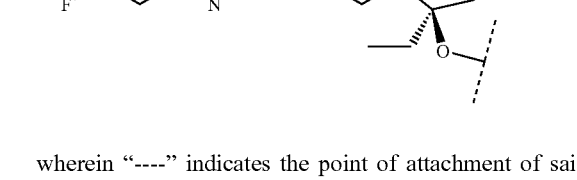

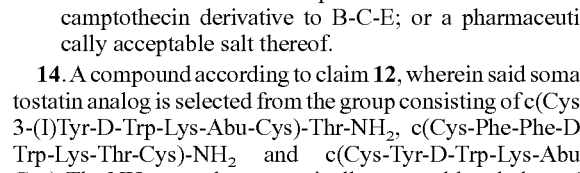

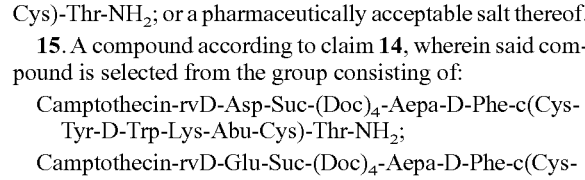

wherein "----" indicates the point of attachment of said camptothecin derivative to B-C-E; or a pharmaceutically acceptable salt thereof.

14. A compound according to claim 12, wherein said somatostatin analog is selected from the group consisting of c(Cys-3-(I)Tyr-D-Trp-Lys-Abu-Cys)-Thr-$NH_2$, c(Cys-Phe-Phe-D-Trp-Lys-Thr-Cys)-$NH_2$ and c(Cys-Tyr-D-Trp-Lys-Abu-Cys)-Thr-$NH_2$; or a pharmaceutically acceptable salt thereof.

15. A compound according to claim 14, wherein said compound is selected from the group consisting of:

Camptothecin-rvD-Asp-Suc-$(Doc)_4$-Aepa-D-Phe-c(Cys-Tyr-D-Trp-Lys-Abu-Cys)-Thr-$NH_2$;

Camptothecin-rvD-Glu-Suc-$(Doc)_4$-Aepa-D-Phe-c(Cys-Tyr-D-Trp-Lys-Abu-Cys)-Thr-$NH_2$;

Camptothecin-rvD-Arg-Suc-(Doc)$_4$-Aepa-D-Phe-c(Cys-Tyr-D-Trp-Lys-Abu-Cys)-Thr-NH$_2$;

Camptothecin-rvD-Dap(Z)-Suc-(Doc)$_4$-Aepa-D-Phe-c(Cys-Tyr-D-Trp-Lys-Abu-Cys)-Thr-NH$_2$;

Camptothecin-rvD-Cha-Suc-(Doc)$_4$-Aepa-D-Phe-c(Cys-Tyr-D-Trp-Lys-Abu-Cys)-Thr-NH$_2$;

Camptothecin-rvD-Phe-Suc-(Doc)$_4$-Aepa-D-Phe-c(Cys-Tyr-D-Trp-Lys-Abu-Cys)-Thr-NH$_2$;

Camptothecin-rvD-Ala-Suc-(Doc)$_4$-Aepa-D-Phe-c(Cys-Tyr-D-Trp-Lys-Abu-Cys)-Thr-NH$_2$;

Camptothecin-rvDAsp-Suc-(Peg3)$_3$-Aepa-DPhe-c(Cys-Tyr-DTrp-Lys-Abu-Cys)-Thr-NH$_2$;

Camptothecin-rvDAsp-Suc-Peg$_{11}$-Aepa-DPhe-c(Cys-Tyr-DTrp-Lys-Abu-Cys)-Thr-NH$_2$;

or

Camptothecin-rvDGlu-Suc-(Doc)$_4$-Aepa-DPhe-c(Cys-Tyr-DTrp-Lys-Abu-Cys)-Thr-NH$_2$;

or a pharmaceutically acceptable salt thereof.

16. A compound according to claim 15, wherein said compound is selected from the group consisting of:

Camptothecin-rvD-Asp-Suc-(Doc)$_4$-Aepa-D-Phe-c(Cys-Tyr-D-Trp-Lys-Abu-Cys)-Thr-NH$_2$;

Camptothecin-rvD-Cha-Suc-(Doc)$_4$-Aepa-D-Phe-c(Cys-Tyr-D-Trp-Lys-Abu-Cys)-Thr-NH$_2$;

Camptothecin-rvDAsp-Suc-(Peg3)$_3$-Aepa-DPhe-c(Cys-Tyr-DTrp-Lys-Abu-Cys)-Thr-NH$_2$;

Camptothecin-rvDAsp-Suc-Peg$_{11}$-Aepa-DPhe-c(Cys-Tyr-DTrp-Lys-Abu-Cys)-Thr-NH$_2$;

or

Camptothecin-rvDGlu-Suc-(Doc)$_4$-Aepa-DPhe-c(Cys-Tyr-DTrp-Lys-Abu-Cys)-Thr-NH$_2$;

or a pharmaceutically acceptable salt thereof.

17. A method of treating a disease or condition in a subject in need thereof, said method comprising administering to said subject a therapeutically effective amount of a compound according to claim 12, a pharmaceutically acceptable salt thereof, or a pharmaceutical composition thereof, wherein said a disease or condition is characterized by undesired proliferation of cells that express one or more somatostatin receptors.

18. A method of decreasing tumor size in a subject in need thereof comprising administering a therapeutically effective amount of a compound according to claim 12, a pharmaceutically acceptable salt thereof, or a pharmaceutical composition thereof, wherein said therapeutically effective amount is that amount which decreases the size of said tumor in said subject.

19. A method of inhibiting the undesired proliferation of tumor cells in a subject in need thereof comprising administering a therapeutically effective amount of a compound according to claim 12, a pharmaceutically acceptable salt thereof, or a pharmaceutical composition thereof, wherein said therapeutically effective amount is that amount which inhibits the undesired proliferation of said tumor cells in said subject.

20. A method according to claim 19, wherein said a disease or condition is a type of cancer, wherein said cancer is selected from the group consisting of neuroendocrine tumors, fibrosis, benign prostatic hyperplasia, atherosclerosis, restenosis, breast cancer, colon cancer, pancreas cancer, prostate cancer, lung cancer, small cell lung cancer, ovarian cancer, epidermal cancer, non-Hodgkin's lymphoma, Hodgkin's lymphoma, leukemia, hematopoietic cancer, adrenal medullary tumors pheochromocytoma, neuroblastoma, ganglioneuroma, gastroenteropancreatic tumors, glucagonoma, vasoactiveintestinal polypeptide secreting tumor, non-functioning GEP tumors, paraganglioma, pituitary ademona, astrocytomas, benign and malignant bone tumors, differentiated thyroid carcinoma, papillary thyroid carcinoma, follicular thyroid carcinoma, Hurthle cell thyroid carcinoma, meningioma, and non-small cell lung cancer.

21. A method according to claim 19, wherein said cancer is prostate cancer.

22. A mixture comprising Camptothecin-rvD-Asp-Suc-(Doc)$_4$-Aepa-D-Phe-c(Cys-Tyr-D-Trp-Lys-Abu-Cys)-Thr-NH$_2$ and Camptothecin-rvAsp-Suc-(Doc)$_4$-Aepa-D-Phe-c(Cys-Tyr-D-Trp-Lys-Abu-Cys)-Thr-NH$_2$, or a pharmaceutically acceptable salt of each thereof.

23. A pharmaceutical composition comprising an effective amount of a mixture according to claim 22, or pharmaceutically acceptable salts thereof and a pharmaceutically acceptable carrier.

24. A method of treating a disease or condition in a subject in need thereof, said method comprising administering to said subject a therapeutically effective amount of a mixture of compounds according to claim 22, pharmaceutically acceptable salts thereof, or a pharmaceutical composition thereof, wherein said a disease or condition is characterized by undesired proliferation of cells that express one or more somatostatin receptors.

25. A method of decreasing tumor size in a subject in need thereof comprising administering a therapeutically effective amount of a compound according to claim 22, pharmaceutically acceptable salts thereof, or a pharmaceutical composition thereof, wherein said therapeutically effective amount is that amount which decreases the size of said tumor in said subject.

26. A method of inhibiting the undesired proliferation of tumor cells in a subject in need thereof comprising administering a therapeutically effective amount of a compound according to claim 22, pharmaceutically acceptable salts thereof, or a pharmaceutical composition thereof, wherein said therapeutically effective amount is that amount which inhibits the undesired proliferation of said tumor cells in said subject.

27. A method according to claim 24, wherein said a disease or condition is a type of cancer, wherein said cancer is selected from the group consisting of neuroendocrine tumors, fibrosis, benign prostatic hyperplasia, atherosclerosis, restenosis, breast cancer, colon cancer, pancreas cancer, prostate cancer, lung cancer, small cell lung cancer, ovarian cancer, epidermal cancer, non-Hodgkin's lymphoma, Hodgkin's lymphoma, leukemia, hematopoietic cancer, adrenal medullary tumors pheochromocytoma, neuroblastoma, ganglioneuroma, gastroenteropancreatic tumors, glucagonoma, vasoactiveintestinal polypeptide secreting tumor, non-functioning GEP tumors, paraganglioma, pituitary ademona, astrocytomas, benign and malignant bone tumors, differentiated thyroid carcinoma, papillary thyroid carcinoma, follicular thyroid carcinoma, Hurthle cell thyroid carcinoma, meningioma, and non-small cell lung cancer.

28. A method according to claim 26, wherein said cancer is prostate cancer.

* * * * *

SEQUENCE LISTING

<160> NUMBER OF SEQ ID NOS: 8

<210> SEQ ID NO 1
<211> LENGTH: 14
<212> TYPE: PRT
<213> ORGANISM: Homo sapiens

<400> SEQUENCE: 1

Ala Gly Cys Lys Asn Phe Phe Trp Lys Thr Phe Thr Ser Cys
1               5                   10

<210> SEQ ID NO 2
<211> LENGTH: 14
<212> TYPE: PRT
<213> ORGANISM: Homo sapiens
<220> FEATURE:
<221> NAME/KEY: MOD_RES

```
<222> LOCATION: (14)..(14)
<223> OTHER INFORMATION: AMIDATION

<400> SEQUENCE: 2

Tyr Gln Arg Leu Gly Asn Gln Trp Ala Val Gly His Leu Met
1               5                   10

<210> SEQ ID NO 3
<211> LENGTH: 8
<212> TYPE: PRT
<213> ORGANISM: Artificial Sequence
<220> FEATURE:
<223> OTHER INFORMATION: Bombesin analog
<220> FEATURE:
<221> NAME/KEY: MISC_FEATURE
<222> LOCATION: (5)..(5)
<223> OTHER INFORMATION: Xaa = beta-alanine (B-Ala)
<220> FEATURE:
<221> NAME/KEY: MISC_FEATURE
<222> LOCATION: (8)..(8)
<223> OTHER INFORMATION: Xaa = norleucine (Nle)
<220> FEATURE:
<221> NAME/KEY: MOD_RES
<222> LOCATION: (8)..(8)
<223> OTHER INFORMATION: NH2 or OH

<400> SEQUENCE: 3

Gln Trp Ala Val Xaa His Leu Xaa
1               5

<210> SEQ ID NO 4
<211> LENGTH: 16
<212> TYPE: PRT
<213> ORGANISM: Artificial
<220> FEATURE:
<223> OTHER INFORMATION: Camptothecin derivative
<220> FEATURE:
<221> NAME/KEY: MISC_FEATURE
<222> LOCATION: (1)..(1)
<223> OTHER INFORMATION: Xaa = rvGly (i.e., Gly in reverse orientation)
      bonded to a camptothecin moiety
<220> FEATURE:
<221> NAME/KEY: MISC_FEATURE
<222> LOCATION: (2)..(2)
<223> OTHER INFORMATION: Xaa = succinyl (Suc)
<220> FEATURE:
<221> NAME/KEY: MISC_FEATURE
<222> LOCATION: (3)..(6)
<223> OTHER INFORMATION: Xaa = 8-amino-3, 6-dioxaoctanoic acid (Doc)
<220> FEATURE:
<221> NAME/KEY: MISC_FEATURE
<222> LOCATION: (7)..(7)
<223> OTHER INFORMATION: Xaa = 4-(2-aminoethyl)-1-carboxy methyl-
      piperazine (Aepa)
<220> FEATURE:
<221> NAME/KEY: MISC_FEATURE
<222> LOCATION: (8)..(8)
<223> OTHER INFORMATION: Xaa = norleucine (Nle)
<220> FEATURE:
<221> NAME/KEY: MISC_FEATURE
<222> LOCATION: (13)..(13)
<223> OTHER INFORMATION: Xaa = beta-alanine (B-Ala)
<220> FEATURE:
<221> NAME/KEY: MISC_FEATURE
<222> LOCATION: (16)..(16)
<223> OTHER INFORMATION: Xaa = norleucine (Nle)
<220> FEATURE:
<221> NAME/KEY: MOD_RES
<222> LOCATION: (16)..(16)
<223> OTHER INFORMATION: AMIDATION

<400> SEQUENCE: 4

Xaa Xaa Xaa Xaa Xaa Xaa Xaa Xaa Gln Trp Ala Val Xaa His Leu Xaa
1               5                   10                  15
```

```
<210> SEQ ID NO 5
<211> LENGTH: 16
<212> TYPE: PRT
<213> ORGANISM: Artificial
<220> FEATURE:
<223> OTHER INFORMATION: Camptothecin derivative
<220> FEATURE:
<221> NAME/KEY: MISC_FEATURE
<222> LOCATION: (1)..(1)
<223> OTHER INFORMATION: Xaa = rvGly (i.e., Gly in reverse orientation)
      bonded to a camptothecin moiety
<220> FEATURE:
<221> NAME/KEY: MISC_FEATURE
<222> LOCATION: (2)..(2)
<223> OTHER INFORMATION: Xaa = succinyl (Suc)
<220> FEATURE:
<221> NAME/KEY: MISC_FEATURE
<222> LOCATION: (3)..(6)
<223> OTHER INFORMATION: Xaa = 8-amino-3, 6-dioxaoctanoic acid (Doc)
<220> FEATURE:
<221> NAME/KEY: MISC_FEATURE
<222> LOCATION: (7)..(7)
<223> OTHER INFORMATION: Xaa = 4-(2-aminoethyl)-1-carboxy methyl-
      piperazine (Aepa)
<220> FEATURE:
<221> NAME/KEY: MISC_FEATURE
<222> LOCATION: (8)..(8)
<223> OTHER INFORMATION: Xaa = 6-aminohexanoic acid (Ahx)
<220> FEATURE:
<221> NAME/KEY: MISC_FEATURE
<222> LOCATION: (13)..(13)
<223> OTHER INFORMATION: Xaa = beta-alanine (B-Ala)
<220> FEATURE:
<221> NAME/KEY: MISC_FEATURE
<222> LOCATION: (16)..(16)
<223> OTHER INFORMATION: Xaa = norleucine (Nle)
<220> FEATURE:
<221> NAME/KEY: MOD_RES
<222> LOCATION: (16)..(16)
<223> OTHER INFORMATION: AMIDATION

<400> SEQUENCE: 5

Xaa Xaa Xaa Xaa Xaa Xaa Xaa Xaa Gln Trp Ala Val Xaa His Leu Xaa
1               5                   10                  15

<210> SEQ ID NO 6
<211> LENGTH: 17
<212> TYPE: PRT
<213> ORGANISM: Artificial
<220> FEATURE:
<223> OTHER INFORMATION: Camptothecin derivative
<220> FEATURE:
<221> NAME/KEY: MISC_FEATURE
<222> LOCATION: (1)..(1)
<223> OTHER INFORMATION: Xaa = rvGly (i.e., Gly in reverse orientation)
      bonded to a camptothecin moiety
<220> FEATURE:
<221> NAME/KEY: MISC_FEATURE
<222> LOCATION: (2)..(2)
<223> OTHER INFORMATION: Xaa = succinyl (Suc)
<220> FEATURE:
<221> NAME/KEY: MISC_FEATURE
<222> LOCATION: (3)..(6)
<223> OTHER INFORMATION: Xaa = 8-amino-3, 6-dioxaoctanoic acid (Doc)
<220> FEATURE:
<221> NAME/KEY: MISC_FEATURE
<222> LOCATION: (7)..(7)
<223> OTHER INFORMATION: Xaa = 4-(2-aminoethyl)-1-carboxy methyl-
      piperazine (Aepa)
<220> FEATURE:
<221> NAME/KEY: MISC_FEATURE
<222> LOCATION: (9)..(9)
<223> OTHER INFORMATION: Xaa = 4-aminobutyric acid (Gaba)
<220> FEATURE:
<221> NAME/KEY: MISC_FEATURE
<222> LOCATION: (14)..(14)
<223> OTHER INFORMATION: Xaa = beta-alanine (B-Ala)
```

```
<220> FEATURE:
<221> NAME/KEY: MISC_FEATURE
<222> LOCATION: (17)..(17)
<223> OTHER INFORMATION: Xaa = norleucine (Nle)
<220> FEATURE:
<221> NAME/KEY: MOD_RES
<222> LOCATION: (17)..(17)
<223> OTHER INFORMATION: AMIDATION

<400> SEQUENCE: 6

Xaa Xaa Xaa Xaa Xaa Xaa Xaa Leu Xaa Gln Trp Ala Val Xaa His Leu
1               5                   10                  15

Xaa

<210> SEQ ID NO 7
<211> LENGTH: 17
<212> TYPE: PRT
<213> ORGANISM: Artificial
<220> FEATURE:
<223> OTHER INFORMATION: Camptothecin derivative
<220> FEATURE:
<221> NAME/KEY: MISC_FEATURE
<222> LOCATION: (1)..(1)
<223> OTHER INFORMATION: Xaa = rvGly (i.e., Gly in reverse orientation)
      bonded to a camptothecin moiety
<220> FEATURE:
<221> NAME/KEY: MISC_FEATURE
<222> LOCATION: (2)..(2)
<223> OTHER INFORMATION: Xaa = succinyl (Suc)
<220> FEATURE:
<221> NAME/KEY: MISC_FEATURE
<222> LOCATION: (3)..(6)
<223> OTHER INFORMATION: Xaa = 8-amino-3, 6-dioxaoctanoic acid (Doc)
<220> FEATURE:
<221> NAME/KEY: MISC_FEATURE
<222> LOCATION: (7)..(7)
<223> OTHER INFORMATION: Xaa = 4-(2-aminoethyl)-1-carboxy methyl-
      piperazine (Aepa)
<220> FEATURE:
<221> NAME/KEY: MISC_FEATURE
<222> LOCATION: (8)..(8)
<223> OTHER INFORMATION: Xaa = 4-aminobutyric acid (Gaba)
<220> FEATURE:
<221> NAME/KEY: MISC_FEATURE
<222> LOCATION: (14)..(14)
<223> OTHER INFORMATION: Xaa = beta-alanine (B-Ala)
<220> FEATURE:
<221> NAME/KEY: MISC_FEATURE
<222> LOCATION: (17)..(17)
<223> OTHER INFORMATION: Xaa = norleucine (Nle)
<220> FEATURE:
<221> NAME/KEY: MOD_RES
<222> LOCATION: (17)..(17)
<223> OTHER INFORMATION: AMIDATION

<400> SEQUENCE: 7

Xaa Xaa Xaa Xaa Xaa Xaa Xaa Xaa Asn Gln Trp Ala Val Xaa His Leu
1               5                   10                  15

Xaa

<210> SEQ ID NO 8
<211> LENGTH: 17
<212> TYPE: PRT
<213> ORGANISM: Artificial
<220> FEATURE:
<223> OTHER INFORMATION: Camptothecin derivative
<220> FEATURE:
<221> NAME/KEY: MISC_FEATURE
<222> LOCATION: (1)..(1)
<223> OTHER INFORMATION: Xaa = rvGly (i.e., Gly in reverse orientation)
      bonded to a camptothecin moiety
<220> FEATURE:
<221> NAME/KEY: MISC_FEATURE
<222> LOCATION: (2)..(2)
```

```
<223> OTHER INFORMATION: Xaa = succinyl (Suc)
<220> FEATURE:
<221> NAME/KEY: MISC_FEATURE
<222> LOCATION: (3)..(6)
<223> OTHER INFORMATION: Xaa = 8-amino-3, 6-dioxaoctanoic acid (Doc)
<220> FEATURE:
<221> NAME/KEY: MISC_FEATURE
<222> LOCATION: (7)..(7)
<223> OTHER INFORMATION: Xaa = 4-(2-aminoethyl)-1-carboxy methyl-
      piperazine (Aepa)
<220> FEATURE:
<221> NAME/KEY: MISC_FEATURE
<222> LOCATION: (8)..(8)
<223> OTHER INFORMATION: Xaa =  5-aminopentanoic acid (Apn)
<220> FEATURE:
<221> NAME/KEY: MISC_FEATURE
<222> LOCATION: (14)..(14)
<223> OTHER INFORMATION: Xaa = beta-alanine (B-Ala)
<220> FEATURE:
<221> NAME/KEY: MISC_FEATURE
<222> LOCATION: (17)..(17)
<223> OTHER INFORMATION: Xaa = norleucine (Nle)
<220> FEATURE:
<221> NAME/KEY: MOD_RES
<222> LOCATION: (17)..(17)
<223> OTHER INFORMATION: AMIDATION

<400> SEQUENCE: 8

Xaa Xaa Xaa Xaa Xaa Xaa Xaa Xaa Asn Gln Trp Ala Val Xaa His Leu
1               5                   10                  15

Xaa
```